United States Patent
Guo et al.

(10) Patent No.: US 10,501,805 B2
(45) Date of Patent: Dec. 10, 2019

(54) METHODS FOR DETERMINING RESPONSIVENESS TO MEK/ERK INHIBITORS

(71) Applicant: CROWN BIOSCIENCE, INC. (TAICANG), Taicang, Jiangsu (CN)

(72) Inventors: Sheng Guo, Jiangsu (CN); Wubin Qian, Jiangsu (CN); Jinying Ning, Jiangsu (CN); Jing Zhang, Jiangsu (CN); Jixian Li, Jiangsu (CN); Zhu Mei, Jiangsu (CN)

(73) Assignee: CROWN BIOSCIENCE, INC. (TAICANG), Taicang Jiangsu (CN)

( * ) Notice: Subject to any disclaimer, the term of this patent is extended or adjusted under 35 U.S.C. 154(b) by 56 days.

(21) Appl. No.: 15/301,379

(22) PCT Filed: Apr. 3, 2015

(86) PCT No.: PCT/CN2015/075884
§ 371 (c)(1),
(2) Date: Oct. 1, 2016

(87) PCT Pub. No.: WO2015/149721
PCT Pub. Date: Oct. 8, 2015

(65) Prior Publication Data
US 2017/0114414 A1 Apr. 27, 2017

(30) Foreign Application Priority Data
Apr. 4, 2014 (CN) .......................... 2014 1 0135569

(51) Int. Cl.
*C12P 19/34* (2006.01)
*C12Q 1/68* (2018.01)
*C12Q 1/6886* (2018.01)

(52) U.S. Cl.
CPC ..... *C12Q 1/6886* (2013.01); *C12Q 2600/106* (2013.01); *C12Q 2600/156* (2013.01)

(58) Field of Classification Search
CPC ..... A61K 38/00; A61K 38/005; C12N 9/6489
See application file for complete search history.

(56) References Cited

U.S. PATENT DOCUMENTS

| | | | |
|---|---|---|---|
| 4,503,035 A | 3/1985 | Pestka et al. |
| 4,530,901 A | 7/1985 | Weissmann |
| 5,231,176 A | 7/1993 | Goeddel et al. |
| 5,792,783 A | 8/1998 | Tang et al. |
| 5,834,504 A | 11/1998 | Tang et al. |
| 5,883,113 A | 3/1999 | Tang et al. |
| 5,886,020 A | 3/1999 | Tang et al. |
| 6,235,764 B1 | 5/2001 | Larson et al. |
| 7,618,814 B2 | 11/2009 | Bentwich |
| 8,022,205 B2 | 9/2011 | Shimma et al. |
| 2014/0024539 A1 | 1/2014 | Craig et al. |

FOREIGN PATENT DOCUMENTS

| | | |
|---|---|---|
| CN | 103402517 A | 11/2013 |
| CN | 103571848 A | 2/2014 |
| EP | 0390323 A2 | 10/1990 |
| WO | 95/21613 A1 | 8/1995 |
| WO | 97/15666 A1 | 5/1997 |
| WO | 97/19110 A1 | 5/1997 |
| WO | 97/22596 A1 | 6/1997 |
| WO | 97/32856 A1 | 9/1997 |
| WO | 98/02437 A1 | 1/1998 |
| WO | 98/02438 A1 | 1/1998 |
| WO | 98/50356 A1 | 11/1998 |
| WO | 98/54093 A1 | 12/1998 |
| WO | 99/10349 A1 | 3/1999 |
| WO | 99/16755 A1 | 4/1999 |
| WO | 99/24440 A1 | 5/1999 |
| WO | 99/61422 A1 | 12/1999 |
| WO | 99/62890 A1 | 12/1999 |
| WO | 2008/082730 A2 | 7/2008 |
| WO | 2009/099163 A1 | 8/2009 |
| WO | 2012/068468 A1 | 5/2012 |

OTHER PUBLICATIONS

Livak, K.J. Genetic Analysis: Biomolecular Engineering, 14 (1999) 143-149 (Year: 1999).*
Dyczynska, E. et al. Int. J. Cancer: 122, 2634-2640 (2008) (Year: 2008).*
Jiao, X. et al. Genes, Chromosomes & Cancer 51:480-489 (2012) (Year: 2012).*
Ma, Y. et al. Nature Reviews, Dec. 2004, vol. 4, p. 966-977 (Year: 2004).*
Jiao, X. et al, Somatic mutations in the notch, NF-KB, PIK3CA, and hedgehog pathways in human breast cancers. Genes, Chromosomes & Cancer, vol. 51, Issue 5, May 2012, pp. 480-489, Table S2. Primers used for PCR amplification and sequencing. (Year: 2012).*
Falchook, G.W. et al., Lancet Oncol 2012; 13: 782-89. (Year: 2012).*
Communication pursuant to Article 94(3) EPC, dated Dec. 3, 2018.
Gerald S Falchook et al., "Activity of the MEK Inhibitor Trametinib (GSK1120212) in Advanced Melanoma in a Phase I, Dose-escalation Trial", Lancet Oncol, Aug. 2012, No. 8, vol. 13, pp. 782-789.

(Continued)

*Primary Examiner* — Stephen T Kapushoc
(74) *Attorney, Agent, or Firm* — Jun He Law Offices P.C.; James J. Zhu

(57) ABSTRACT

A method for predicting the responsiveness of a cancer cell to an MEK inhibitor, comprising detecting the presence of at least one mutation in one or more genes selected from the group consisting of ADAM12, COL14A1, TNN, and TP53, in the cancer cell, by contacting a nucleic acid sample derived from the cancer cell with at least one oligonucleotide which allows specific detection of the mutation; wherein presence of mutation in ADAM12, COL14A1, TNN, TP53 and/or any combination thereof is indicative of decreased responsiveness of the cancer cell to the ERK inhibitor.

15 Claims, 10 Drawing Sheets
Specification includes a Sequence Listing.

(56) References Cited

OTHER PUBLICATIONS

Carl C. Schimanski et al., "Sensitive Detection of K-ras Mutations Augments Diagnosis of Colorectal Cancer Metastases in the Liver"; Cancer Research 59, 5169-5175, Oct. 15, 1999.
Kazuya Yamashita et al., "Simplified rapid non-radioactive PCR-SSCP method applied to K-ras mutation analysis"; pathology International 1996; 46: 801-804.
Michael S. O'Reilly et al., "Angiostatin: A Novel Angiogenesis Inhibitor That Mediates the Suppression of Metastases by a Lewis Lung Carcinoma" ; Cell, vol. 79, 315-328, Oct. 21, 1994, Copyright 0 1994 by Cell Press.
Yihai Cao et al., "Kringle Domains of Human Angiostatin Characterization of the Anti-Proliferative Activity on Endothelial Cells"; The Journal of Biological Chemistry, vol. 271, No. 46, Issue of Nov. 15, pp. 29461-29467, 1996.
Yihai Cao et al., "Kringle 5 of Plasminogen is a Novel Inhibitor of Endothelial Cell Growth"; The Journal of Biological Chemistry, vol. 272, No. 36, Issue of Sep. 5, pp. 22924-22928, 1997.
Michael S. O'Reilly et al., "Endostatin: An Endogenous Inhibitor of Angiogenesis and Tumor Growth"; Cell, vol. 88, 277-285, Jan. 24, 1997.
William A. Frazier, "Thrombospondins"; Current Opinion in Cell Biology 1991, 3:792-799.
Erick J. Morris et al., "Discovery of a Novel ERK Inhibitor with Activity in Models of Acquired Resistance to BRAF and MEK Inhibitors"; Published Online First Apr. 24, 2013; DOI: 10.1158/2159-8290.CD-13-0070.
Manuel Rieber et al., "p53 inactivation decreases dependence on estrogen/ERK signalling for proliferation but promotes EMT and susceptibility to 3-bromopyruvate in ERa+ breast cancer MCF-7 cells"; Biochemical Pharmacology 88 (2014) 169-177.
JA McCubrey et al., "Involvement of p53 and Raf/MEK/ERK pathways in hematopoietic drug resistance"; Leukemia (2008) 22, 2080-2090.
Solit David B et al., "BRAF mutation predicts sensitivity to MEK inhibition", nature, Macmillan Journals LTD, etc, vol. 439, No. 7074, Jan. 19, 2006 (Jan. 19, 2006), pp. 358-362, XP002547208.
N Nakayama et al., "KRAS or BRAF mutation status is a useful predictor of sensitivity to MEK inhibition in ovarian cancer", British Journal of Cancer, vol. 99, No. 12, Dec. 16, 2008 (Dec. 16, 2008), pp. 2020-2028, XP055174779.
Samuel et al., "QS282. BRAF mutation status, but not ERK activation is predictive of response to the MEK inhibitor AZD6244 in Colorectal cancer", Journal of surgical research, Academic press Inc., San Diego, CA, US, vol. 144, No. 2, Feb. 1, 2008 (Feb. 1, 2008), p. 379, XP022474030.
Jessie Villanueva et al., "Concurrent MEK2 1-15 mutation and BRAF amplification confer resistance to BRAF and MEK inhibitors in Melanoma", Cell reports, vol. 4, No. 6, Sep. 1, 2013 (Sep. 1, 2013), pp. 1090-1099, XP055344891.
Yue Qi et al., "Phenotypic Diversity of Breast Cancer-Related Mutations in Metalloproteinase-Disintegrin ADAM12", Plos One, vol. 9, No. 3, Mar. 20, 2014 (Mar. 20, 2014), p. 92536, XP055414388.
Emilia Dyczynska et al.,"Breast cancer-associated mutations in metalloprotease disintegrin ADAM12 interfere with the intracellular trafficking and processing of the protein", International Journal of cancer, vol. 122, No. 11, Jan. 1, 2008 (Jan. 1, 2008), pp. 2634-2640, XP055414390.
Supplementary EP search report for 15773840.2.

\* cited by examiner

SEQUENCE LISTING

<160> NUMBER OF SEQ ID NOS: 10

<210> SEQ ID NO 1
<211> LENGTH: 8050
<212> TYPE: DNA
<213> ORGANISM: Homo sapiens

<400> SEQUENCE: 1

```
acgccgccaa ctggcggggg tgcggggag  acaataattt gttccgcggt aataagaacg      60
gtgactgctg gccgtggatc catttcacag gcctgccttc tctcactaac gctcttccta     120
gtccccgggc caactcggac agtttgctca tttattgcaa cggtcaaggc tggcttgtgc     180
cagaacggcg cgcgcgcgcg cacgcacgca cacacacggg gggaaacttt tttaaaaatg     240
aaaggctaga agagctcagc ggcggcgcgg gcgctgcgcg agggctccgg agctgactcg     300
ccgaggcagg aaatccctcc ggtcgcgacg cccgccccg  gctcggcgcc cgcgtgggat     360
ggtgcagcgc tcgccgccgg gcccgagagc tgctgcactg aaggccggcg acgatggcag     420
cgcgcccgct gcccgtgtcc cccgcccgcg ccctcctgct cgccctggcc ggtgctctgc     480
tcgcgccctg cgaggcccga ggggtgagct tatggaacca aggaagagct gatgaagttg     540
tcagtgcctc tgttgggagt ggggacctct ggatcccagt gaagagcttc gactccaaga     600
atcatccaga agtgctgaat attcgactac aacgggaaag caaagaactg atcataaatc     660
tggaaagaaa tgaaggtctc attgccagca gtttcacgga aacccactat ctgcaagacg     720
gtactgatgt ctccctcgct cgaaattaca cggtaattct gggtcactgt tactaccatg     780
gacatgtacg gggatattct gattcagcag tcagtctcag cacgtgttct ggtctcaggg     840
gacttattgt gtttgaaaat gaaagctatg tcttagaacc aatgaaaagt gcaaccaaca     900
gatacaaact cttcccagcg aagaagctga aaagcgtccg gggatcatgt ggatcacatc     960
acaacacacc aaacctcgct gcaaagaatg tgtttccacc accctctcag acatgggcaa    1020
gaaggcataa aagagagacc ctcaaggcaa ctaagtatgt ggagctggtg atcgtggcag    1080
acaaccgaga gtttcagagg caaggaaaag atctggaaaa agttaagcag cgattaatag    1140
agattgctaa tcacgttgac aagttttaca gaccactgaa cattcggatc gtgttggtag    1200
gcgtggaagt gtggaatgac atggacaaat gctctgtaag tcaggaccca ttcaccagcc    1260
tccatgaatt tctggactgg aggaagatga agcttctacc tcgcaaatcc catgacaatg    1320
cgcagcttgt cagtgggggtt tatttccaag ggaccaccat cggcatggcc ccaatcatga    1380
gcatgtgcac ggcagaccag tctgggggaa ttgtcatgga ccattcagac aatcccctg     1440
```

```
gtgcagccgt gaccctggca catgagctgg gccacaattt cgggatgaat catgacacac   1500
tggacagggg ctgtagctgt caaatggcgg ttgagaaagg aggctgcatc atgaacgctt   1560
ccaccgggta cccatttccc atggtgttca gcagttgcag caggaaggac ttggagacca   1620
gcctggagaa aggaatgggg gtgtgcctgt ttaacctgcc ggaagtcagg gagtctttcg   1680
ggggccagaa gtgtgggaac agatttgtgg aagaaggaga ggagtgtgac tgtggggagc   1740
cagaggaatg tatgaatcgc tgctgcaatg ccaccacctg taccctgaag ccggacgctg   1800
tgtgcgcaca tgggctgtgc tgtgaagact gccagctgaa gcctgcagga acagcgtgca   1860
gggactccag caactcctgt gacctcccag agttctgcac aggggccagc cctcactgcc   1920
cagccaacgt gtacctgcac gatgggcact catgtcagga tgtggacggc tactgctaca   1980
atggcatctg ccagactcac gagcagcagt gtgtcacgct ctggggacca ggtgctaaac   2040
ctgcccctgg gatctgcttt gagagagtca attctgcagg tgatccttat ggcaactgtg   2100
gcaaagtctc gaagagttcc tttgccaaat gcgagatgag agatgctaaa tgtgaaaaaa   2160
tccagtgtca aggaggtgcc agccggccag tcattggtac caatgccgtt ccatagaaa   2220 caaacatccc cctgcagcaa ggaggccgga ttctgtgccg ggggacccac gtgtacttgg   2280
gcgatgacat gccggaccca gggcttgtgc ttgcaggcac aaagtgtgca gatggaaaaa   2340
tctgcctgaa tcgtcaatgt caaaatatta gtgtctttgg ggttcacgag tgtgcaatgc   2400
agtgccacgg cagaggggtg tgcaacaaca ggaagaactg ccactgcgag gcccactggg   2460
cacctccctt ctgtgacaag tttggctttg gaggaagcac agacagcggc cccatccggc   2520
aagcagataa ccaaggttta accataggaa ttctggtgac catcctgtgt cttcttgctg   2580
ccggatttgt ggtttatctc aaaaggaaga ccttgatacg actgctgttt acaaataaga   2640
agaccaccat tgaaaaacta aggtgtgtgc gcccttcccg gccaccccgt ggcttccaac   2700
cctgtcaggc tcacctcggc caccttggaa aaggcctgat gaggaagccg ccagattcct   2760
acccaccgaa ggacaatccc aggagattgc tgcagtgtca gaatgttgac atcagcagac   2820
ccctcaacgg cctgaatgtc cctcagcccc agtcaactca gcgagtgctt cctcccctcc   2880
accgggctcc acgtgcacct agcgtccctg ccagacccct gccagccaag cctgcactta   2940
ggcaggccca ggggacctgt aagccaaacc cccctcagaa gcctctgcct gcagatcctc   3000
tggccagaac aactcggctc actcatgcct tggccaggac cccaggacaa tgggagactg   3060
ggctccgcct ggcacccctc agacctgctc cacaatatcc acaccaagtg cccagatcca   3120
cccacaccgc ctatattaag tgagaagccg acacctttt tcaacagtga agacagaagt   3180
ttgcactatc tttcagctcc agttggagtt ttttgtacca actttttagga ttttttttaa   3240 tgtttaaaac atcattacta taagaacttt gagctactgc cgtcagtgct gtgctgtgct   3300
atggtgctct gtctacttgc tcaggtactt gtaaattatt aatttatgca gaatgttgat   3360
tacagtgcag tgcgctgtag taggcatttt taccatcact gagttttcca tggcaggaag   3420
gcttgttgtg cttttagtat tttagtgaac ttgaaatatc ctgcttgatg ggattctgga   3480
caggatgtgt ttgctttctg atcaaggcct tattggaaag cagtccccca actacccca   3540 gctgtgctta tggtaccaga tgcagctcaa gagatcccaa gtagaatctc agttgatttt   3600
ctggattccc catctcaggc cagagccaag gggcttcagg tccaggctgt gtttggcttt   3660
cagggaggcc ctgtgcccct tgacaactgg caggcaggct cccagggaca cctgggagaa   3720
atctggcttc tggccaggaa gctttggtga gaacctgggt tgcagacagg aatcttaagg   3780
```

-continued

```
tgtagccaca ccaggataga gactggaaca ctagacaagc cagaacttga ccctgagctg    3840
accagccgtg agcatgtttg aagggtct gtagtgtcac tcaaggcggt gcttgataga      3900
aatgccaagc acttctttt ctcgctgtcc tttctagagc actgccacca gtaggttatt    3960
tagcttggga aggtggtgt ttctgtaaga aacctactgc ccaggcactg caaaccgcca     4020
cctccctata ctgcttggag ctgagcaaat caccacaaac tgtaatacaa tgatcctgta    4080
ttcagacaga tgaggctttc catgggacca caactatttt cagatgtgaa ccattaacca    4140
gatctagtca atcaagtctg tttactgcaa ggttcaactt attaacaatt aggcagactc    4200
tttatgcttg caaaaactac aaccaatgga atgtgatgtt catgggtata gttcatgtct    4260
gctatcatta ttcgtagata ttggacaaag aaccttctct atggggcatc ctctttttcc    4320
aacttggctg caggaatctt taaaagatgc ttttaacaga gtctgaacct atttcttaaa    4380
cacttgcaac ctacctgttg agcatcacag aatgtgataa ggaaatcaac ttgcttatca    4440
acttcctaaa tattatgaga tgctggcttg ggcagcatcc ccttgaactc ttcactcttc    4500
aaatgcctga ctagggagcc atgtttcaca aggtctttaa agtgactaat ggcatgagaa    4560
atacaaaaat actcagataa ggtaaaatgc catgatgcct ctgtcttctg gactggtttt    4620
cacattagaa gacaattgac aacagttaca taattcactc tgagtgtttt atgagaaagc    4680
cttcttttgg gggtcaacag ttttcctatg ctttgaaaca gaaaatatg taccaagaat      4740 cttggtttgc cttccagaaa acaaaactgc atttcacttt cccggtgttc cccactgtat    4800
ctaggcaaca tagtattcat gactatggat aaactaaaca cgtgacacaa acacacacaa    4860
aagggaaccc agctctaata cattccaact cgtatagcat gcatctgttt attctatagt    4920
tattaagttc tttaaaatgt aaagccatgc tggaaaataa tactgctgag atacatacag    4980
aattactgta actgattaca cttggtaatt gtactaaagc caaacatata tatactatta    5040
aaaaggttta cagaatttta tggtgcatta cgtgggcatt gtcttttag atgcccaaat     5100 ccttagatct ggcatgttag cccttcctcc aattataaga ggatatgaac tgagttttc     5160 ttttgttgtt tgttcttagc tgtaattcct atgcttctat ttcagagagc caggagagtt    5220
tgatattaaa ggaggttaaa actgtgatct tatgccatgt catcaatggc cacttagggg    5280
ccatggctga tgacacattc ttatctctac agtactaatg tgttattata gagccatgca    5340
ttttatttct gaataagaac atatttaaac taatattccc ttacaatatg gacagtatta    5400
atccttccaa gatgcagtat ttatcaagtg aagcatattt agcagcaaat tccattttaa    5460
cataacttag gaaccaataa ccagggtgtt ttgtggttgg gggaggcacg gggtggagta    5520 ttcttttta tatcctcaaa acaaaaaaaa tcaatactta tatttcaatg gcaatctagt     5580
atttttttaa aagactgtat aggcatgaat aatagaggtg gtttgagttt tgtagggcca    5640
tcacctggaa agtcaatgtg actagacaca aagtagccca gaggctactt ttcttcctac    5700
agcttattat agttgtaggt tctatgacct cacttcatgg gttccaggca attccgctga    5760
aaggtttgtc tcctgaaatt ttttaagttt gttttcctga cacatgtaat cagatgtgta    5820
gcaaccgagg gaaacgaagc ctaacattct ccattgtgga aatacacaca ggaggttaca    5880
tttcacagcg tggattttc cagcttacac atgtgggatg acatcacaga aaccacaaaa     5940
gcagcaaatt aaactgtagg agagtcaata ctcctgacga gtctcggggg gggggcattt    6000
ttatgccttc ttaactttat gagaattctc aggctgaact ataggccatt gttcccaggc    6060
aaatcaatac atcaatgcat cctcaaaaaa aaaaaaaaa aaaaaaaacc ggctaaaact     6120
gtgtcaaaat gttcttaagg agcctatggt ctccacggtg ctaaaagag cctggtgctg     6180
```

-continued

```
ggccgactgg cagggctgag catcctcctg cccctcgcc actgatgttt actaagcact    6240
ctgagccaat gagaccccca gcagcagaaa gggcacaagg tggcgccagg gcagcagggc    6300
cagatctttc tcatgcacct cgacctcttg cagactttct tcgtgagatg tactactcat    6360
ttcaaaactg ctttgcaggg ctccctatg tattcggggg gcccacggca cactcaggct     6420
ggagatcctt cctcactgcg ctcaagatgg cctcagccag acaccagtta cccagctgaa    6480
agtcacaatc cctcccagaa gtctcccaac actagtgctg accagaggtg gggctctcag    6540
gctaggagtt tcacacacaa tgacaggctg ctggggggaca ttgcaggacc ccttttcctc   6600
tcctctccat gctagaagcc agccctaggc agctgcagtt actccctgtg actcagcagc    6660
aggctgattc aacacagctg cccacacaaa gccagtggct aatacatctg tttacctttc    6720
cctatcaccc agacacaagc cccttttccca ggtcaaacca caggccgatg catctccagt    6780
ttgacagtca aatcactact tccattgcta ctttagatca gccaaagtgg tgactgctgc    6840
agtgtgtggc tatcccctaca aggcccaccc aagggatgcc caaagcccaa ccttctccag    6900
ggctgcagcc cagagcaacc ccaccagcct aagtccagca gaggacctcc cacccaatgt    6960
cttgttctaa ttagaagggg aagttagcca cagaaaatca acttatctat aattacaaaa    7020
ttctcttgac tcaccttaaa gttcctattg acatctactg cttttaaacc tatttgaaaa    7080
ctctgatact aaaacaaatg acactctaag aaagtttggg agccccatgc tgagaaccat    7140
ttctgtgcag tgaggatgtt tccagaagct acttacctac atgtgaatgt gccatttcct    7200
ttccttttgt agagaaaatc cccttttactt tttggaacag taatggcagc ttctagtaca    7260
gccattacag tttcatatga gaaaaattaa gaataactat aaaattgtta aaatatccaa    7320
taatggataa tgatggccag aagatttaac atacaaagta attctcaatg taaagctatt    7380
cagctcttcc aggttgaatg ccctgtaacc caccctgacc ttccacatca tcttcaaaaa    7440
gcagtttctc tgttccccat gattctccta taaggtaact ctttagtcct ccatttagca    7500
cattttaaat cctccaaaga ataagtatca tgtgattatt ttagctttac aaaaaaaaag    7560
ttgaatggcg ttttatttc atggcctata agcaggtacc ttagtagggc agatataggga    7620
aaaacaaatt agagcaaaac aaatcctcta caaatccaag gcaggaaaag tggtggcaga    7680
gtgactcatt ctcctgtccc tcccatcagg tcaaatcagg aggctgcagt gaatgcctgt    7740
tctttgaatg tgtagcagtt gttcctgtaa ctctttaaaa cttggctata ggctgtttag    7800
cacagtacag attaaagata cagttacgta aacagcaaag taattttata gtgcttcatc    7860
catttatcat gctttggttt gctaattttt tcacatacct ttttctatca cagtctgttg    7920
cttttgtaca catttctcat attggggttc gacaggtaaa cacaaactgc tatttcagta    7980
gaaaagtta ttgttatgaa tattaaaccc aataaattgt ataaggtaa atatcaaaaa      8040
aaaaaaaaa                                                           8050
```

<210> SEQ ID NO 2
<211> LENGTH: 909
<212> TYPE: PRT
<213> ORGANISM: Homo sapiens

<400> SEQUENCE: 2

Met Ala Ala Arg Pro Leu Pro Val Ser Pro Ala Arg Ala Leu Leu Leu
1               5                   10                  15

Ala Leu Ala Gly Ala Leu Leu Ala Pro Cys Glu Ala Arg Gly Val Ser
            20                  25                  30

-continued

```
Leu Trp Asn Gln Gly Arg Ala Asp Glu Val Val Ser Ala Ser Val Gly
         35                  40                  45

Ser Gly Asp Leu Trp Ile Pro Val Lys Ser Phe Asp Ser Lys Asn His
 50                  55                  60

Pro Glu Val Leu Asn Ile Arg Leu Gln Arg Glu Ser Lys Glu Leu Ile
 65                  70                  75                  80

Ile Asn Leu Glu Arg Asn Glu Gly Leu Ile Ala Ser Ser Phe Thr Glu
                 85                  90                  95

Thr His Tyr Leu Gln Asp Gly Thr Asp Val Ser Leu Ala Arg Asn Tyr
            100                 105                 110

Thr Val Ile Leu Gly His Cys Tyr Tyr His Gly His Val Arg Gly Tyr
            115                 120                 125

Ser Asp Ser Ala Val Ser Leu Ser Thr Cys Ser Gly Leu Arg Gly Leu
    130                 135                 140

Ile Val Phe Glu Asn Glu Ser Tyr Val Leu Glu Pro Met Lys Ser Ala
145                 150                 155                 160

Thr Asn Arg Tyr Lys Leu Phe Pro Ala Lys Lys Leu Lys Ser Val Arg
                165                 170                 175

Gly Ser Cys Gly Ser His His Asn Thr Pro Asn Leu Ala Ala Lys Asn
            180                 185                 190

Val Phe Pro Pro Ser Gln Thr Trp Ala Arg Arg His Lys Arg Glu
            195                 200                 205

Thr Leu Lys Ala Thr Lys Tyr Val Glu Leu Val Ile Val Ala Asp Asn
    210                 215                 220

Arg Glu Phe Gln Arg Gln Gly Lys Asp Leu Glu Lys Val Lys Gln Arg
225                 230                 235                 240

Leu Ile Glu Ile Ala Asn His Val Asp Lys Phe Tyr Arg Pro Leu Asn
                245                 250                 255

Ile Arg Ile Val Leu Val Gly Val Glu Val Trp Asn Asp Met Asp Lys
            260                 265                 270

Cys Ser Val Ser Gln Asp Pro Phe Thr Ser Leu His Glu Phe Leu Asp
            275                 280                 285

Trp Arg Lys Met Lys Leu Leu Pro Arg Lys Ser His Asp Asn Ala Gln
    290                 295                 300

Leu Val Ser Gly Val Tyr Phe Gln Gly Thr Thr Ile Gly Met Ala Pro
305                 310                 315                 320

Ile Met Ser Met Cys Thr Ala Asp Gln Ser Gly Gly Ile Val Met Asp
                325                 330                 335

His Ser Asp Asn Pro Leu Gly Ala Ala Val Thr Leu Ala His Glu Leu
            340                 345                 350

Gly His Asn Phe Gly Met Asn His Asp Thr Leu Asp Arg Gly Cys Ser
            355                 360                 365

Cys Gln Met Ala Val Glu Lys Gly Gly Cys Ile Met Asn Ala Ser Thr
    370                 375                 380

Gly Tyr Pro Phe Pro Met Val Phe Ser Ser Cys Ser Arg Lys Asp Leu
385                 390                 395                 400

Glu Thr Ser Leu Glu Lys Gly Met Gly Val Cys Leu Phe Asn Leu Pro
                405                 410                 415

Glu Val Arg Glu Ser Phe Gly Gly Gln Lys Cys Gly Asn Arg Phe Val
            420                 425                 430

Glu Glu Gly Glu Glu Cys Asp Cys Gly Glu Pro Glu Glu Cys Met Asn
            435                 440                 445

Arg Cys Cys Asn Ala Thr Thr Cys Thr Leu Lys Pro Asp Ala Val Cys
```

```
            450               455               460
Ala His Gly Leu Cys Cys Glu Asp Cys Gln Leu Lys Pro Ala Gly Thr
465                 470                475                480

Ala Cys Arg Asp Ser Ser Asn Ser Cys Asp Leu Pro Glu Phe Cys Thr
                485                490                495

Gly Ala Ser Pro His Cys Pro Ala Asn Val Tyr Leu His Asp Gly His
                500                505                510

Ser Cys Gln Asp Val Asp Gly Tyr Cys Tyr Asn Gly Ile Cys Gln Thr
            515                520                525

His Glu Gln Gln Cys Val Thr Leu Trp Gly Pro Gly Ala Lys Pro Ala
        530                535                540

Pro Gly Ile Cys Phe Glu Arg Val Asn Ser Ala Gly Asp Pro Tyr Gly
545                550                555                560

Asn Cys Gly Lys Val Ser Lys Ser Ser Phe Ala Lys Cys Glu Met Arg
                565                570                575

Asp Ala Lys Cys Gly Lys Ile Gln Cys Gln Gly Gly Ala Ser Arg Pro
                580                585                590

Val Ile Gly Thr Asn Ala Val Ser Ile Glu Thr Asn Ile Pro Leu Gln
            595                600                605

Gln Gly Gly Arg Ile Leu Cys Arg Gly Thr His Val Tyr Leu Gly Asp
        610                615                620

Asp Met Pro Asp Pro Gly Leu Val Leu Ala Gly Thr Lys Cys Ala Asp
625                630                635                640

Gly Lys Ile Cys Leu Asn Arg Gln Cys Gln Asn Ile Ser Val Phe Gly
                645                650                655

Val His Glu Cys Ala Met Gln Cys His Gly Arg Gly Val Cys Asn Asn
                660                665                670

Arg Lys Asn Cys His Cys Glu Ala His Trp Ala Pro Pro Phe Cys Asp
            675                680                685

Lys Phe Gly Phe Gly Gly Ser Thr Asp Ser Gly Pro Ile Arg Gln Ala
        690                695                700

Asp Asn Gln Gly Leu Thr Ile Gly Ile Leu Val Thr Ile Leu Cys Leu
705                710                715                720

Leu Ala Ala Gly Phe Val Val Tyr Leu Lys Arg Lys Thr Leu Ile Arg
                725                730                735

Leu Leu Phe Thr Asn Lys Lys Thr Thr Ile Glu Lys Leu Arg Cys Val
                740                745                750

Arg Pro Ser Arg Pro Pro Arg Gly Phe Gln Pro Cys Gln Ala His Leu
            755                760                765

Gly His Leu Gly Lys Gly Leu Met Arg Lys Pro Pro Asp Ser Tyr Pro
        770                775                780

Pro Lys Asp Asn Pro Arg Arg Leu Leu Gln Cys Gln Asn Val Asp Ile
785                790                795                800

Ser Arg Pro Leu Asn Gly Leu Asn Val Pro Gln Pro Gln Ser Thr Gln
                805                810                815

Arg Val Leu Pro Pro Leu His Arg Ala Pro Arg Ala Pro Ser Val Pro
            820                825                830

Ala Arg Pro Leu Pro Ala Lys Pro Ala Leu Arg Gln Ala Gln Gly Thr
        835                840                845

Cys Lys Pro Asn Pro Pro Gln Lys Pro Leu Pro Ala Asp Pro Leu Ala
    850                855                860

Arg Thr Thr Arg Leu Thr His Ala Leu Ala Arg Thr Pro Gly Gln Trp
865                870                875                880
```

Glu Thr Gly Leu Arg Leu Ala Pro Leu Arg Pro Ala Pro Gln Tyr Pro
            885                 890                 895

His Gln Val Pro Arg Ser Thr His Thr Ala Tyr Ile Lys
            900                 905

<210> SEQ ID NO 3
<211> LENGTH: 6464
<212> TYPE: DNA
<213> ORGANISM: Homo sapiens

<400> SEQUENCE: 3

| | | | | | |
|---|---|---|---|---|---|
| atctgatcct | gggctcccag | ctggagaggc | ggaggcagct | ccagggggct | ggaagtggaa | 60 |
| gcgcagcggc | agaaggagag | ggagagagaa | agagagagag | gctaattaaa | aaaggatact | 120 |
| ccgagggaag | agagcaaggg | cggtgcgccg | ccaaggacca | actagcggcg | gagcttcgat | 180 |
| cttgcctagg | cgcggagagc | tcccaacctg | gctggaacc | ttgcccagca | caggtggctg | 240 |
| ctacacccca | tgtaaaaagc | ggaaaataaa | atgaagattt | ccagcgcaa | gatgcggtac | 300 |
| tggttgcttc | cacctttttt | ggcaattgtt | tatttctgca | ccattgtcca | aggtcaagtg | 360 |
| gctccaccca | caaggttaag | atataatgta | atatctcatg | acagtataca | gatttcatgg | 420 |
| aaggctccaa | gagggaaatt | tggtggttac | aaacttcttg | tgactccaac | ttcaggtgga | 480 |
| aaaactaacc | agctgaatct | gcagaacact | gcaactaaag | caattattca | aggccttatg | 540 |
| ccagaccaga | attacacagt | tcaaattatt | gcatacaata | aagataaaga | aagcaagcca | 600 |
| gctcaaggcc | aattcagaat | taaagattta | gaaaaaagaa | aggatccaaa | gcccagagtc | 660 |
| aaagttgtgg | acagaggaaa | tgggagtaga | ccatcttcac | cagaagaagt | gaaatttgtc | 720 |
| tgtcaaactc | cagcaattgc | tgacattgta | atcctggtcg | atggttcatg | gagtattgga | 780 |
| agattcaact | tcagactggt | tcggcatttc | ttggaaaacc | tggttacagc | attcgatgtg | 840 |
| ggctcagaga | agacacgaat | tggtcttgca | cagtatagtg | gtgacccag | aatagaatgg | 900 |
| cacttgaatg | catttagcac | aaaagatgaa | gtgattgaag | ctgtccgaaa | cctcccatat | 960 |
| aaaggaggaa | atacactaac | aggtcttgct | ttgaactaca | ttttgaaaa | tagcttcaaa | 1020 |
| ccagaagcag | gatcaaggac | tggagtatcc | aaaattggca | ttttaatcac | agatggaaaa | 1080 |
| tcccaagatg | acattattcc | accatctaga | aatcttcgtg | agtctggtgt | agaactgttt | 1140 |
| gccataggg | tgaaaaacgc | ggatgtgaat | gagctgcagg | agatcgcctc | tgaaccagac | 1200 |
| agcactcatg | tgtacaatgt | tgccgaattc | gatctgatgc | acacagttgt | ggagagtctg | 1260 |
| accaggactc | tctgctctag | agtggaagaa | caggacagaa | aaattaaagc | tcagcccat | 1320 |
| gccatcactg | ggccgcctac | ggagttgatt | acttctgaag | tcactgccag | aagctttatg | 1380 |
| gttaactgga | ctcatgcccc | aggaaatgtg | gaaaaataca | gagttgtgta | ttatcctacc | 1440 |
| agggtggaa | aaccagacga | ggtggtggta | gatggaactg | tatcttccac | agtgttgaaa | 1500 |
| aacttgatgt | ctttaactga | atatcagata | gcagtctttg | caatctatgc | ccacactgct | 1560 |
| agtgaaggcc | tacggggaac | tgaaactaca | cttgctttac | cgatggcttc | tgaccttcta | 1620 |
| ctgtacgacg | tgactgagaa | cagcatgcga | gtcaaatggg | atgcagtgcc | tgggccctca | 1680 |
| ggttacctga | tcctttatgc | tcctctaaca | gagggcctgg | ctgggatga | aaagagatg | 1740 |
| aaaattggag | agacccacac | agatattgaa | ttgagtgggt | tgttgcccaa | tacagaatac | 1800 |
| acagtcacag | tttatgccat | gtttggagaa | gaggccagtg | atcctgttac | gggacaagaa | 1860 |
| acaacattgg | ctttaagtcc | accaagaaac | ctgagaatct | ccaatgttgg | ctctaacagt | 1920 |

```
gctcgattaa cctgggaccc aacttcaaga cagatcaatg gttatcgaat tgtatataac    1980
aatgcagatg ggactgaaat caatgaggtt gaagtcgatc ctattactac cttccctctg    2040
aagggcttga cacctctcac agagtatact attgctattt tctccatcta tgatgaagga    2100
cagtcagagc ctctgactgg agttttacc accgaggaag ttccagccca gcaatactta     2160
gaaattgatg aggtgacgac agacagtttt agggtgacct ggcatcccct ctcagctgat    2220
gaagggctac acaaattgat gtggattcca gtctatgggg ggaagactga ggaggttgtc    2280
ctgaaagaag agcaggactc acatgttatt gaaggcctgg agcccggtac ggagtatgaa    2340
gtttcactat tggccgtact tgatgatgga agcgagagtg aggtggtgac tgctgtcggg    2400
accacacttg acagtttttg gacagaacca gctacaacca tagtgcctac cacatctgtg    2460
acttcagttt tccagacggg aatcagaaac ctagttgtag gtgatgaaac tacttctagc    2520
ctgcgggtaa atgggacat ttctgacagc gatgtgcagc agtttagggt gacctacatg     2580
acagctcaag ggaccctga ggaagaagtc ataggaacgg ttatggtgcc tggaagccag     2640
aacaacctcc ttctgaagcc tctgcttcct gatactgaat acaaagtcac agtgactccc    2700
atctacacgg atggcgaagg cgtcagcgtc tccgctcctg aaaaaccttt accatcctcg    2760
gggccccaga acttgcgggt gtccgaggaa tggtataacc ggttgcgcat tacgtgggac    2820
cccccatctt ccccggtgaa aggctataga attgtctaca aacctgtcag tgttcctggt    2880
ccaacactgg aaacgtttgt gggagctgac attaacacca tccttatcac aaacctcctc    2940
agcggaatgg actacaatgt gaagatattt gcctcccagg cctcaggctt cagcgacgcc    3000
ctgacaggca tggtgaaaac attgttcttg ggtgttacca atctccaagc caaacatgtt    3060
gaaatgacca gcttgtgtgc ccactggcag gtacatcgcc atgccacagc ctatagggtt    3120
gttatagaat ccctccagga taggcaaaag caagaatcca ctgtgggtgg agggacaacc    3180
aggcattgct tctatggact tcagcctgat tctgaatata aaatcagtgt ttatacaaag    3240
ctccaggaga ttgaaggacc tagtgtgagc ataatggaaa aaacacaatc acttcctaca    3300
cgaccaccaa cttttcctcc aaccattcca ccagcaaaag agtatgtaa ggcggccaag     3360 gctgacctgg tatttatggt ggatggatcc tggagcattg gagatgaaaa tttcaataag    3420
atcatcagct ttctatacag cactgttgga gccctgaaca agattggcac agatggaacc    3480
caagttgcaa tggttcagtt cactgatgat cccagaacag aatttaaact aaatgcttac    3540
aaaaccaaag agactcttct tgatgcaatt aaacacattt catacaaagg aggaaataca    3600
aaaacaggaa aagcaattaa gtatgttcga gataccttgt tcactgcaga gtcaggtaca    3660
agaaggggca tcccaaaggt tatcgtggtt ataactgatg gaagatcaca agatgatgtg    3720
aacaaaatct ccagggagat gcaattagat ggctatagca ttttgcaat tggtgtggcc     3780 gatgcagatt actcggagtt ggttagcatt ggcagtaagc ccagcgcacg ccatgtcttc    3840
tttgtggatg actttgacgc ctttaagaaa atcgaagatg agttaattac ttttgtctgc    3900
gaaacagcat cagcaacctg tccagtggta cacaaggatg gcattgatct tgcaggattt    3960
aagatgatgg aaatgtttgg tttggttgaa aaagattttt catcagtgga aggggtttct    4020
atggagcctg taccttcaa tgtgtttcca tgttaccaac tccataaaga tgccctggtt     4080
tcccagccaa ccaggtactt gcacccagaa ggattgccct ccgactacac aatcagtttt    4140
ctattccgga ttcttcctga cactccacag gagccatttg ctctttggga gattttaaat    4200
aaaaattctg acccattggt tggggttatt ttagacaatg gtgggaaaac tctaacatat    4260
ttcaactatg accagagtgg ggattttcaa actgttactt tcgaaggacc tgaaattagg    4320
```

```
aaaattttt  atggaagctt  tcacaagcta  cacattgttg  tcagtgagac  tttggtcaaa      4380
gtggttattg  actgcaagca  agtgggtgag  aaggcaatga  acgcatcagc  taatatcacg      4440
tcagatggtg  tagaagtgct  agggaaaatg  gttcgatcaa  gaggaccagg  tggaaactct      4500
gcaccgttcc  agttacagat  gtttgatatt  gtttgctcca  catcatgggc  caatacagac      4560
aaatgctgtg  aacttccagg  cctgagagat  gatgagtctt  gcccagacct  tccccattcc      4620
tgctcctgtt  ctgaaaccaa  tgaagtggct  ctgggaccag  cgggcccacc  aggtggtcca      4680
ggactccgag  gaccaaaggg  ccagcaaggt  gaaccgggtc  caaagggacc  agatggccct      4740
cggggtgaaa  ttggtctgcc  aggacctcag  ggtccacctg  gacctcaagg  accaagtggt      4800
ctgtccattc  aaggaatgcc  cggaatgcca  ggagaaaaag  gagagaaagg  agatactggc      4860
cttccaggtc  cacagggtat  cccaggaggc  gttggttcac  caggacgtga  tggctcacca      4920
ggccagaggg  gccttccggg  aaaggatgga  tcctcgggac  ctccaggacc  accagggcca      4980
ataggcattc  ctggcacccc  tggagtccca  gggatcacag  gaagcatggg  accgcaaggc      5040
gccctgggac  cacctggtgt  ccctggagca  aggggggaac  gaggagagcg  gggtgacctg      5100
cagtctcaag  ccatggtgag  atcagtgcg  cgtcaagtat  gcgaacagct  catccagagt      5160
cacatggcca  ggtacactgc  catcctcaac  cagattccca  gccactcctc  atccatccgg      5220
actgtccaag  ggcctcctgg  ggagcctggg  aggccaggct  cacctggagc  ccctggtgaa      5280
caaggacccc  caggcacacc  aggcttcccc  ggaaatgcag  gcgtgccagg  accccagga      5340 gaacgaggtc  taactggtat  caaaggagaa  aaaggaaatc  caggcgttgg  aacccaaggt      5400
ccaagaggcc  ccctggacc  agcaggacct  tcaggggaga  gtcggcctgg  cagccctggg      5460
ccccctggct  ctcctggacc  aagaggccca  ccaggtcatc  tggggttcc  tggaccccaa      5520 ggtccttctg  gccagcctgg  atattgtgac  ccctcatcat  gttctgccta  tggtgtgaga      5580
gctccccatc  cagatcagcc  agagttcacc  cctgtccaag  atgagctgga  agccatggaa      5640
ctgtggggcc  ctggagtctg  atagcctcag  gagaaatttg  aagaccaact  gcaagaactc      5700
ttaaggaatc  ttgtttgaga  aaatgttgtt  atgtggtttg  tatgctactt  ttgggggca      5760 gggctcattt  cagcagccta  aatctcctcc  ttggataatg  ttaatattat  tattattatt      5820
aacaaaaaat  atatatttt  aaaaagttcc  cttaatctat  gacatggtag  caatgatttc      5880
cctttggtgt  cttaatggca  tgtcagataa  tttgttttc  cagagaagag  agctcaaaga      5940
ggaattggga  aaaataaatt  gaactctgga  atcttctctc  tcaagtccta  aaatgaacaa      6000
acagatatga  ttgtgtttga  gggaaatatg  tccctagcag  gaaaagaatt  caagagggtt      6060
caaagaatat  gtcacttact  cctacttgct  gtaggaataa  ccttgctgat  aagaaaaaaa      6120
gggacaatat  tggagaaact  acctcttgtt  taattgatct  gtccaactct  gagatcactt      6180
ggtaactggt  ttcatgtgta  tccaaaaatc  agcatttgga  tttaagcttt  ctgaatttgg      6240
tagtttaaga  aacagattta  gttttcagt  ggttttaact  catgtgaaat  aatgattttc      6300
caccagctct  gatgcaaaga  gatataattt  taatgaacga  tttatccagc  agtgtgttcc      6360 agggggttgcc  tctccttatc  tacggggatt  actttgtaca  tgcagataag  ttttcgcaaa      6420
cctatttcca  ttttcttttg  taagcaaata  aactttaaa  acaa                        6464
```

<210> SEQ ID NO 4
<211> LENGTH: 1796
<212> TYPE: PRT
<213> ORGANISM: Homo sapiens

```
<400> SEQUENCE: 4

Met Lys Ile Phe Gln Arg Lys Met Arg Tyr Trp Leu Leu Pro Pro Phe
1               5                   10                  15

Leu Ala Ile Val Tyr Phe Cys Thr Ile Val Gln Gly Gln Val Ala Pro
            20                  25                  30

Pro Thr Arg Leu Arg Tyr Asn Val Ile Ser His Asp Ser Ile Gln Ile
        35                  40                  45

Ser Trp Lys Ala Pro Arg Gly Lys Phe Gly Tyr Lys Leu Leu Val
    50                  55                  60

Thr Pro Thr Ser Gly Gly Lys Thr Asn Gln Leu Asn Leu Gln Asn Thr
65                  70                  75                  80

Ala Thr Lys Ala Ile Ile Gln Gly Leu Met Pro Asp Gln Asn Tyr Thr
                85                  90                  95

Val Gln Ile Ile Ala Tyr Asn Lys Asp Lys Glu Ser Lys Pro Ala Gln
            100                 105                 110

Gly Gln Phe Arg Ile Lys Asp Leu Glu Lys Arg Lys Asp Pro Lys Pro
        115                 120                 125

Arg Val Lys Val Val Asp Arg Gly Asn Gly Ser Arg Pro Ser Ser Pro
130                 135                 140

Glu Glu Val Lys Phe Val Cys Gln Thr Pro Ala Ile Ala Asp Ile Val
145                 150                 155                 160

Ile Leu Val Asp Gly Ser Trp Ser Ile Gly Arg Phe Asn Phe Arg Leu
                165                 170                 175

Val Arg His Phe Leu Glu Asn Leu Val Thr Ala Phe Asp Val Gly Ser
            180                 185                 190

Glu Lys Thr Arg Ile Gly Leu Ala Gln Tyr Ser Gly Asp Pro Arg Ile
        195                 200                 205

Glu Trp His Leu Asn Ala Phe Ser Thr Lys Asp Glu Val Ile Glu Ala
210                 215                 220

Val Arg Asn Leu Pro Tyr Lys Gly Gly Asn Thr Leu Thr Gly Leu Ala
225                 230                 235                 240

Leu Asn Tyr Ile Phe Glu Asn Ser Phe Lys Pro Glu Ala Gly Ser Arg
                245                 250                 255

Thr Gly Val Ser Lys Ile Gly Ile Leu Ile Thr Asp Gly Lys Ser Gln
            260                 265                 270

Asp Asp Ile Ile Pro Pro Ser Arg Asn Leu Arg Glu Ser Gly Val Glu
        275                 280                 285

Leu Phe Ala Ile Gly Val Lys Asn Ala Asp Val Asn Glu Leu Gln Glu
        290                 295                 300

Ile Ala Ser Glu Pro Asp Ser Thr His Val Tyr Asn Val Ala Glu Phe
305                 310                 315                 320

Asp Leu Met His Thr Val Glu Ser Leu Thr Arg Thr Leu Cys Ser
                325                 330                 335

Arg Val Glu Glu Gln Asp Arg Gly Ile Lys Ala Ser Ala His Ala Ile
            340                 345                 350

Thr Gly Pro Pro Thr Glu Leu Ile Thr Ser Glu Val Thr Ala Arg Ser
        355                 360                 365

Phe Met Val Asn Trp Thr His Ala Pro Gly Asn Val Glu Lys Tyr Arg
370                 375                 380

Val Val Tyr Tyr Pro Thr Arg Gly Gly Lys Pro Asp Glu Val Val Val
385                 390                 395                 400

Asp Gly Thr Val Ser Ser Thr Val Leu Lys Asn Leu Met Ser Leu Thr
                405                 410                 415
```

```
Glu Tyr Gln Ile Ala Val Phe Ala Ile Tyr Ala His Thr Ala Ser Glu
            420                 425                 430

Gly Leu Arg Gly Thr Glu Thr Leu Ala Leu Pro Met Ala Ser Asp
        435                 440                 445

Leu Leu Leu Tyr Asp Val Thr Glu Asn Ser Met Arg Val Lys Trp Asp
450                 455                 460

Ala Val Pro Gly Ala Ser Gly Tyr Leu Ile Leu Tyr Ala Pro Leu Thr
465                 470                 475                 480

Glu Gly Leu Ala Gly Asp Glu Lys Glu Met Lys Ile Gly Glu Thr His
                485                 490                 495

Thr Asp Ile Glu Leu Ser Gly Leu Leu Pro Asn Thr Glu Tyr Thr Val
                500                 505                 510

Thr Val Tyr Ala Met Phe Gly Glu Glu Ala Ser Asp Pro Val Thr Gly
            515                 520                 525

Gln Glu Thr Thr Leu Ala Leu Ser Pro Pro Arg Asn Leu Arg Ile Ser
        530                 535                 540

Asn Val Gly Ser Asn Ser Ala Arg Leu Thr Trp Asp Pro Thr Ser Arg
545                 550                 555                 560

Gln Ile Asn Gly Tyr Arg Ile Val Tyr Asn Asn Ala Asp Gly Thr Glu
                565                 570                 575

Ile Asn Glu Val Glu Val Asp Pro Ile Thr Thr Phe Pro Leu Lys Gly
            580                 585                 590

Leu Thr Pro Leu Thr Glu Tyr Thr Ile Ala Ile Phe Ser Ile Tyr Asp
        595                 600                 605

Glu Gly Gln Ser Glu Pro Leu Thr Gly Val Phe Thr Thr Glu Glu Val
610                 615                 620

Pro Ala Gln Gln Tyr Leu Glu Ile Asp Glu Val Thr Thr Asp Ser Phe
625                 630                 635                 640

Arg Val Thr Trp His Pro Leu Ser Ala Asp Glu Gly Leu His Lys Leu
                645                 650                 655

Met Trp Ile Pro Val Tyr Gly Gly Lys Thr Glu Glu Val Val Leu Lys
            660                 665                 670

Glu Glu Gln Asp Ser His Val Ile Glu Gly Leu Glu Pro Gly Thr Glu
        675                 680                 685

Tyr Glu Val Ser Leu Leu Ala Val Leu Asp Asp Gly Ser Glu Ser Glu
    690                 695                 700

Val Val Thr Ala Val Gly Thr Thr Leu Asp Ser Phe Trp Thr Glu Pro
705                 710                 715                 720

Ala Thr Thr Ile Val Pro Thr Thr Ser Val Thr Ser Val Phe Gln Thr
                725                 730                 735

Gly Ile Arg Asn Leu Val Val Gly Asp Glu Thr Thr Ser Ser Leu Arg
            740                 745                 750

Val Lys Trp Asp Ile Ser Asp Ser Asp Val Gln Gln Phe Arg Val Thr
        755                 760                 765

Tyr Met Thr Ala Gln Gly Asp Pro Glu Glu Glu Val Ile Gly Thr Val
    770                 775                 780

Met Val Pro Gly Ser Gln Asn Asn Leu Leu Leu Lys Pro Leu Leu Pro
785                 790                 795                 800

Asp Thr Glu Tyr Lys Val Thr Val Thr Pro Ile Tyr Thr Asp Gly Glu
                805                 810                 815

Gly Val Ser Val Ser Ala Pro Gly Lys Thr Leu Pro Ser Ser Gly Pro
            820                 825                 830
```

-continued

```
Gln Asn Leu Arg Val Ser Glu Glu Trp Tyr Asn Arg Leu Arg Ile Thr
            835                 840                 845
Trp Asp Pro Ser Ser Pro Val Lys Gly Tyr Arg Ile Val Tyr Lys
850                 855                 860
Pro Val Ser Val Pro Gly Pro Thr Leu Glu Thr Phe Val Gly Ala Asp
865                 870                 875                 880
Ile Asn Thr Ile Leu Ile Thr Asn Leu Leu Ser Gly Met Asp Tyr Asn
            885                 890                 895
Val Lys Ile Phe Ala Ser Gln Ala Ser Gly Phe Ser Asp Ala Leu Thr
                900                 905                 910
Gly Met Val Lys Thr Leu Phe Leu Gly Val Thr Asn Leu Gln Ala Lys
            915                 920                 925
His Val Glu Met Thr Ser Leu Cys Ala His Trp Gln Val His Arg His
    930                 935                 940
Ala Thr Ala Tyr Arg Val Val Ile Glu Ser Leu Gln Asp Arg Gln Lys
945                 950                 955                 960
Gln Glu Ser Thr Val Gly Gly Thr Thr Arg His Cys Phe Tyr Gly
                965                 970                 975
Leu Gln Pro Asp Ser Glu Tyr Lys Ile Ser Val Tyr Thr Lys Leu Gln
            980                 985                 990
Glu Ile Glu Gly Pro Ser Val Ser  Ile Met Glu Lys Thr  Gln Ser Leu
            995                 1000                1005
Pro Thr  Arg Pro Pro Thr Phe  Pro Pro Thr Ile Pro  Pro Ala Lys
    1010                1015                1020
Glu Val  Cys Lys Ala Ala Lys  Ala Asp Leu Val Phe  Met Val Asp
    1025                1030                1035
Gly Ser  Trp Ser Ile Gly Asp  Glu Asn Phe Asn Lys  Ile Ile Ser
    1040                1045                1050
Phe Leu  Tyr Ser Thr Val Gly  Ala Leu Asn Lys Ile  Gly Thr Asp
    1055                1060                1065
Gly Thr  Gln Val Ala Met Val  Gln Phe Thr Asp Asp  Pro Arg Thr
    1070                1075                1080
Glu Phe  Lys Leu Asn Ala Tyr  Lys Thr Lys Glu Thr  Leu Leu Asp
    1085                1090                1095
Ala Ile  Lys His Ile Ser Tyr  Lys Gly Gly Asn Thr  Lys Thr Gly
    1100                1105                1110
Lys Ala  Ile Lys Tyr Val Arg  Asp Thr Leu Phe Thr  Ala Glu Ser
    1115                1120                1125
Gly Thr  Arg Arg Gly Ile Pro  Lys Val Ile Val Val  Ile Thr Asp
    1130                1135                1140
Gly Arg  Ser Gln Asp Asp Val  Asn Lys Ile Ser Arg  Glu Met Gln
    1145                1150                1155
Leu Asp  Gly Tyr Ser Ile Phe  Ala Ile Gly Val Ala  Asp Ala Asp
    1160                1165                1170
Tyr Ser  Glu Leu Val Ser Ile  Gly Ser Lys Pro Ser  Ala Arg His
    1175                1180                1185
Val Phe  Phe Val Asp Asp Phe  Asp Ala Phe Lys Lys  Ile Glu Asp
    1190                1195                1200
Glu Leu  Ile Thr Phe Val Cys  Glu Thr Ala Ser Ala  Thr Cys Pro
    1205                1210                1215
Val Val  His Lys Asp Gly Ile  Asp Leu Ala Gly Phe  Lys Met Met
    1220                1225                1230
Glu Met  Phe Gly Leu Val Glu  Lys Asp Phe Ser Ser  Val Glu Gly
```

-continued

```
            1235                1240                1245
Val Ser Met Glu Pro Gly Thr Phe Asn Val Phe Pro Cys Tyr Gln
    1250                1255                1260
Leu His Lys Asp Ala Leu Val Ser Gln Pro Thr Arg Tyr Leu His
    1265                1270                1275
Pro Glu Gly Leu Pro Ser Asp Tyr Thr Ile Ser Phe Leu Phe Arg
    1280                1285                1290
Ile Leu Pro Asp Thr Pro Gln Glu Pro Phe Ala Leu Trp Glu Ile
    1295                1300                1305
Leu Asn Lys Asn Ser Asp Pro Leu Val Gly Val Ile Leu Asp Asn
    1310                1315                1320
Gly Gly Lys Thr Leu Thr Tyr Phe Asn Tyr Asp Gln Ser Gly Asp
    1325                1330                1335
Phe Gln Thr Val Thr Phe Glu Gly Pro Glu Ile Arg Lys Ile Phe
    1340                1345                1350
Tyr Gly Ser Phe His Lys Leu His Ile Val Val Ser Glu Thr Leu
    1355                1360                1365
Val Lys Val Val Ile Asp Cys Lys Gln Val Gly Glu Lys Ala Met
    1370                1375                1380
Asn Ala Ser Ala Asn Ile Thr Ser Asp Gly Val Glu Val Leu Gly
    1385                1390                1395
Lys Met Val Arg Ser Arg Gly Pro Gly Gly Asn Ser Ala Pro Phe
    1400                1405                1410
Gln Leu Gln Met Phe Asp Ile Val Cys Ser Thr Ser Trp Ala Asn
    1415                1420                1425
Thr Asp Lys Cys Cys Glu Leu Pro Gly Leu Arg Asp Asp Glu Ser
    1430                1435                1440
Cys Pro Asp Leu Pro His Ser Cys Ser Cys Ser Glu Thr Asn Glu
    1445                1450                1455
Val Ala Leu Gly Pro Ala Gly Pro Pro Gly Gly Pro Gly Leu Arg
    1460                1465                1470
Gly Pro Lys Gly Gln Gln Gly Glu Pro Gly Pro Lys Gly Pro Asp
    1475                1480                1485
Gly Pro Arg Gly Glu Ile Gly Leu Pro Gly Pro Gln Gly Pro Pro
    1490                1495                1500
Gly Pro Gln Gly Pro Ser Gly Leu Ser Ile Gln Gly Met Pro Gly
    1505                1510                1515
Met Pro Gly Glu Lys Gly Glu Lys Gly Asp Thr Gly Leu Pro Gly
    1520                1525                1530
Pro Gln Gly Ile Pro Gly Gly Val Gly Ser Pro Gly Arg Asp Gly
    1535                1540                1545
Ser Pro Gly Gln Arg Gly Leu Pro Gly Lys Asp Gly Ser Ser Gly
    1550                1555                1560
Pro Pro Gly Pro Pro Gly Pro Ile Gly Ile Pro Gly Thr Pro Gly
    1565                1570                1575
Val Pro Gly Ile Thr Gly Ser Met Gly Pro Gln Gly Ala Leu Gly
    1580                1585                1590
Pro Pro Gly Val Pro Gly Ala Lys Gly Glu Arg Gly Glu Arg Gly
    1595                1600                1605
Asp Leu Gln Ser Gln Ala Met Val Arg Ser Val Ala Arg Gln Val
    1610                1615                1620
Cys Glu Gln Leu Ile Gln Ser His Met Ala Arg Tyr Thr Ala Ile
    1625                1630                1635
```

```
Leu Asn Gln Ile Pro Ser His Ser Ser Ile Arg Thr Val Gln
    1640            1645                1650

Gly Pro Pro Gly Glu Pro Gly Arg Pro Gly Ser Pro Gly Ala Pro
1655                1660                1665

Gly Glu Gln Gly Pro Pro Gly Thr Pro Gly Phe Pro Gly Asn Ala
    1670                1675                1680

Gly Val Pro Gly Thr Pro Gly Glu Arg Gly Leu Thr Gly Ile Lys
1685                1690                1695

Gly Glu Lys Gly Asn Pro Gly Val Gly Thr Gln Gly Pro Arg Gly
    1700                1705                1710

Pro Pro Gly Pro Ala Gly Pro Ser Gly Glu Ser Arg Pro Gly Ser
1715                1720                1725

Pro Gly Pro Pro Gly Ser Pro Gly Pro Arg Gly Pro Pro Gly His
    1730                1735                1740

Leu Gly Val Pro Gly Pro Gln Gly Pro Ser Gly Gln Pro Gly Tyr
1745                1750                1755

Cys Asp Pro Ser Ser Cys Ser Ala Tyr Gly Val Arg Ala Pro His
    1760                1765                1770

Pro Asp Gln Pro Glu Phe Thr Pro Val Gln Asp Glu Leu Glu Ala
1775                1780                1785

Met Glu Leu Trp Gly Pro Gly Val
    1790                1795

<210> SEQ ID NO 5
<211> LENGTH: 5008
<212> TYPE: DNA
<213> ORGANISM: Homo sapiens

<400> SEQUENCE: 5
aagtaccaag gtctgcggca ggaggagacc ggctcacagg agcagcagca ttggaagagg    60
cacccagcag cctcccaggc atcctggagg gtctgctccc tgtctttcca aggatgagtc   120
tccaggagat gttccgcttc cctatggggc tcctgcttgg ctctgtgctc ctggtggctt   180
cggccccagc cactctggag cctcccggct gcagcaacaa ggagcaacag gtcactgtca   240
gccacaccta caagatcgat gtgcccaagt ctgccttggt tcaggttgac gctgaccctc   300
agcccctcag tgacgatggg gcttcgctct tggccctggg ggaggccagg aggaacagaa   360
acatcatctt caggcacaac atccgccttc agacgccaca gaaggactgc gagttggcag   420
gcagtgtcca ggacctcctg gcccgggtga agaagctgga ggaagagatg gtggagatga   480
aggaacagtg tagtgcccag cgctgctgcc agggagtcac tgatctaagc cgccactgca   540
gcggccacgg gaccttctcc ctggagacct gcagctgcca ctgcgaagag gcagggagg   600 gccccgcctg cgagcggctg gcctgccccg gggcgtgcag cggccacggg cgttgcgtgg   660 acggcgctg cctgtgccat gagccctacg tgggtgccga ctgcggctac ccggcctgcc   720
ctgagaactg cagcggacac ggcgagtgcg tgcgcggcgt gtgccagtgc acgaagact   780 tcatgtcgga ggactgcagc gagaagcgct gtcccggcga ctgcagcggc acggcttct   840 gtgacacggg cgagtgctac tgcgaggagg gcttcacagg cctggactgt gcccaggtgg   900 tcacccccaca gggcctgcag ctgctcaaga cacggagga ttctctgctg gtgagctggg   960
agccctccag ccaggtggat cactacctcc tcagctacta ccccctgggg aaggagctct  1020
ctgggaagca gatccaagtg cccaaggagc agcacagcta tgagattctt ggttgctgc  1080 ctggaaccaa gtacatagtc accctgcgta acgtcaagaa tgaagtttct agcagcccac  1140
```

```
agcatctact tgccaccaca gaccttgctg tgcttggcac tgcctgggtg acagatgaga   1200
ctgagaactc ccttgacgtg gagtgggaaa acccctcaac tgaggtggac tactacaagc   1260
tgcgatatgg ccccatgaca ggacaggagg tagctgaggt cactgtgccc aagagcagtg   1320
accccaagag ccgatatgac atcactggtc tgcacccggg gactgagtat aagatcacgg   1380
tggtgcccat gagaggagag ctggagggca agccgatcct cctgaatggc aggacagaaa   1440
ttgacagtcc aaccaatgtt gtcactgatc gagtgactga agacacagca actgtctcct   1500
gggacccagt gcaggctgtc atagacaagt atgtagtgcg ctacacttct gctgatgggg   1560
acaccaagga aatggcagtg cacaaggatg agagcagcac tgtcctgacg ggcctgaagc   1620
caggagaggc atacaaggtc tacgtgtggg ctgaaagggg caaccagggg agcaagaaag   1680
ctgacaccaa tgccctcaca gaaattgaca gcccagcaaa cctggtgact gaccgggtga   1740
ctgagaatac cgccaccatc tcctgggacc cggtacaggc caccattgac aagtacgtgg   1800
tgcgctacac ctctgctgac gaccaagaga ccagagaggt tctggtgggg aaggagcaga   1860
gcagcactgt cctgacaggc ctgaggccag gtgtggagta cacagtgcat gtctgggccc   1920
agaaggggga ccgagagagc aagaaggctg acaccaacgc cccgacagat attgacagcc   1980
ccaaaaacct ggtgactgac cgggtgacag agaatatggc cacggtctcc tgggacccgg   2040
tgcaggccgc cattgacaag tacgtggtgc gctacacctc tgctggtgga gagaccaggg   2100
aggttccggt ggggaaggag cagagcagca cagtcctgac aggcctgaga ccgggtatgg   2160
agtacatggt gcacgtgtgg gcccagaagg gggaccagga gagcaagaag gccgacacca   2220
aggcccagac agacattgac agcccccaaa acctggtgac cgaccgggtg acagagaata   2280
tggccactgt ctcctgggac ccggtgcggg ccaccattga caggtatgtg gtgcgctaca   2340
cctctgccaa ggacggagag accagggagg ttccggtggg gaaggagcag agtagcactg   2400
tcctgacggg cctgaggccg ggtgtggagt acacggtgca cgtgtgggcc agaagggggc   2460
cccaggagag caagaaggct gacaccaagg cccagacaga cattgacagc ccccaaaacc   2520
tggtcactga ctgggtgaca gagaatacag ccactgtctc ctgggacccg gtgcaggcca   2580
ccattgacag gtatgtggtg cactacacgt ctgccaacgg agagaccagg gaggttccag   2640
tggggaagga gcagagcagc actgtcctga cgggcctgag gccgggcatg gagtacacgg   2700
tgcacgtgtg ggcccagaag gggaaccagg agagcaagaa ggctgacacc aaggcccaga   2760
cagaaattga cggcccccaaa aacctagtga ctgactgggt gacggagaat atggccactg   2820
tctcctggga cccggttcag gccaccattg acaagtacat ggtgcgctac acctctgctg   2880
acggagagac cagggaggtt ccggtgggga aggagcacag cagcactgtc ctgacgggcc   2940
tgagaccagg catggagtac atggtgcacg tgtgggccca aaggggggcc aggagagca   3000 agaaggctga caccaaggcc cagacagaac tcgaccctcc cagaaacctt cgtccatctg   3060
ctgtaacgca gtctggtggc atattgacct ggacgccccc ctctgctcag atccacggct   3120
acattctgac ttaccagttc ccagatggca cagttaagga gatgcagctg ggacgggaag   3180
accagaggtt tgcgttgcaa ggccttgagc aaggcgccac ctaccctgtc tcccttgttg   3240 ccttttaaggg tggtcgccgg agcagaaatg tatccaccac cctctccaca gttggtgccc   3300
gtttcccaca cccttcggac tgcagtcagg ttcagcagaa cagcaatgcc gccagtggtc   3360
tgtacaccat ctacctgcat ggcgatgcca gccggcccct gcaggtgtac tgtgacatgg   3420
aaacggacgg aggtggctgg attgtcttcc agaggcggaa cactgggcag ctggatttct   3480
```

-continued

| | |
|---|---|
| tcaagcgatg gaggagctat gtggaaggct ttggggaccc catgaaggag ttctggcttg | 3540 |
| gacttgacaa gctacacaac ctcaccaccg gcactccagc gcggtatgag gtgagagtgg | 3600 |
| atttacagac tgccaatgaa tctgcctatg ctatatatga tttcttccaa gtggcctcca | 3660 |
| gcaaggagcg gtataagctg acagttggga aatacagagg cacggcaggg gatgctctta | 3720 |
| cttaccacaa tggatggaag tttacaactt ttgacagaga caatgatatc gcactcagca | 3780 |
| actgtgccct gacacatcat ggtggctggt ggtataagaa ctgccacttg gccaacccta | 3840 |
| atggcagata tggggagacc aagcacagtg aggggggtgaa ctgggagcct tggaaaggac | 3900 |
| atgaattctc cattccttac gtggagttga aaatccgccc tcatggctac agcagggagc | 3960 |
| ctgtcctggg cagaaagaag cggacgctga gaggaaggct gcgaacgttc tgatggcccg | 4020 |
| tgtgagcagt cctcgcagga gacaccacca gctgtggcag cttggggcgg ggtgggtagt | 4080 |
| ggtcactgcg gtctgggagt gctcagatag cccgcagaac aaatcatgtc accaagcttc | 4140 |
| aagccatgga ggttccttcc ctctcacctg catttttgcc cgtctttatg agggtcttga | 4200 |
| aaatcaaaat agtagttgca cagtatgtgt aggaaagaca gtactggaac ggcaaggttt | 4260 |
| ctcagcttat cttcagcaac atatatactg gattagggca agagaaggaa tcacccagca | 4320 |
| cttcaccagt tggaaatctc tggaaattta catctatgta tttaaagttc tgctaatgca | 4380 |
| aatcttttct ctggaaagaa gcacagagga ggagttctga tgacccaggg gttagggctg | 4440 |
| agacaaccgg acgtttgtca cctcctttcc cattgggttt ttaggaaaac agtgtgaacc | 4500 |
| tccccctttt aatttctggt gttatgagga agaataaagg ggataaaagg ggctaagatg | 4560 |
| gactcatgtt tagctaagtt ctgacttgta tccagcatgc tggagaccaa agctgccgcc | 4620 |
| ttactgctat ttttaagtgc cctcttttca gtcatttgca taattgcgtc catagagctg | 4680 |
| catatgttgt gaataaattc tcactcattt caactttgaa taatttgact gtcttgataa | 4740 |
| ttggttcctc ccaaagactc ttctgcaact cccattcatg cccaccaggc ctcagactcc | 4800 |
| ctcttttccc cgccctgcac tattggagcc ctgggttttg tgggagtgct cagcaccgtg | 4860 |
| agtcttactg tttgatcgga cagttagcaa gatcagatcc tttttgctta ttttctatca | 4920 |
| ctttggaggg ttttctgtag caaaatcagt gaccaatgaa gtaacttaaa ttcctattga | 4980 |
| agaaaaaaaa taataaacca cttgattt | 5008 |

<210> SEQ ID NO 6
<211> LENGTH: 1299
<212> TYPE: PRT
<213> ORGANISM: Homo sapiens

<400> SEQUENCE: 6

Met Ser Leu Gln Glu Met Phe Arg Phe Pro Met Gly Leu Leu Leu Gly
1               5                   10                  15

Ser Val Leu Leu Val Ala Ser Ala Pro Ala Thr Leu Glu Pro Pro Gly
            20                  25                  30

Cys Ser Asn Lys Glu Gln Gln Val Thr Val Ser His Thr Tyr Lys Ile
        35                  40                  45

Asp Val Pro Lys Ser Ala Leu Val Gln Val Asp Ala Asp Pro Gln Pro
    50                  55                  60

Leu Ser Asp Asp Gly Ala Ser Leu Leu Ala Leu Gly Glu Ala Arg Glu
65                  70                  75                  80

Glu Gln Asn Ile Ile Phe Arg His Asn Ile Arg Leu Gln Thr Pro Gln
                85                  90                  95

Lys Asp Cys Glu Leu Ala Gly Ser Val Gln Asp Leu Leu Ala Arg Val

-continued

```
                100                 105                 110
Lys Lys Leu Glu Glu Glu Met Val Glu Met Lys Glu Gln Cys Ser Ala
            115                 120                 125

Gln Arg Cys Cys Gln Gly Val Thr Asp Leu Ser Arg His Cys Ser Gly
            130                 135                 140

His Gly Thr Phe Ser Leu Glu Thr Cys Ser His Cys Glu Glu Gly
145                 150                 155                 160

Arg Glu Gly Pro Ala Cys Glu Arg Leu Ala Cys Pro Gly Ala Cys Ser
                165                 170                 175

Gly His Gly Arg Cys Val Asp Gly Arg Cys Leu Cys His Glu Pro Tyr
            180                 185                 190

Val Gly Ala Asp Cys Gly Tyr Pro Ala Cys Pro Glu Asn Cys Ser Gly
            195                 200                 205

His Gly Glu Cys Val Arg Gly Val Cys Gln Cys His Glu Asp Phe Met
            210                 215                 220

Ser Glu Asp Cys Ser Glu Lys Arg Cys Pro Gly Asp Cys Ser Gly His
225                 230                 235                 240

Gly Phe Cys Asp Thr Gly Glu Cys Tyr Cys Glu Glu Gly Phe Thr Gly
                245                 250                 255

Leu Asp Cys Ala Gln Val Val Thr Pro Gln Gly Leu Gln Leu Leu Lys
            260                 265                 270

Asn Thr Glu Asp Ser Leu Leu Val Ser Trp Glu Pro Ser Ser Gln Val
            275                 280                 285

Asp His Tyr Leu Leu Ser Tyr Tyr Pro Leu Gly Lys Glu Leu Ser Gly
            290                 295                 300

Lys Gln Ile Gln Val Pro Lys Glu Gln His Ser Tyr Glu Ile Leu Gly
305                 310                 315                 320

Leu Leu Pro Gly Thr Lys Tyr Ile Val Thr Leu Arg Asn Val Lys Asn
                325                 330                 335

Glu Val Ser Ser Pro Gln His Leu Leu Ala Thr Thr Asp Leu Ala
            340                 345                 350

Val Leu Gly Thr Ala Trp Val Thr Asp Glu Thr Glu Asn Ser Leu Asp
            355                 360                 365

Val Glu Trp Glu Asn Pro Ser Thr Glu Val Asp Tyr Tyr Lys Leu Arg
            370                 375                 380

Tyr Gly Pro Met Thr Gly Gln Glu Val Ala Glu Val Thr Val Pro Lys
385                 390                 395                 400

Ser Ser Asp Pro Lys Ser Arg Tyr Asp Ile Thr Gly Leu His Pro Gly
                405                 410                 415

Thr Glu Tyr Lys Ile Thr Val Val Pro Met Arg Gly Glu Leu Glu Gly
            420                 425                 430

Lys Pro Ile Leu Leu Asn Gly Arg Thr Glu Ile Asp Ser Pro Thr Asn
            435                 440                 445

Val Val Thr Asp Arg Val Thr Glu Asp Thr Ala Thr Val Ser Trp Asp
            450                 455                 460

Pro Val Gln Ala Val Ile Asp Lys Tyr Val Val Arg Tyr Thr Ser Ala
465                 470                 475                 480

Asp Gly Asp Thr Lys Glu Met Ala Val His Lys Asp Glu Ser Ser Thr
                485                 490                 495

Val Leu Thr Gly Leu Lys Pro Gly Glu Ala Tyr Lys Val Tyr Val Trp
            500                 505                 510

Ala Glu Arg Gly Asn Gln Gly Ser Lys Lys Ala Asp Thr Asn Ala Leu
            515                 520                 525
```

```
Thr Glu Ile Asp Ser Pro Ala Asn Leu Val Thr Asp Arg Val Thr Glu
    530                 535                 540

Asn Thr Ala Thr Ile Ser Trp Asp Pro Val Gln Ala Thr Ile Asp Lys
545                 550                 555                 560

Tyr Val Val Arg Tyr Thr Ser Ala Asp Asp Gln Glu Thr Arg Glu Val
            565                 570                 575

Leu Val Gly Lys Glu Gln Ser Ser Thr Val Leu Thr Gly Leu Arg Pro
        580                 585                 590

Gly Val Glu Tyr Thr Val His Val Trp Ala Gln Lys Gly Asp Arg Glu
    595                 600                 605

Ser Lys Lys Ala Asp Thr Asn Ala Pro Thr Asp Ile Asp Ser Pro Lys
610                 615                 620

Asn Leu Val Thr Asp Arg Val Thr Glu Asn Met Ala Thr Val Ser Trp
625                 630                 635                 640

Asp Pro Val Gln Ala Ile Asp Lys Tyr Val Val Arg Tyr Thr Ser
            645                 650                 655

Ala Gly Gly Glu Thr Arg Glu Val Pro Val Gly Lys Glu Gln Ser Ser
            660                 665                 670

Thr Val Leu Thr Gly Leu Arg Pro Gly Met Glu Tyr Met Val His Val
    675                 680                 685

Trp Ala Gln Lys Gly Asp Gln Glu Ser Lys Lys Ala Asp Thr Lys Ala
690                 695                 700

Gln Thr Asp Ile Asp Ser Pro Gln Asn Leu Val Thr Asp Arg Val Thr
705                 710                 715                 720

Glu Asn Met Ala Thr Val Ser Trp Asp Pro Val Arg Ala Thr Ile Asp
            725                 730                 735

Arg Tyr Val Val Arg Tyr Thr Ser Ala Lys Asp Gly Glu Thr Arg Glu
            740                 745                 750

Val Pro Val Gly Lys Glu Gln Ser Ser Thr Val Leu Thr Gly Leu Arg
    755                 760                 765

Pro Gly Val Glu Tyr Thr Val His Val Trp Ala Gln Lys Gly Ala Gln
770                 775                 780

Glu Ser Lys Lys Ala Asp Thr Lys Ala Gln Thr Asp Ile Asp Ser Pro
785                 790                 795                 800

Gln Asn Leu Val Thr Asp Trp Val Thr Glu Asn Thr Ala Thr Val Ser
            805                 810                 815

Trp Asp Pro Val Gln Ala Thr Ile Asp Arg Tyr Val Val His Tyr Thr
            820                 825                 830

Ser Ala Asn Gly Glu Thr Arg Glu Val Pro Val Gly Lys Glu Gln Ser
    835                 840                 845

Ser Thr Val Leu Thr Gly Leu Arg Pro Gly Met Glu Tyr Thr Val His
850                 855                 860

Val Trp Ala Gln Lys Gly Asn Gln Glu Ser Lys Lys Ala Asp Thr Lys
865                 870                 875                 880

Ala Gln Thr Glu Ile Asp Gly Pro Lys Asn Leu Val Thr Asp Trp Val
            885                 890                 895

Thr Glu Asn Met Ala Thr Val Ser Trp Asp Pro Val Gln Ala Thr Ile
            900                 905                 910

Asp Lys Tyr Met Val Arg Tyr Thr Ser Ala Asp Gly Glu Thr Arg Glu
    915                 920                 925

Val Pro Val Gly Lys Glu His Ser Ser Thr Val Leu Thr Gly Leu Arg
930                 935                 940
```

Pro Gly Met Glu Tyr Met Val His Val Trp Ala Gln Lys Gly Ala Gln
945                 950                 955                 960

Glu Ser Lys Lys Ala Asp Thr Lys Ala Gln Thr Glu Leu Asp Pro Pro
            965                 970                 975

Arg Asn Leu Arg Pro Ser Ala Val Thr Gln Ser Gly Gly Ile Leu Thr
        980                 985                 990

Trp Thr Pro Pro Ser Ala Gln Ile His Gly Tyr Ile Leu Thr Tyr Gln
    995                 1000                1005

Phe Pro Asp Gly Thr Val Lys Glu Met Gln Leu Gly Arg Glu Asp
1010                1015                1020

Gln Arg Phe Ala Leu Gln Gly Leu Glu Gln Gly Ala Thr Tyr Pro
1025                1030                1035

Val Ser Leu Val Ala Phe Lys Gly Gly Arg Arg Ser Arg Asn Val
1040                1045                1050

Ser Thr Thr Leu Ser Thr Val Gly Ala Arg Phe Pro His Pro Ser
1055                1060                1065

Asp Cys Ser Gln Val Gln Gln Asn Ser Asn Ala Ala Ser Gly Leu
1070                1075                1080

Tyr Thr Ile Tyr Leu His Gly Asp Ala Ser Arg Pro Leu Gln Val
1085                1090                1095

Tyr Cys Asp Met Glu Thr Asp Gly Gly Gly Trp Ile Val Phe Gln
1100                1105                1110

Arg Arg Asn Thr Gly Gln Leu Asp Phe Phe Lys Arg Trp Arg Ser
1115                1120                1125

Tyr Val Glu Gly Phe Gly Asp Pro Met Lys Glu Phe Trp Leu Gly
1130                1135                1140

Leu Asp Lys Leu His Asn Leu Thr Thr Gly Thr Pro Ala Arg Tyr
1145                1150                1155

Glu Val Arg Val Asp Leu Gln Thr Ala Asn Glu Ser Ala Tyr Ala
1160                1165                1170

Ile Tyr Asp Phe Phe Gln Val Ala Ser Ser Lys Glu Arg Tyr Lys
1175                1180                1185

Leu Thr Val Gly Lys Tyr Arg Gly Thr Ala Gly Asp Ala Leu Thr
1190                1195                1200

Tyr His Asn Gly Trp Lys Phe Thr Thr Phe Asp Arg Asp Asn Asp
1205                1210                1215

Ile Ala Leu Ser Asn Cys Ala Leu Thr His His Gly Gly Trp Trp
1220                1225                1230

Tyr Lys Asn Cys His Leu Ala Asn Pro Asn Gly Arg Tyr Gly Glu
1235                1240                1245

Thr Lys His Ser Glu Gly Val Asn Trp Glu Pro Trp Lys Gly His
1250                1255                1260

Glu Phe Ser Ile Pro Tyr Val Glu Leu Lys Ile Arg Pro His Gly
1265                1270                1275

Tyr Ser Arg Glu Pro Val Leu Gly Arg Lys Lys Arg Thr Leu Arg
1280                1285                1290

Gly Arg Leu Arg Thr Phe
1295

<210> SEQ ID NO 7
<211> LENGTH: 2588
<212> TYPE: DNA
<213> ORGANISM: Homo sapiens

<400> SEQUENCE: 7

-continued

```
gatgggattg gggttttccc ctcccatgtg ctcaagactg gcgctaaaag ttttgagctt      60
ctcaaaagtc tagagccacc gtccaggag caggtagctg ctgggctccg gggacacttt     120
gcgttcgggc tgggagcgtg cttttccacga cggtgacacg cttccctgga ttggccagac    180
tgccttccgg gtcactgcca tggaggagcc gcagtcagat cctagcgtcg agccccctct    240
gagtcaggaa acattttcag acctatggaa actacttcct gaaaacaacg ttctgtcccc    300
cttgccgtcc caagcaatgg atgatttgat gctgtcccg gacgatattg aacaatggtt    360
cactgaagac ccaggtccag atgaagctcc cagaatgcca gaggctgctc ccccgtggc    420 ccctgcacca gcagctccta caccggcggc ccctgcacca gcccctcct ggcccctgtc    480 atcttctgtc ccttcccaga aaacctacca gggcagctac ggtttccgtc tgggcttctt    540
gcattctggg acagccaagt ctgtgacttg cacgtactcc cctgccctca caagatgtt    600 ttgccaactg gccaagacct gccctgtgca gctgtgggtt gattccacac cccgcccgg    660 cacccgcgtc cgcgccatgg ccatctacaa gcagtcacag cacatgacgg aggttgtgag    720
gcgctgcccc caccatgagc gctgctcaga tagcgatggt ctggcccctc ctcagcatct    780
tatccgagtg gaaggaaatt tgcgtgtgga gtatttggat gacagaaaca cttttcgaca    840
tagtgtggtg gtgcccctatg agccgcctga ggttggctct gactgtacca ccatccacta    900
caactacatg tgtaacagtt cctgcatggg cggcatgaac cggaggccca tcctcaccat    960
catcacactg gaagactcca gtggtaatct actgggacgg aacagctttg aggtgcgtgt   1020
ttgtgcctgt cctgggagag accggcgcac agaggaagag aatctccgca agaaaggggga   1080 gcctcaccac gagctgcccc cagggagcac taagcgagca ctgcccaaca acaccagctc   1140
ctctccccag ccaaagaaga aaccactgga tggagaatat ttcaccctc agatccgtgg   1200 gcgtgagcgc ttcgagatgt tccgagagct gaatgaggcc ttggaactca aggatgccca   1260
ggctgggaag gagccagggg ggagcagggc tcactccagc cacctgaagt ccaaaaaggg   1320
tcagtctacc tcccgccata aaaaactcat gttcaagaca aagggcctg actcagactg   1380 acattctcca cttcttgttc cccactgaca gcctcccacc cccatctctc cctcccctgc   1440 catttttgggt tttgggtctt tgaacccttg cttgcaatag gtgtgcgtca gaagcaccca   1500
ggacttccat ttgctttgtc ccggggctcc actgaacaag ttggcctgca ctggtgtttt   1560
gttgtgggga ggaggatggg gagtaggaca taccagctta gattttaagg ttttttactgt   1620 gagggatgtt tgggagatgt aagaaatgtt cttgcagtta agggttagtt tacaatcagc   1680
cacattctag gtaggggccc acttcaccgt actaaccagg gaagctgtcc ctcactgttg   1740
aattttctct aacttcaagg cccatatctg tgaaatgctg gcatttgcac ctacctcaca   1800
gagtgcattg tgagggttaa tgaaataatg tacatctggc cttgaaacca cctttattta   1860
catggggtct agaacttgac ccccttgagg gtgcttgttc cctctccctg ttggtcggtg   1920
ggttggtagt ttctacagtt gggcagctgg ttaggtagag ggagttgtca agtctctgct   1980
ggcccagcca aaccctgtct gacaacctct tggtgaacct tagtacctaa aaggaaatct   2040 cacccccatcc cacaccctgg aggatttcat ctcttgtata tgatgatctg gatccaccaa   2100 gacttgttttt atgctcaggg tcaatttctt ttttctttttt tttttttttt tttctttttc   2160
tttgagactg ggtctcgctt tgttgcccag gctggagtgg agtggcgtga tcttggctta   2220
ctgcagcctt tgcctcccg gctcgagcag tcctgcctca gcctccggag tagctgggac   2280
cacaggttca tgccaccatg gccagccaac ttttgcatgt tttgtagaga tggggtctca   2340
```

```
cagtgttgcc caggctggtc tcaaactcct gggctcaggc gatccacctg tctcagcctc   2400
ccagagtgct gggattacaa ttgtgagcca ccacgtccag ctggaagggt caacatcttt   2460
tacattctgc aagcacatct gcattttcac cccaccctct ccctccttct ccctttttat   2520
atcccatttt tatatcgatc tcttatttta caataaaact ttgctgccac ctgtgtgtct   2580
gaggggtg                                                             2588
```

<210> SEQ ID NO 8
<211> LENGTH: 393
<212> TYPE: PRT
<213> ORGANISM: Homo sapiens

<400> SEQUENCE: 8

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
```

```
                325                 330                 335
Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390

<210> SEQ ID NO 9
<211> LENGTH: 9205
<212> TYPE: DNA
<213> ORGANISM: Homo sapiens

<400> SEQUENCE: 9
gagaacggcg cgcgcccgc tcggcagctg cggcggcggc tggtgtaggc gctcacgtca      60
gggctgggag gagggggttc gcagctcaga gagagagaga catgaggcaa cctggcagga    120
agcgagaaag agttcggcga agaaggagtg agttctagag acgccccgcg agcaggaccc    180
gcgcctgcag gagagcctgg ccgacccggc tcctcgcctt ctctgcgcgc tctcccgcgt    240 ccgcttttcag cacccgagc ggagaacagt tcccggcagc ccgcagcgct gccgagtggc    300
cgccggccgg ccgagtaccc ggagctccag ggggctcagg agcaccctct gagaacccgc    360
tgtgcaccca ccttttcccc tcttttggtg ggcaagtaag cacggggggaa aagcatccgg    420 tggcctcagg gagccctgaa gaaaccgaag cagaatgtac cagggacaca tgcagaaaag    480
taaagaacaa ggatatggaa aactaagcag tgatgaagac ctcgaaataa ttgttgatca    540
aaagcaggga aaaggctcta gggcggcaga taaggctgtt gccatggtga tgaaggagat    600
accgagggag gagtctgctg aagaaaagcc cctccttact atgacatcac agctggtgaa    660
tgagcaacaa gaaagcagac ccctcctgag tccctccatc gatgactttc tctgtgaaac    720
caaatcggaa gcaatagcaa ggccagtaac atccaataca gctgtattga ccactggctt    780
agatctcctc gacctgagtg aaccagtctc tcaaacccaa accaaagcca agaagtcaga    840
gccctcatca aaaacctcat ccctcaagaa aaaggccgat ggatctgacc tcatcagcac    900
ggatgctgag cagagaggcc agcctctcag agtcccggag acttcatcct tagatctaga    960
cattcaaaca caactgggaaa aatgggacga tgttaagttt catggagatc gaaataccaa   1020
gggacatcca atggcagaga gaaaatcatc ctcatctaga actggatcaa agagctctt    1080 atggtcctca gaacacagat ctcaaccaga actgagtggt ggaaaaagcg ccctcaactc   1140
tgagtcggct tcagaattgg aattagtggc tccgactcag gctcgactga ccaaagaaca   1200
tcgctgggga agcgcattac tttctagaaa ccactcctta agaagagt tgaaagggc     1260 aaaagcagca gtggagtcag atacagagtt ttgggataag atgcaagcag aatgggaaga   1320
aatggctcgg aggaactgga tatctgagaa ccaagaagcc cagaaccaag taccatctc    1380 ggctagtgag aagggatatt actttcacac tgaaaacccc ttcaaggact ggcctggagc   1440
atttgaagaa ggcttaaaaa ggctgaagga aggggatctg ccagtcacca tcctgttcat   1500
ggaagcagca attcttcagg accctggaga tgcagaggca tggcagttcc tcgggataac   1560
ccaggcggag aatgaaaatg aacaagcagc tattgtcgcc ctccagaggt gcttagaatt   1620
acagcccaac aacttaaaag ctttgatggc cttggctgtg agttatacta acactggcca   1680
tcagcaggat gcctgtgacg ctctgaagaa ttggattaag caaaatccaa agtacaaata   1740
```

```
ccttgtgaaa agcaagaagg gatctccagg cctcacccgg cggatgtcta agtccccagt    1800
tgatagctct gttctggaag gggtgaagga attatatctg gaagctgccc accaaaatgg    1860
agatatgatc gacccagacc tgcagacagg tctaggggtt ctgttccacc tgagtggaga    1920
atttaataga gcaatagatg catttaacgc tgccttaact gttcggccag aggactattc    1980
actatggaac cgcctcgggg cgaccttggc gaacggagac cgcagcgagg aagccgtgga    2040
ggcctatacg cgagcactgg agattcagcc aggattcatc cggtccagat acaacctagg    2100
aataagctgc atcaacctgg gcgcctacag agaagcggtc agcaatttc tcactgccct    2160
cagtttgcaa agaagagca ggaatcagca gcaagttcct catcctgcaa tctctgggaa    2220
tatctgggct gccctcagaa ttgcgctctc tctgatggac caaccagaac tcttccaggc    2280
ggctaatctt ggtgacctgg atgtcctctt aagagctttc aacttggatc cttgaagaaa    2340
gaataatacc agtactaata atccctgatc tgtgtgattg tactgaaaaa tcaaaaacta    2400
ttttattatg aatttcaaaa ggataaatca aatattcaaa aggccatggt catatagccc    2460
aaggaaatta attcctgtgg acaatgccca gtctctgttc agatccaaaa gcacaaaatg    2520
ttgtatatag agtcaaagtc aggctcaaaa gaagaattaa gagactcaag acaaaccaag    2580
ataaagtaac tgtgtgttga atactctttc cacaagttgc aagcatattg caacacatgt    2640
tctttggggtt ttttgtctcc ccttgcagct gatgacacat ctgaggaact tgttcatggg    2700
aaacatggaa aaagcactgc ctcagattgg gaaattctga ctgtttctga actgtcttct    2760
tttgcaagac tgaacatagt ttgggccatt ggtgcatgca catatattaa cttgtgacta    2820
aagacagaca ttgcttaaac ctgttccaat tttaactttt actgtagccc tttgattcca    2880
gagagggagc tttgctggca aaagcagttt ttgcactaga aattttttgct gttcccaatc    2940
taaacttttc tggtattgta tatatgcact ttaatatctt atttatgcct tgctggagtt    3000
ttgttttgtt gctccaattt ttaacttggg ggtgaaagat ttaagaactc agcctcacta    3060
gatcaacgga ccaaataaac aattcctgaa gacagttttt catagtgtag gattttgaag    3120
aagtgttttt cttaaagcag atacgatgac ataaggcgta aatatggcaa acagatcttt    3180
tcattcacgt gctttctggg tctgtatgaa cataagtaag acacaaggta ctgtctcttc    3240
atgcattctc tgcaggaaga aagtttgatg gtatcgtgat ttctattgag ttcaaattaa    3300
cttgcttaag tgtcatactt tactggcttt gccctgcaca ccaatattcc ttttaaacca    3360
taaatatttt aaataatatt tcttaagagt gataaataac attttttcct aaaaattatg    3420
ttttcttagt ttcataataa tctgcactgt tcatcccctt gcattctaag tgatagaaga    3480
gcaaacttt caaaccaaat ctcactgaat gccagtgatt tcatatgaaa gatgcatgcc    3540
tctttggctc tttgaacatt tagcaagtat tgggaatttt ctattagcag tggtgtttta    3600
attggttgaa ttccacttag ttctccacag tgttttgtat gtgtttgggg cttggtgatt    3660
attttgaaag atacatttt taagaattaa ggaacatttt ttgcaaaatg ctaatcagaa    3720
tataatttc ccaatgtcag gtatagaagt tatcccattc ttctttacct ggtctccttc    3780
cttcgtctag aaccttcccc acagtagcta atcctaacaa cttttattt atgttctttg    3840
ataataatag ctcatcccgc tcatgattat agctaccac aaaaaataaa acaacaacaa    3900
caaaaaagac tccacagaat tgggatcaaa acagtctaat tggctgggga ataagcttct    3960
actgaggagt aaatgtgcac acgtgctat caattgaatg cgaggtacag gaataaaatc    4020
ctctcctctg ttacatctga agtccttggg ttgtgagagg gcctcaagtt aacagaaacc    4080
```

```
acaagtcctt gaggcttaca tatgttataa cctattctag tttataaaga caaaaagctg    4140
aggccactgt gaggagtgcc aggttttgat agtcattgtc aaagttgact tgggccaggt    4200
ggtagctcca gctggtcagc agaaggcaga ggcattcagg cactcatcat gggtagcagc    4260
gaccacccag tctcagaccg tgcttctcta cagtctcagc agcaaagtaa agctcaacaa    4320
tgctttcaag aatggtattg taagaattgt agaattcgag aaacccagtc tggtaaggac    4380
tcttggggcc agcctccaag ccatggcagg gcctgcttga atatgcctga ttaagcatcc    4440
tttccttccc tgctccttcc tcctgccatc tctgtacctt gaccagaaag tcggcatgaa    4500
tagttcatgg acaaaggatt gaatagcctc tgaacaaagg attcaaagca aactttgtaa    4560
gtgttctgtg atgccattct atactttgag cagcagctga atctgcagcc tggatttaaa    4620
gcctgaaact agtataaatg tcaaataatt aatttgttgc taaatggtgg caaattttgt    4680
ggcccaagtt ttattttgct attggaacac aaactccaag gagctgtttt agggaagact    4740
aaacaatctt ccattcttac cattatttgg caatttgcag agcatttagt agtactttct    4800
ctagtgtatg tagtatctgt cagatctaag atttttatag gctgtcaaga agtccagaat    4860
tacggcccaa gaggaaaaga gttgcatttt tcaataatat ttttttataaa attaagttaa    4920 aaccattatt aaaacatgag tgacaggcca ggtgcggtgg ctcacgcctg taatcctagc    4980
actttgggag gcagaggcgg gcagaccacg aggtcaggag ttcgagacca gcctgaccaa    5040
catggtgaaa ccccgtcttt attaagaata caaaaattag ccgggtgtag tggtatgcac    5100
ctgtaatacc agctactcag gaggctgagg caggagaatc acttgaacca gggaggcgga    5160
ggttgcagtg agccgagatt gcaccgctgc actccagtct gggtgacaga gcgagactcc    5220
gtctcaaaaa aacaaaaaa gtgacagttt ataggaatag agcaccacca agaaatcagt    5280
agcaagactt tagaacagtc ttttttgtata aatcatatac agtaaatgtt ttgtttctta    5340
gaagtgcatc tactttattt tttggcagaa caattttttgg catcttatct tcatggcatg    5400
aaattgtcat ttaaattact cttttccgttt gaaaggggag ggtatcctta tttcccttct    5460
gaggtactct gagaaggctt tgagtttcct ttttcatgta ttaatgtata acagcctaac    5520
agctcctaga agagggtatt cttactagaa tggctacata cgggtgactt cagttacata    5580
caggtgactt ccagggactg acttcgcctg tagattggat gaaaataaag agaaagccag    5640
tgattattgc tgagtttcaa aatataacca tttctagtag gctacttcta catgctgttg    5700
taccttcctg gtgaggagga gacagaggga taggggagag gaggaggaat aaaaatccct    5760
ctcactgggc caatcatact gattcattcc ctttacttcc tccaaaactc actccccatg    5820
actcctgaaa aatgggtaga tctcgtccac caggaaattt taatagaata ctatgcaccg    5880
tgctttctca gtcaatctgg attcctacta gaacagaaaa gtaaggaaac ataactgggt    5940
aggaatgtcc acttacgttt cacaaactca cttttagagt ttcatgccac tttcctcatt    6000
cttctcttta agatactatt atattgaacg tgggacccat gtctaaatac ttgtatagat    6060
aaatatttct tgtatattct tcccatacaa gcaagacttg aatacagttg tagctagtcc    6120
cacttttata ataaaagctt ccaaactctt tatcataaac tttgtctgtg agcttgggaa    6180
tacagagaaa gcaagttgat cattctgaga cccttcctca tttgccctga atcagttccc    6240
caagattgga ctgtacttta agctagttgt tgtagcagtg gtggttgttg ttttatatct    6300
tgagatactt ctagaacatt ctagaaacag ggtattctaa aggcttactt tatatgccat    6360 ccttttttgaa ccctcttatt ttagaaatta ttacacgtgc acacttatga tttcaacctt    6420
gtaaaataat ttcaaattca tttcgtatcc acattttact gcagtttccc tatcatcatc    6480
```

```
tcaatagtta tagaactggt tgaaattaaa ctgttttgaa ctaagaagta gatatatata    6540
tatatatata tatatatttt tttttttttt tttaaagagt gttcatagat aaactctggc    6600
ataaagtttg taaaaaagca attttttaaa agcaaaacgt ataacctcag gtacaaaaat    6660
attgcatgca ttagtattgc aaatttgcct actcaaatat taaccaaagc atgcaagata    6720
acttgactga atttaaattt acacagtgca tgattaagtc tcataggtta gcctgttgtt    6780
ccttgcctct atacaaggga gcatttttat gaactttgtg ttacagtttt tctatttgct    6840
tttcttatcc tatccttgag attgttttca tgctatcaca ctgaacttta cagatattca    6900
cacatctggt ttctacagtg ttaccagtgc caaactaatc tctgaagaa tctgggacat     6960 ctaaacactt tttcaaaaac cagttgaggc acaacagatc ccaaacttaa acaaatccaa    7020
gtgtctgaat gctactaaac taaatcatgt tgactgcctc agcacataaa ggtttcgact    7080
ttaaattctt aataatgcat ttcaaaattt ttctaaaagt ttgggaataa attagaaaaa    7140
ctgatattct aaataaggcg aggaggttgg ggtaatgtca ggcacatcaa aatcatcaca    7200
caacgaagta gatatggggc cttaattttc ataaatgtca catagcaagt gtgtggggta    7260
tcacaacatt gttctgatac agccctgttt gtatggtagt tgagctgctt gggctaaatg    7320
tcccttgaga aactggactt gatcaacagg tctaaaaaca ctgatattta gggagtgatg    7380
aggtgatttc acggtcactc agaaccaact ctgaaatctt ctcactgcct tttcccataa    7440
cccctatttt atgaggagac cagaaaggga gagagcaaag ctcagtgaga ccatgtggtc    7500
ttacattagt aacagctttg ttactcactc catataccc ggtaccctca cacacatacc      7560
atgaactcaa agacagaatt ctacacataa cacacatagc aaagacgatt gtggggaggc    7620
attaaacagt taagaggaaa aaaaaaaaca cagaaaatta aactgtgagg tttaacaacc    7680
tctcatgtgg tattttgcct tgaacgaagt ttccactacc tgcagcttct gcagaaatac    7740
caaaataaca cagtctagag acaagtgtcc caatgtcaga actgttttct caggaccttc    7800
tctataagag aaaactaact tgcaatgctg cagaatgtca gagcaaaacc ctgatgagct    7860
ccgtgggata cttaatagaa gcctgcactc aaaataatat taagatggaa acaacaacaa    7920
caattaggca gttctttgct caactataaa atgtgtatca ttcattgggg gagggggagg    7980
ggtcgtgttc tttggatttc ttggaaaggg aaatggtata acacaaaaag actaagaggt    8040
atacacactc agctcggtaa ttcgagcatt tggcattttc actgagatat atagcatttc    8100
tgcatggata ccatacaaga attctgccat gtgagaaatg tgttcatgat ggactacatt    8160
accagtagtt aagggaaata cagcaaactt aagttttac caacttcctt tcatgttccc      8220
tatatatcat ctaacccaaa ctttcaattt acattgccca aatttgttta cattggttga    8280
aaaaaaactg attaatttat taaactttt acaaactgta acaaacattt aactatttag      8340
aaaagacatt tctacatatt ttatatatct atgaatattg catctctaat ctaatctaaa    8400
aatgttgttt tgagacaatt cttctgtgat gcttcctcct catgctcata aatgtttaaa    8460
gtcttgggat ttcattttca ggctgaaata gataacaaga aaaaaattta agtttaaatg    8520
tttacattgc gttactaaat taataccaat tcaaattaag tgacctatag taaattaatg    8580
gcaatggggg ggaggggatt ttaaagtgat tggcatatta tgtgatactg tatcagtgat    8640
ttagtgaaat aatatgtatc atagcacaac tctgttgggt attaaggctt catcttagta    8700
tttccctgcg ttgctctttg aaataaaatt actaccataa aaataacctc ttatcatatt    8760
gatgtgttta atttactcag ttggcttcta atttgcgtaa caagattaag gtagtatttt    8820
```

-continued

```
tgtactatta ttggaagcat gccttccctt tttcacatta ttaaattgta tttatatttg    8880
tgcaatttta aactatgttt tcaaataaac tttgtctgcg gcttcgaggt cttttcagga    8940
atctttcaaa atgggatttg gggatcagaa ctccttctga tcaatggaaa tccaatttgt    9000
actactggct aaaggtcctt ttattaaata ttgaatatca ctacatatga ttttgcatga    9060
gctatctgga atcaggaat gcattttttgg atataaaaca aaactttaaa aatcttcctc     9120
ctttgttaat ttttttaagac taaaatatta tttaacctga aattgaattt tgtgattctt    9180
tttagaataa aaatattaaa ataaa                                          9205
```

<210> SEQ ID NO 10
<211> LENGTH: 626
<212> TYPE: PRT
<213> ORGANISM: Homo sapiens

<400> SEQUENCE: 10

```
Met Tyr Gln Gly His Met Gln Lys Ser Lys Glu Gln Gly Tyr Gly Lys
1               5                   10                  15

Leu Ser Ser Asp Glu Asp Leu Glu Ile Ile Val Asp Gln Lys Gln Gly
            20                  25                  30

Lys Gly Ser Arg Ala Ala Asp Lys Ala Val Ala Met Val Met Lys Glu
        35                  40                  45

Ile Pro Arg Glu Glu Ser Ala Glu Glu Lys Pro Leu Leu Thr Met Thr
    50                  55                  60

Ser Gln Leu Val Asn Glu Gln Gln Glu Ser Arg Pro Leu Leu Ser Pro
65                  70                  75                  80

Ser Ile Asp Asp Phe Leu Cys Glu Thr Lys Ser Glu Ala Ile Ala Arg
                85                  90                  95

Pro Val Thr Ser Asn Thr Ala Val Leu Thr Thr Gly Leu Asp Leu Leu
            100                 105                 110

Asp Leu Ser Glu Pro Val Ser Gln Thr Gln Thr Lys Ala Lys Lys Ser
        115                 120                 125

Glu Pro Ser Ser Lys Thr Ser Ser Leu Lys Lys Lys Ala Asp Gly Ser
    130                 135                 140

Asp Leu Ile Ser Thr Asp Ala Glu Gln Arg Gly Gln Pro Leu Arg Val
145                 150                 155                 160

Pro Glu Thr Ser Ser Leu Asp Leu Asp Ile Gln Thr Gln Leu Glu Lys
                165                 170                 175

Trp Asp Asp Val Lys Phe His Gly Asp Arg Asn Thr Lys Gly His Pro
            180                 185                 190

Met Ala Glu Arg Lys Ser Ser Ser Arg Thr Gly Ser Lys Glu Leu
        195                 200                 205

Leu Trp Ser Ser Glu His Arg Ser Gln Pro Gly Leu Ser Gly Gly Lys
    210                 215                 220

Ser Ala Leu Asn Ser Glu Ser Ala Ser Glu Leu Glu Leu Val Ala Pro
225                 230                 235                 240

Thr Gln Ala Arg Leu Thr Lys Glu His Arg Trp Gly Ser Ala Leu Leu
                245                 250                 255

Ser Arg Asn His Ser Leu Glu Glu Glu Phe Glu Arg Ala Lys Ala Ala
            260                 265                 270

Val Glu Ser Asp Thr Glu Phe Trp Asp Lys Met Gln Ala Glu Trp Glu
        275                 280                 285

Glu Met Ala Arg Arg Asn Trp Ile Ser Glu Asn Gln Glu Ala Gln Asn
    290                 295                 300
```

-continued

```
Gln Val Thr Ile Ser Ala Ser Glu Lys Gly Tyr Tyr Phe His Thr Glu
305                 310                 315                 320

Asn Pro Phe Lys Asp Trp Pro Gly Ala Phe Glu Glu Gly Leu Lys Arg
                325                 330                 335

Leu Lys Glu Gly Asp Leu Pro Val Thr Ile Leu Phe Met Glu Ala Ala
                340                 345                 350

Ile Leu Gln Asp Pro Gly Asp Ala Glu Ala Trp Gln Phe Leu Gly Ile
                355                 360                 365

Thr Gln Ala Glu Asn Glu Asn Glu Gln Ala Ala Ile Val Ala Leu Gln
                370                 375                 380

Arg Cys Leu Glu Leu Gln Pro Asn Asn Leu Lys Ala Leu Met Ala Leu
385                 390                 395                 400

Ala Val Ser Tyr Thr Asn Thr Gly His Gln Gln Asp Ala Cys Asp Ala
                405                 410                 415

Leu Lys Asn Trp Ile Lys Gln Asn Pro Lys Tyr Lys Tyr Leu Val Lys
                420                 425                 430

Ser Lys Lys Gly Ser Pro Gly Leu Thr Arg Arg Met Ser Lys Ser Pro
                435                 440                 445

Val Asp Ser Ser Val Leu Glu Gly Val Lys Glu Leu Tyr Leu Glu Ala
450                 455                 460

Ala His Gln Asn Gly Asp Met Ile Asp Pro Asp Leu Gln Thr Gly Leu
465                 470                 475                 480

Gly Val Leu Phe His Leu Ser Gly Glu Phe Asn Arg Ala Ile Asp Ala
                485                 490                 495

Phe Asn Ala Ala Leu Thr Val Arg Pro Glu Asp Tyr Ser Leu Trp Asn
                500                 505                 510

Arg Leu Gly Ala Thr Leu Ala Asn Gly Asp Arg Ser Glu Glu Ala Val
                515                 520                 525

Glu Ala Tyr Thr Arg Ala Leu Glu Ile Gln Pro Gly Phe Ile Arg Ser
530                 535                 540

Arg Tyr Asn Leu Gly Ile Ser Cys Ile Asn Leu Gly Ala Tyr Arg Glu
545                 550                 555                 560

Ala Val Ser Asn Phe Leu Thr Ala Leu Ser Leu Gln Arg Lys Ser Arg
                565                 570                 575

Asn Gln Gln Gln Val Pro His Pro Ala Ile Ser Gly Asn Ile Trp Ala
                580                 585                 590

Ala Leu Arg Ile Ala Leu Ser Leu Met Asp Gln Pro Glu Leu Phe Gln
                595                 600                 605

Ala Ala Asn Leu Gly Asp Leu Asp Val Leu Leu Arg Ala Phe Asn Leu
610                 615                 620

Asp Pro
625
```

METHODS FOR DETERMINING RESPONSIVENESS TO MEK/ERK INHIBITORS

CROSS REFERENCE TO RELATED APPLICATIONS

This application is a national phase stage of international application PCT/CN2015/075884, which claims priority to Chinese patent application no. 201410135569.9, filed Apr. 4, 2014, the disclosure of which is incorporated herein by reference in their entirety.

FIELD OF THE INVENTION

The present invention generally relates to methods for determining the responsiveness of a subject to treatment with a MEK or ERK inhibitor.

BACKGROUND OF THE INVENTION

The Ras-Raf-MEK-ERK signaling cascade (MEK/ERK pathway) is one of key pro-proliferation and pro-survival pathways. Mutations in the MEK/ERK pathway have been found to lead to uncontrolled growth in many cancers (e.g., melanoma). Compounds that inhibit steps in the MEP/ERK pathway have been used to treat cancer. However, some patients that harbor mutations in MEK/ERK pathway show resistance to MEK or ERK inhibitors.

There is a need for an effective means of determining which patients having mutations in MEK/ERK pathway will resist to treatment of MEK or ERK inhibitors and for incorporating such determination into effective treatment.

BRIEF SUMMARY OF THE INVENTION

In one aspect, the present disclosure provides a method for predicting the responsiveness of a cancer cell to an MEK inhibitor. In certain embodiments, the method comprises detecting the presence of at least one mutation in one or more genes selected from the group consisting of ADAM12, COL14A1, TNN, and TP53, in the cancer cell, by contacting a nucleic acid sample derived from the cancer cell with at least one oligonucleotide which allows specific detection of the mutation; wherein presence of mutation in ADAM12, COL14A1, TNN, TP53 and/or any combination thereof is indicative of decreased responsiveness of the cancer cell to the MEK inhibitor.

In certain embodiments, the cancer cell is derived from a cancer patient.

In certain embodiments, the MEK inhibitor is Trametinib.

In certain embodiments, the mutation in ADAM12 is selected from the group consisting of mutation Q650K, R240L, C440Y, Q228E, H247D, M322I, T97fs, P168L and G308E in ADAM12; the mutation in COL14A1 is selected from the group consisting of mutation R178W, L713_splice, Q1272K, L479I, L1295F, E1024K, P1467S, G737R, K1023T, G966C, S1512fs in COL14A1; the mutation in TNN is selected from the group consisting of mutation V353M, Y296S, A733P, D707Y, D471Y, P1010T, S71L, D457Y, P1155L, R476C, Q872H, Q261L, D798Y, C1237*, D67N and T823S in TNN; the mutation in TP53 is selected from the group consisting of mutation Q331R, C135fs, E285K, V274F, Y220C, P250L, R175H, R248Q, R280K, R248L, C176Y, A307_splice, R273L, R158L, A138fs, H193R, A159D, C277F, R248W, Y220C, V274F, R196*, E224_splice, K164*, M246I, A159V, S241F, C242R, S261_splice, E339* in TP53.

In certain embodiments, the detecting step comprises amplifying at least a portion of the gene with the oligonucleotide as primer, and detecting the amplification product and thereby determining the presence of the mutation in the gene.

In certain embodiments, the detecting step comprises contacting the nucleic acid sample with the oligonucleotide which specifically hybridizes to the mutation of the gene to form a complex, and detecting the formation of the complex and thereby determining the presence of the mutation in the gene.

In anther aspect, the present disclosure provides a method of identifying a likely responder or a likely non-responder to an MEK inhibitor, comprising detecting the presence of at least one mutation in one or more genes selected from the group consisting of ADAM12, COL14A1, TNN, and TP53, in a sample from the patient, by contacting the sample with at least one oligonucleotide which allows specific detection of the mutation; identifying the patient as a likely non-responder to the MEK inhibitor if at least one mutation in in ADAM12, COL14A1, TNN, TP53 and/or any combination thereof is detected in the sample.

In certain embodiments, the MEK inhibitor is Trametinib.

In certain embodiments, the mutation in ADAM12 is selected from the group consisting of mutation Q650K, R240L, C440Y, Q228E, H247D, M322I, T97fs, P168L and G308E in ADAM12; the mutation in COL14A1 is selected from the group consisting of mutation R178W, L713_splice, Q1272K, L479I, L1295F, E1024K, P1467S, G737R, K1023T, G966C, S1512fs in COL14A1; the mutation in TNN is selected from the group consisting of mutation V353M, Y296S, A733P, D707Y, D471Y, P1010T, S71L, D457Y, P1155L, R476C, Q872H, Q261L, D798Y, C1237*, D67N and T823S in TNN; the mutation in TP53 is selected from the group consisting of mutation Q331R, C135fs, E285K, V274F, Y220C, P250L, R175H, R248Q, R280K, R248L, C176Y, A307_splice, R273L, R158L, A138fs, H193R, A159D, C277F, R248W, Y220C, V274F, R196*, E224_splice, K164*, M246I, A159V, S241F, C242R, S261_splice, E339* in TP53.

In certain embodiments, the method further comprises recommending the patient who is identified as a likely non-responder not to be treated with a monotherapy of the ERK inhibitor, or not to be treated with an MEK inhibitor.

In certain embodiments, the method further comprises recommending the patient who is identified as a likely non-responder to be treated with a different MEK inhibitor, or to be treated with a combined therapy of a different MEK inhibitor and an additional therapeutic agent of distinct mechanism.

In certain embodiments, the method further comprises recommending the patient who is identified as a likely responder to be treated with the MEK inhibitor.

In certain embodiments, the sample is a cancer cell or tissue derived from the patient.

In another aspect, the present disclosure provides a method for predicting the responsiveness of a cancer cell to a ERK inhibitor, comprising detecting the presence of at least one mutation in one or more genes selected from the group consisting of ADAM12, PEX5L, TNN and TP53, in the cancer cell, by contacting a nucleic acid sample derived from the cancer cell with at least one oligonucleotide which allows specific detection of the mutation; wherein presence of the mutation in ADAM12, PEX5L, TNN, TP53 and/or any combination thereof is indicative of decreased responsiveness of the cancer cell to the ERK inhibitor.

In certain embodiments, the cancer cell is derived from a cancer patient.

In certain embodiments, the ERK inhibitor is SCH772984.

In certain embodiments, the mutation in ADAM12 is selected from the group consisting of mutation Q650K, R240L, C440Y, Q228E, H247D, M322I, T97fs, P168L and G308E in ADAM12; the mutation in PEX5L is selected from the group consisting of mutation D179N, S229Y, G4E, T89K, Q355E, D39N, L571F, D113N in PEX5L; the mutation in TNN is selected from the group consisting of mutation V353M, Y296S, A733P, D707Y, D471Y, P1010T, S71L, D457Y, P1155L, R476C, Q872H, Q261L, D798Y, C1237*, D67N and T823S in TNN; the mutation in TP53 is selected from the group consisting of mutation Q331R, C135fs, E285K, V274F, Y220C, P250L, R175H, R248Q, R280K, R248L, C176Y, A307_splice, R273L, R158L, A138fs, H193R, A159D, C277F, R248W, Y220C, V274F, R196*, E224_splice, K164*, M246I, A159V, S241F, C242R, S261_splice, E339* in TP53.

In certain embodiments, the detecting step comprises amplifying at least a portion of the gene with the oligonucleotide as primer, and detecting the amplification product and thereby determining the presence of the mutation in the gene.

In certain embodiments, the detecting step comprises contacting the nucleic acid sample with the oligonucleotide which specifically hybridizes to the mutation of the gene to form a complex, and detecting the formation of the complex and thereby determining the presence of the mutation in the gene.

In yet another aspect, the present disclosure provides a method of identifying a likely responder or a likely non-responder to an ERK inhibitor, comprising detecting the presence of at least one mutation in one or more genes selected from the group consisting of ADAM12, PEX5L, TNN and TP53, in a sample from the patient, by contacting the sample with at least one oligonucleotide which allows specific detection of the mutation; identifying the patient as a likely non-responder to the ERK inhibitor if at least one mutation in ADAM12, PEX5L, TNN, TP53 and/or any combination thereof is detected in the sample.

In certain embodiments, the ERK inhibitor is SCH772984.

In certain embodiments, the mutation in ADAM12 is selected from the group consisting of mutation Q650K, R240L, C440Y, Q228E, H247D, M322I, T97fs, P168L and G308E in ADAM12; the mutation in PEX5L is selected from the group consisting of mutation D179N, S229Y, G4E, T89K, Q355E, D39N, L571F, D113N in PEX5L; the mutation in TNN is selected from the group consisting of mutation V353M, Y296S, A733P, D707Y, D471Y, P1010T, S71L, D457Y, P1155L, R476C, Q872H, Q261L, D798Y, C1237*, D67N and T823S in TNN; the mutation in TP53 is selected from the group consisting of mutation Q331R, C135fs, E285K, V274F, Y220C, P250L, R175H, R248Q, R280K, R248L, C176Y, A307_splice, R273L, R158L, A138fs, H193R, A159D, C277F, R248W, Y220C, V274F, R196*, E224_splice, K164*, M246I, A159V, S241F, C242R, S261_splice, E339* in TP53.

In certain embodiments, the method further comprises recommending the patient who is identified as a likely non-responder not to be treated with a monotherapy of the ERK inhibitor, or not to be treated with an ERK inhibitor.

In certain embodiments, the method further comprises recommending the patient who is identified as a likely non-responder to be treated with a different ERK inhibitor, or to be treated with a combined therapy of a different ERK inhibitor and an additional therapeutic agent of distinct mechanism.

In certain embodiments, the sample is a cancer cell or tissue derived from the patient.

In another aspect, the present disclosure provides a kit comprising at least one oligonucleotide useful for determining the presence of at least one mutation in one or more genes selected from the group consisting of ADAM12, COL14A1, TNN, TP53, ITGB, and PEX5L.

In certain embodiments, the at least one oligonucleotide comprises a first oligonucleotide useful for determining the presence of at least one mutation in ADAM12, a second oligonucleotide useful for determining the presence of at least one mutation in COL14L1, a third oligonucleotide useful for determining the presence of at least one mutation in TNN, a fourth oligonucleotide useful for determining the presence of at least one mutation in TP53, or any combination thereof.

In certain embodiments, the at least one oligonucleotide comprises a first oligonucleotide useful for determining the presence of at least one mutation in ADAM12, a second oligonucleotide useful for determining the presence of at least one mutation in PEX5L, a third oligonucleotide useful for determining the presence of at least one mutation in TNN, a fourth oligonucleotide useful for determining the presence of at least one mutation in TP53, and or combination thereof.

In certain embodiments, the at least one oligonucleotide comprises a pair of primer useful for amplifying at least a portion of the gene sequence, or comprises a probe useful for specifically hybridizing to the mutation of the gene to form a complex.

In another aspect, the present disclosure provides use of at least one oligonucleotide in the manufacture of a kit for predicting the responsiveness of a cancer cell or a cancer patient to an MEK inhibitor or a ERK inhibitor, wherein the oligonucleotide is useful for detecting the presence of at least one mutation in one or more genes selected from the group consisting of ADAM12, COL14A1, TNN, TP53, and PEX5L.

DETAILED DESCRIPTION OF THE INVENTION

Figure 1:
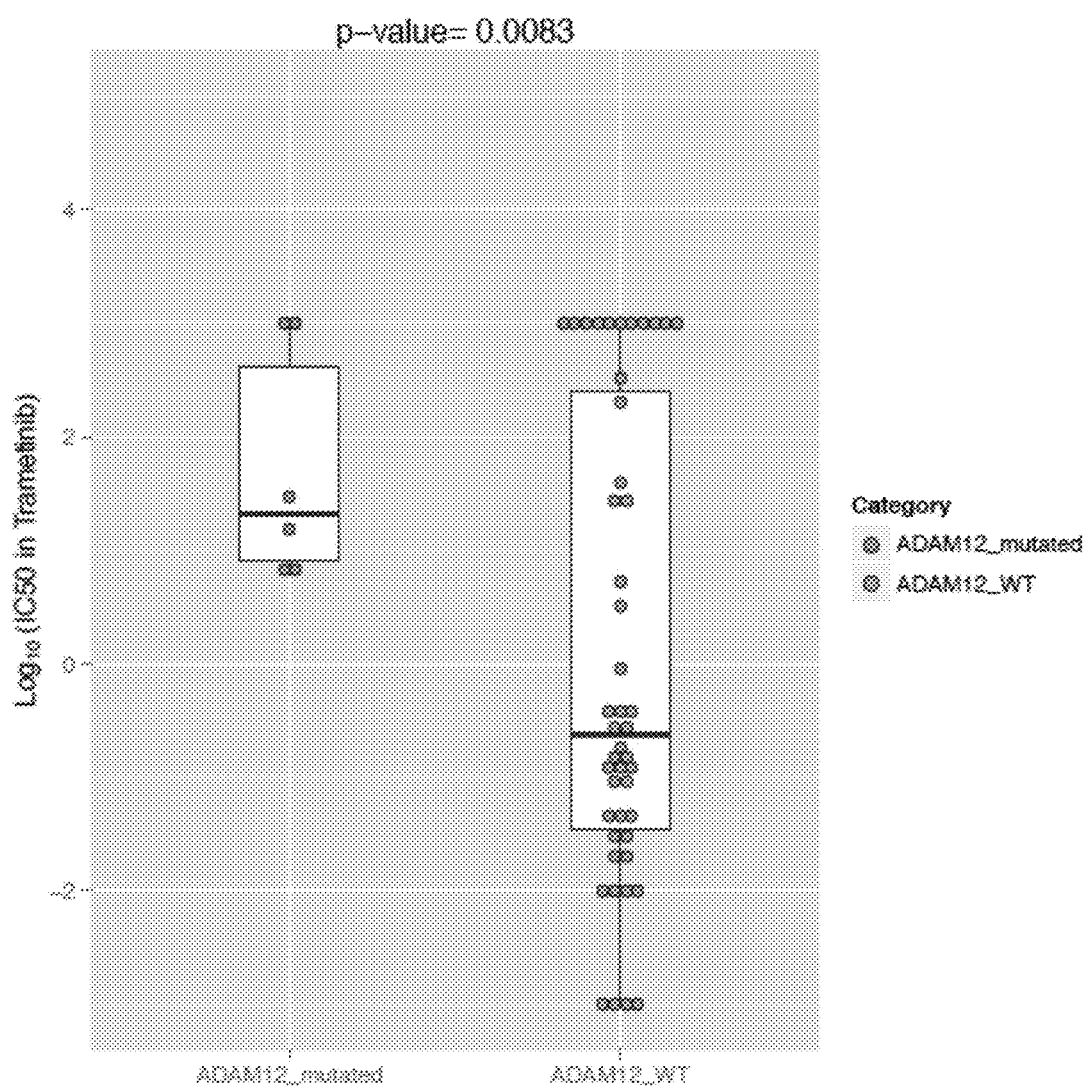
FIG. 1 illustrates the increased sensitivity to MEK inhibitor Trametinib in cells harboring mutations in ADAM12 gene.

In one aspect, the present disclosure provides a method for predicting the responsiveness of a cancer cell to an MEK inhibitor. In certain embodiments, the method comprises detecting the presence of at least one mutation in one or more genes selected from the group consisting of ADAM12, COL14A1, TNN, and TP53, in the cancer cell, by contacting a nucleic acid sample derived from the cancer cell with at least one oligonucleotide which allows specific detection of the mutation; wherein presence of mutation in ADAM12, COL14A1, TNN, TP53 and/or any combination thereof is indicative of decreased responsiveness of the cancer cell to the ERK inhibitor.

The mitogen-activated extracellular signal-regulated kinase (MEK)-extracellular regulated protein kinases (ERK) cascade, also known as Ras-Raf-MEK-ERK signaling pathway, is one of the key signaling pathways involved in tumor oncogenic growth and progression. The signal pathway starts when a signaling molecule (e.g., a growth factor) binds to the receptor on the cell surface. This triggers Ras (a GTPase) to sap its GDP for a GTP. The GTP-bound Ras then activate Raf, which activates MEK, which activates ERK. ERK then activates some proteins, such as myc, that control cell division and cell survival. When one or more proteins in the pathway, such as Ras, are mutated, it can lead to the signaling pathway stuck in the activated status, which is a necessary step in the development of many cancers. As a result, inhibitors of the MEK/ERK signaling pathway have been developed to treat cancer. Certain patients have been found resistant to MEK or ERK inhibitors. The mechanisms underlying resistance to these inhibitors are unclear.

Multiple MEK and ERK1/2 inhibitors are currently under clinical investigation for cancer treatment and more agents targeting MEK or ERK1/2 are under preclinical development. Examples of MEK inhibitors include without limitation Trametinib (GSK1120212), Selumetinib, Binimetinib (MEK162), PD-325901, Cobimetinib (GDC-0973, XL518), and CI-1040 (PD035901). ERK inhibitors include without limitation SCH772984, FR180204, GDC-0994.

In certain embodiments, the MEK inhibitor is Trametinib. Trametinib (trade name Mekinist) has chemical name N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H)-yl}phenyl)acetamide. The structure of Trametinib is illustrated below.

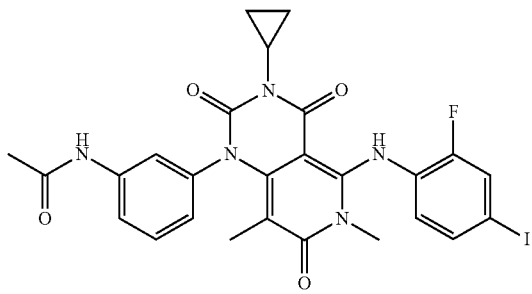 [SMILES: CC(=O)Nc1cccc(-n2c(=O)n(C3CC3)c(=O)c3c(Nc4ccc(I)cc4F)n(C)c(=O)c(C)c32)c1]

As used herein, the term "responsiveness" refers to the likeliness of a cell/individual/patient/subject responding to the treatment of MEK or ERK inhibitor, i.e. showing decreased proliferation/growth and/or increased cell death after being treated with a MEK or ERK inhibitor. In certain embodiments, the responsiveness can be scaled as insensitive (i.e., less likely to respond), sensitive (likely to respond) and uncertain. In certain embodiments, the cell/individual/patient/subject is less likely to respond to a treatment of MEK or ER inhibitor when the cell/individual/patient/subject shows a decreased likeliness that a pathological complete response (pcR), i.e. absence of invasive cancer, will occur. In certain embodiments, the deceased likeliness means about 70%, 60%, 50%, 40%, 30%, 20%, 10% likeliness of the pcR occurred in a reference patient (e.g., a patient without mutation in the gene of interest). In certain embodiments, responsiveness of a cell can be evaluated by measuring IC50 of the cell to a MEK or ERK inhibitor.

As used herein, the term "mutation" refers to the deviation of a genomic DNA from a normal reference (e.g., wild-type genomic DNA), for example, additions, deletions, insertions, rearrangements, inversions, transitions, transversions, frame-shift mutations, nonsense mutations, missense mutations, translocations, and single nucleotide polymorphisms.

Methods of detecting the presence of a mutation in a gene are described herein and known in the art (in general, see e.g., Molecular Cloning A Laboratory Manual, 2nd Ed., ed. By Sambrook, Fritsch and Maniatis, Cold Spring Harbor Laboratory Press, 1989). Examples of the method include, without limitation, sequencing of nucleic acids (e.g., Sanger di-deoxy sequencing, "next generation" sequencing methods and single molecule sequencing), PCR (polymerase chain reaction)-based assay (real-time RCR, PCR-RFLP assay (see Cancer Research 59 (1999), 5169-5175), mass-spectrometric genotyping (e.g. MALDI-TOF), HPLC, enzymatic methods and SSPC (single strand conformation polymorphism analysis (see Pathol Int (1996) 46, 801-804)), hybridization-based assay (e.g., Northern-blot, Southern blot, 5'-exonuclease (TaqMan™) probe, molecular beacons, fluorescence energy transfer probes, Scorpion probes).

In certain embodiments, the method may include enzymatic amplification of DNA or cDNA fragments of the gene to be evaluated by PCR. The resulting PCR products may be subjected to either conventional Sanger-based dideoxy nucleotide sequencing methods or parallel sequencing methods ("next generation sequencing") such as those marketed by Roche (454 technology), Illumina (Solexa technology) ABI (Solid technology) or Invitrogen (IonTorrent). Mutations may be identified from sequence reads by comparison with publicly available gene sequence databases. Alternatively, mutations may be identified by incorporation of allele-specific probes that can either be detected using enzymatic detection reactions, fluorescence, mass spectrometry or others.

In certain embodiments, the method may include amplifying DNA or cDNA fragments of the gene of interest using primers specifically bind to only one of normal and mutated sequence. As a result, amplification product can only be found in one of normal and mutated genes. As such, the presence of the mutation in the gene can be determined by detecting the presence of the amplification product.

In certain embodiments, the method may include contacting the nucleic acid sample with an oligonucleotide probe which specifically hybridizes to the mutation of the gene to form a complex. The oligonucleotide probe can be designed as not hybridizing to the normal sequence of the gene. The presence of the hybridization complex can be detected using reporter signals, e.g., fluorescence. As a result, the presence of the mutation in the gene can be determined by detecting the formation of the complex.

In certain embodiments, the mutation is present in an exon of the gene. In certain embodiment, the presence of the mutation leads to the amino acid change of the polypeptide encoded by the gene. Table 3 shows exemplary nucleic acid sequences of the mutations to be determined in accordance to the present invention. As used herein, a specific mutation is annotated as the resulted amino acid change. For example, mutation Q650K refers to a codon/triplet encoding amino acid K at position 650 of the gene, where amino acid G exists in wild type sequence.

ADAM12 gene (Gene ID: 8038) encodes a member of the ADAM (a disintegrin and metaloprotease) protein family. Members of the ADAM family are membrane-anchored proteins structurally related to snake venom disintegrins, and have been found involved in cell-cell and cell-matrix interactions. ADAM12 gene has two alternative spliced transcripts: a shorter secreted form and a longer member-bound form.

COL14A1 gene (Gene ID: 7373) encodes the alpha chain of type XIV collage, a member of the FACIT (fibril-associated collagens with interrupted triple helices) collagen family. Type XIV collagen interacts with the fibril surface and is involved in the regulation of fribrillogenesis.

TNN gene (Gene ID: 63923) encodes tenascin N precursor. Tenascin is a family of extracellular matrix glycoproteins, whose member has been found to in healing woulds and in the stroma of some tumors.

TP53 gene (Gene ID: 7157) encodes tumor protein p53, which is a tumor suppressor protein containing transcriptional activation, DNA binding, and oligomerization domains. Tumor protein p53 responds to diverse cellular stresses to regulate expression of target genes, thereby inducing cell cycle arrest, apoptosis, senescence, DNA repair, or changes in metabolism. Mutations in TP 53 gene have been found to associate with a variety of cancers. Alternative splicing of TP53 gene and the use of alternate promoters result in multiple transcript variants and isoforms. Additional isoforms have also been shown to result from the use of alternate translation initiation codons. As used herein, position number refers to the sequence of tumor protein p53 isoform a.

In certain embodiments, the mutation in ADAM12 is selected from the group consisting of mutation Q650K, R240L, C440Y, Q228E, H247D, M322I, T97fs, P168L and G308E in ADAM12; the mutation in COL14A1 is selected from the group consisting of mutation R178W, L713_splice, Q1272K, L479I, L1295F, E1024K, P1467S, G737R, K1023T, G966C, S1512fs in COL14A1; the mutation in TNN is selected from the group consisting of mutation V353M, Y296S, A733P, D707Y, D471Y, P1010T, S71L, D457Y, P1155L, R476C, Q872H, Q261L, D798Y, C1237*, D67N and T823S in TNN; the mutation in TP53 is selected from the group consisting of Q331R, C135fs, E285K, V274F, Y220C, P250L, R175H, R248Q, R280K, R248L, C176Y, A307_splice, R273L, R158L, A138fs, H193R, A159D, C277F, R248W, Y220C, V274F, R196*, E224_splice, K164*, M246I, A159V, S241F, C242R, S261_splice, E339* in TP53, wherein "*" means the mutation leads to a stop condon, "fs" means the mutations leads to frame shift, "splice" means the mutation leads to alternative splice of mRNA.

The cancer cell maybe, for example, derived from lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, chronic or acute leukemia, lymphocytic lymphomas, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, including refractory versions of any of the above cancers, or a combination of one or more of the above cancers. In certain embodiments, the cancer cell is derived from a cancer patient.

In anther aspect, the present disclosure provides a method of identifying a likely responder or a likely non-responder to an MEK inhibitor, comprising detecting the presence of at least one mutation in one or more genes selected from the group consisting of ADAM12, COL14A1, TNN, and TP53, in a sample from the patient, by contacting the sample with at least one oligonucleotide which allows specific detection of the mutation; identifying the patient as a likely non-responder to the MEK inhibitor if at least one mutation in ADAM12, COL14A1, TNN, TP53 and/or any combination thereof is detected in the sample.

As used herein, the term "responder" can refer to an individual/patient/subject that is more likely to respond to a treatment using a MEK or ERK inhibitor. "More likely to respond" as used herein refers to an increased likeliness that a pathological complete response will occur in a patient treated with a MEK or ERK inhibitor. The term "non-responder" can refer to an individual/patient/subject that is less likely to respond to a treatment using a MEK or ERK inhibitor. "Less likely to respond" as used herein refers to an decreased likeliness that a pathological complete response will occur in a patient treated with a MEK or ERK inhibitor.

In certain embodiments, in cases where it is assessed that the patient is a likely "responder," said patient is recommended to be treated with an MEK or ERK inhibitor.

In cases where the patient is identified as a likely non-responder, said patient is recommended not to be treated with a monotherapy of the MEK or ERK inhibitor, or not to be treated with an MEK or ERK inhibitor.

In certain embodiments, wherein the patient is identified as a likely non-responder to a MEK inhibitor, the patient is recommended to be treated with a different MEK inhibitor, or to be treated with a combined therapy of a different MEK inhibitor and an additional therapeutic agent of distinct mechanism. Examples of an MEK inhibitor different from Trametinib include, without limitation, Selumetinib, Binimetinib (MEK162), PD-325901, Cobimetinib (GDC-0973, XL518), and CI-1040 (PD035901).

In certain embodiments, the additional therapeutic agent of distinct mechanism can be an agent targeting PI3K-Akt-mTOR signaling pathway. The agents targeting PI3K-Akt-mTOR signaling pathway are known in the art and comprise, without limitation, fused pyrimidine derivatives as disclosed in U.S. Pat. No. 8,022,205 B2 or fused pyrrolopyrimidine derivatives as disclosed in WO2009/099163.

In certain embodiments, the additional agent of distinct mechanism can include c-Met inhibitors (e.g., ARQ197 (taventinib, developed by Daichi Sankyo and ArQule), AMG458 (developed by Amgen), GSK1363089 (also known as XL880 or foretinib, developed GSK), crizotinib (also known as PF2341066, developed by Pfizer), PF04217903 (developed by Pfizer), INCB28060 (developed by Incyte), E7050 (developed by Eisai), MK-2461 (developed by Merck), BMS-777607 (developed by BMS), JNJ-38877605 (developed by Johnson & Johnson), XL184 (developed by BMS/Exelixis)).

In certain embodiments, the additional therapeutic agent of distinct mechanism can be chemotherapeutic agents (e.g., cyclophosphamide (CTX; e.g. Cytoxan®), chlorambucil (CHL; e.g. Leukeran®), cisplatin (CisP; e.g. Platinol®) busulfan (e.g. Myleran®), melphalan, carmustine (BCNU), streptozotocin, triethylenemelamine (TEM), mitomycin C)

In certain embodiments, the additional therapeutic agent of distinct mechanism can be anti-metabolites, such as methotrexate (MTX), etoposide (VP16; e.g. Vepesid®), 6-mercaptopurine (6MP), 6-thioguanine (6TG), cytarabine (Ara-C), 5-fluorouracil (5-FU), capecitabine (e.g. Xeloda®), dacarbazine (DTIC)).

In certain embodiments, the additional therapeutic agent of distinct mechanism can be other antitumor agents, such as paclitaxel (e.g. Taxol®) and pactitaxel derivatives, the cytostatic agents, glucocorticoids such as dexamethasone (DEX; e.g. Decadron®) and corticosteroids such as prednisone, nucleoside enzyme inhibitors such as hydroxyurea, amino acid depleting enzymes such as asparaginase, leucovorin, folinic acid, raltitrexed, and other folic acid derivatives, and similar, diverse antitumor agents.

In certain embodiments, the additional therapeutic agent of distinct mechanism can be anti-hormonal agents (e.g., steroid receptor antagonists, anti-estrogens such as tamoxifen, raloxifene, aromatase inhibiting 4(5)-imidazoles, other aromatase inhibitors, 42-hydroxytamoxifen, trioxifene, keoxifene, LY 117018, onapristone, and toremifene (e.g. Fareston®); anti-androgens such as flutamide, nilutamide, bicalutamide, leuprolide, and goserelin; and pharmaceutically acceptable salts, acids or derivatives of any of the above; agonists and/or antagonists of glycoprotein hormones such as follicle stimulating hormone (FSH), thyroid stimulating hormone (TSH), and luteinizing hormone (LH) and LHRH (leuteinizing hormone-releasing hormone); the LHRH agonist goserelin acetate, commercially available as Zoladex® (AstraZeneca); the LHRH antagonist D-alaninamide N-acetyl-3-(2-naphthalenyl)-D-alanyl-4-chloro-D-phenylalanyl-3-(3-pyridinyl)-D-alanyl-L-seryl-N6-(3-pyridinylcarbonyl)-L-lysyl-N6-(3-pyridinylcarbonyl)-D-lysyl-L-leucyl-N6-(1-methylethyl)-L-lysyl-L-proline (e.g Antide®, Ares-Serono); the LHRH antagonist ganirelix acetate; the steroidal anti-androgens cyproterone acetate (CPA) and megestrol acetate, commercially available as Megace® (Bristol-Myers Oncology); the nonsteroidal anti-androgen flutamide (2-methyl-N-[4, 20-nitro-3-(trifluoromethyl)phenylpropanamide), commercially available as Eulexin® (Schering Corp.); the non-steroidal anti-androgen nilutamide, (5,5-dimethyl-3-[4-nitro-3-(trifluoromethyl-4'-nitrophenyl)-4,4-dimethyl-imidazolidine-dione); and antagonists for other non-permissive receptors, such as antagonists for RAR, RXR, TR, VDR, and the like).

In certain embodiments, the additional therapeutic agent of distinct mechanism can be angiogenesis inhibitors (e.g., VEGFR inhibitors, such as SU-5416 and SU-6668 (Sugen Inc. of South San Francisco, Calif., USA), or as described in, for example International Application Nos. WO 99/24440, WO 99/62890, WO 95/21613, WO 99/61422, WO 98/50356, WO 99/10349, WO 97/32856, WO 97/22596, WO 98/54093, WO 98/02438, WO 99/16755, and WO 98/02437, and U.S. Pat. Nos. 5,883,113, 5,886,020, 5,792,783, 5,834,504 and 6,235,764; VEGF inhibitors such as IM862 (Cytran Inc. of Kirkland, Wash., USA); angiozyme, a synthetic ribozyme from Ribozyme (Boulder, Colo.) and Chiron (Emeryville, Calif.); and antibodies to VEGF, such as bevacizumab (e.g. Avastin™ Genentech, South San Francisco, Calif.), a recombinant humanized antibody to VEGF; integrin receptor antagonists and integrin antagonists, such as to $\alpha_v\beta_3$, $\alpha_v\beta_5$ and $a_v\beta_6$ integrins, and subtypes thereof, e.g. cilengitide (EMD 121974), or the anti-integrin antibodies, such as for example $a_v\beta_3$ specific humanized antibodies (e.g. Vitaxin®); factors such as IFN-alpha (U.S. Pat. Nos. 4,530,901, 4,503,035, and 5,231,176); angiostatin and plasminogen fragments (e.g. kringle 14, kringle 5, kringle 1-3 (O'Reilly, M. S. et al. (1994) Cell 79:315-328; Cao et al. (1996) J. Biol. Chem. 271: 29461-29467; Cao et al. (1997) J. Biol. Chem. 272:22924-22928); endostatin (O'Reilly, M. S. et al. (1997) Cell 88:277; and International Patent Publication No. WO 97/15666); thrombospondin (TSP-1; Frazier, (1991) Curr. Opin. Cell Biol. 3:792); platelet factor 4 (PF4); plasminogen activator/urokinase inhibitors; urokinase receptor antagonists; heparinases; fumagillin analogs such as TNP-4701; suramin and suramin analogs; angiostatic steroids; bFGF antagonists; flk-1 and flt-1 antagonists; anti-angiogenesis agents such as MMP-2 (matrix-metalloprotienase 2) inhibitors and MMP-9 (matrix-metalloprotienase 9) inhibitors).

In certain embodiments, the sample is a cancer cell or tissue derived from the patient.

In another aspect, the present disclosure provides a method for predicting the responsiveness of a cancer cell to a ERK inhibitor, comprising detecting the presence of at least one mutation in one or more genes selected from the group consisting of ADAM12, PEX5L, TNN and TP53, in the cancer cell, by contacting a nucleic acid sample derived from the cancer cell with at least one oligonucleotide which allows specific detection of the mutation; wherein presence of the mutation in ADAM12, PEX5L, TNN, TP53 and/or any combination thereof is indicative of decreased responsiveness of the cancer cell to the ERK inhibitor.

In certain embodiments, the cancer cell is derived from a cancer patient.

In certain embodiments, the ERK inhibitor is SCH772984. SCH772984, with chemical name (R)-1-(2-oxo-2-(4-(4-(pyrimidin-2-yl)phenyl)piperazin-1-yl)ethyl)-N-(3-(pyridin-4-yl)-1H-indazol-5-yl)pyrrolidine-3-carboxamide, is a novel, selective and ATP competitive inhibitor of ERK1/2 (see Morris E J et al., Discovery of a novel ERK inhibitor with activity in models of acquired resistance to BRAF and MEK inhibitors, Cancer Discov. 20133(7): 742-50). The structure of SCH772984 is illustrated as below.

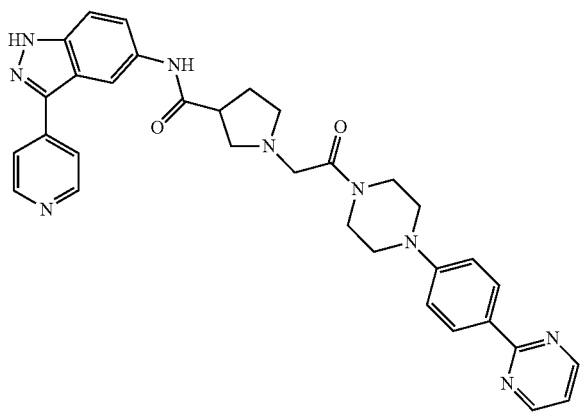 [SMILES: O=C(Nc1ccc2[nH]nc(-c3ccncc3)c2c1)C1CCN(CC(=O)N2CCN(c3ccc(-c4ncccn4)cc3)CC2)C1]

In certain embodiments, the mutation in ADAM12 is selected from the group consisting of mutation Q650K, R240L, C440Y, Q228E, H247D, M322I, T97fs, P168L and G308E in ADAM12; the mutation in PEX5L is selected from the group consisting of mutation D179N, S229Y, G4E, T89K, Q355E, D39N, L571F, D113N in PEX5L; the mutation in TNN is selected from the group consisting of mutation V353M, Y296S, A733P, D707Y, D471Y, P1010T, S71L, D457Y, P1155L, R476C, Q872H, Q261L, D798Y, C1237*, D67N and T823S in TNN; the mutation in TP53 is selected from the group consisting of mutation Q331R, C135fs, E285K, V274F, Y220C, P250L, R175H, R248Q, R280K, R248L, C176Y, A307_splice, R273L, R158L, A138fs, H193R, A159D, C277F, R248W, Y220C, V274F, R196*, E224_splice, K164*, M246I, A159V, S241F, C242R, S261_splice, E339* in TP53.

In certain embodiments, the detecting step comprises amplifying at least a portion of the gene with the oligonucleotide as primer, and detecting the amplification product and thereby determining the presence of the mutation in the gene.

In certain embodiments, the detecting step comprises contacting the nucleic acid sample with the oligonucleotide which specifically hybridizes to the mutation of the gene to form a complex, and detecting the formation of the complex and thereby determining the presence of the mutation in the gene.

In yet another aspect, the present disclosure provides a method of identifying a likely responder or a likely non-responder to an ERK inhibitor, comprising detecting the presence of at least one mutation in one or more genes selected from the group consisting of ADAM12, PEX5L, TNN and TP53, in a sample from the patient, by contacting the sample with at least one oligonucleotide which allows specific detection of the mutation; identifying the patient as a likely non-responder to the ERK inhibitor if at least one mutation in ADAM12, PEX5L, TNN, TP53 and/or any combination thereof is detected in the sample.

In certain embodiments, the method further comprises recommending the patient who is identified as a likely non-responder not to be treated with a monotherapy of the ERK inhibitor, or not to be treated with an ERK inhibitor.

In certain embodiments, the method further comprises recommending the patient who is identified as a likely non-responder to be treated with a different ERK inhibitor, or to be treated with a combined therapy of a different ERK inhibitor and an additional therapeutic agent of distinct mechanism. Examples of ERK inhibitors other than SCH772984 include FR180204, GDC-0994.

In another aspect, the present disclosure provides a kit comprising at least one oligonucleotide useful for determining the presence of at least one mutation in one or more genes selected from the group consisting of ADAM12, COL14A1, TNN, TP53, ITGB, and PEX5L.

In certain embodiments, the at least one oligonucleotide comprises a first oligonucleotide useful for determining the presence of at least one mutation in ADAM12, a second oligonucleotide useful for determining the presence of at least one mutation in COL14L1, a third oligonucleotide useful for determining the presence of at least one mutation in TNN, a fourth oligonucleotide useful for determining the presence of at least one mutation in TP53, or any combination thereof.

In certain embodiments, the at least one oligonucleotide comprises a first oligonucleotide useful for determining the presence of at least one mutation in ADAM12, a second oligonucleotide useful for determining the presence of at least one mutation in PEX5L, a third oligonucleotide useful for determining the presence of at least one mutation in TNN, a fourth oligonucleotide useful for determining the presence of at least one mutation in TP53, and or combination thereof.

In certain embodiments, the at least one oligonucleotide comprises a pair of primer useful for amplifying at least a portion of the gene sequence, or comprises a probe useful for specifically hybridizing to the mutation of the gene to form a complex.

In another aspect, the present disclosure provides use of at least one oligonucleotide in the manufacture of a kit for predicting the responsiveness of a cancer cell or a cancer patient to an ERK inhibitor or a MEK inhibitor, wherein the oligonucleotide is useful for detecting the presence of at least one mutation in one or more genes selected from the group consisting of ADAM12, COL14A1, TNN, TP53, and PEX5L.

Example 1

The following is an example of identifying genes correlated with sensitivity to MEK inhibitors and/or ERK inhibitors.

We examined the anti-proliferation activity of a MEK inhibitor, trametinib, and an ERK1/2 inhibitor, SCH772984, in a panel of 50 cell lines (see Table 1).

TABLE 1

| Cell lines used in the screen | | | | | |
|---|---|---|---|---|---|
| Cancer Type | No. | Cell line | Ras/raf mutation | Growth P. | Medium |
| 1. Breast | 1.1 | BT474 | 150 | Adherent | DMEM + 0.01 mg/ml bovine insulin |
| | 1.2 | DU4475 | 423 | Suspension | RPMI-1640 |

TABLE 1-continued

Cell lines used in the screen

| Cancer Type | No. | Cell line | Ras/raf mutation | Growth P. | Medium |
|---|---|---|---|---|---|
| | 1.3 | MDA-MB-231 | 576 | Adherent | L15 |
| | 1.4 | ZR-75-1 | 493 | Adherent | RPMI-1640 |
| 2. Colorectal | 2.1 | COLO 205 | 591 | Adherent | RPMI-1640 |
| | 2.2 | DLD-1 | 164 | Adherent | RPMI-1640 |
| | 2.3 | HCT-116 | 444 | Adherent | McCoys' 5a |
| | 2.4 | HCT-15 | 627 | Adherent | RPMI-1640 |
| | 2.5 | HCT-8 | 354 | Adherent | RPMI-1640 |
| | 2.6 | HT-29 | 504 | Adherent | McCoys' 5a |
| | 2.7 | KM12 L4 | 779 | Adherent | DMEM |
| | 2.8 | LoVo | 737 | Adherent | F12K |
| | 2.9 | LS513 | 775 | Adherent | RPMI-1640 |
| | 2.1 | RKO | 44 | Adherent | MEM |
| | 2.11 | SW1116 | 42 | Adherent | L15 |
| | 2.12 | SW480 | 237 | Adherent | L15 |
| | 2.13 | SW620 | 590 | Adherent | L15 |
| 3. Liver | 3.1 | Hep G2 | 243 | Adherent | EMEM |
| | 3.2 | HuCCT1 | 396 | Adherent | RPMI-1640 |
| | 3.3 | SK-HEP-1 | 171 | Adherent | MEM + 0.1 mMNEAA |
| | 3.4 | SNU-387 | 287 | Adherent | RPMI-1640 |
| 4. Lung | 4.1 | A549 | 101 | Adherent | F12K |
| | 4.2 | Calu-6 | 254 | Adherent | EMEM |
| | 4.3 | NCI-H1155 | 584 | Suspension | ACL-4 |
| | 4.4 | NCI-H1299 | 577 | Adherent | RPMI-1640 |
| | 4.5 | NCI-H1373 | 360 | Adherent | RPMI-1640 |
| | 4.6 | NCI-H1395 | 386 | Adherent | RPMI-1640 |
| | 4.7 | NCI-H1573 | 426 | Adherent | ACL-4 |
| | 4.8 | NCI-H1651 | 429 | Adherent | ACL-4 |
| | 4.9 | NCI-H1666 | 425 | Adherent | ACL-4 |
| | 4.1 | NCI-H1792 | 400 | Adherent | RPMI-1640 |
| | 4.11 | NCI-H2009 | 513 | Adherent | HITES + 10% FBS |
| | 4.12 | NCI-H2227 | 501 | Adh.&Susp. | HITES + 10% FBS |
| | 4.13 | NCI-H23 | 380 | Adherent | RPMI-1640 |
| | 4.14 | NCI-H358 | 571 | Adherent | RPMI-1640 |
| | 4.15 | NCI-H441 | 759 | Adherent | RPMI-1640 |
| | 4.16 | NCI-H460 | 24 | Adherent | RPMI-1640 |
| | 4.17 | SK-LU-1 | 403 | Adherent | EMEM |
| | 4.18 | SW1271 | 471 | Adherent | L15 |
| 5. Pancreas | 5.1 | AsPC-1 | 736 | Adherent | RPMI-1640 |
| | 5.2 | Capan-1 | 731 | Adherent | IMDM + 20% FBS |
| | 5.3 | CFPAC-1 | 43 | Adherent | IMDM + 20% FBS |
| | 5.4 | MIA PaCa-2 | 167 | Adherent | DMEM + 10% FBS + 2.5% HS |
| | 5.5 | PANC-1 | 156 | Adherent | DMEM |
| 6. Skin | 6.1 | PL45 | 422 | Adherent | DMEM |
| | 6.2 | A2058 | 420 | Adherent | DMEM |
| | 6.3 | A-375 | 716 | Adherent | DMEM |
| | 6.4 | SK-MEL-5 | 154 | Adherent | MEM + 10% FBS + 0.01 mMNEAA |
| 7. Stomach | 7.1 | AGS | 295 | Adherent | F12K |
| | 7.2 | SNU-1 | 292 | Suspension | RPMI-1640 |
| | 7.3 | SNU-719 | 552 | Adherent | RPMI-1640 |

Materials and Methods

Cell Culture

All the cells will be cultured in the media supplemented with 10% FBS except for which are marked specially, in the temperature of 37° C., 5% $CO_2$ and 95% humidity.

Cell Viability Reagent

Cell viability is assayed by using CellTiter-Glo® Luminescent Cell Viability Assay Kit (Cat. No.: G7572, Promega. Store at −20° C.). To prepare the CellTiter_Glo Reagent, the CellTiter-Glo Buffer was thawed and equilibrated to room temperature prior to use. For convenience the CellTiter-Glo Buffer may be thawed and stored at room temperature for up to 48 hours prior to use. The lyophilized CellTiter-Glo Substrate is equilibrated to room temperature prior to use. The appropriate volume (100 ml) of CellTiter-Glo Buffer is transferred into the amber bottle containing CellTiter-Glo Substrate to reconstitute the lyophilized enzyme/substrate mixture, which forms the CellTiter-Glo Reagent. In certain cases, the entire liquid volume of the CellTiter-Glo Buffer bottle may be added to the CellTiter-Glo Substrate vial. Mix by gently vortexing, swirling or by inverting the contents to obtain a homogeneous solution. The CellTiter-Glo Substrate should go into solution easily in less than one minute.

MEK and ERK Inhibitor

MEK inhibitor Trametinib was purchased from Selleckchem (Cat No. 52673) and stored at −20° C. before use. ERK1/2 inhibitor SCH772984 was purchased from Selleckchem (Cat No. 57101) and stored at −20° C. before use.

Equipment

The following equipment was used in the experiments: EnVision Multi Label Reader 2104-0010A, PerkinElmer (USA); Countstar, Inno-Alliance Biotech (USA); Forma Series II Water Jacket CO2 Incubator, Thermo Scientific (USA); Biological safety Cabinet, Thermo Scientific, (USA); Inverted Microscope, Olympus CKX41SF (Japan).

Cytotoxicity and IC50 Determination

The day before the experiment (Day −1), cells were dissociated during the logarithmic growth period with Cell Disassociation Buffer (Gibco 13151-014) and mixed with appropriate cell media and centrifuge at 1000 rpm for 3 minutes. The cells were re-suspended and counted using Countstar before adjusting cell concentrations to optimized density (i.e. $4.44 \times 10^4$ cells/ml) with respective culture medium listed in Table 1 for 3-day CTG assay (The cell density was optimized before actual study; cell density used in the test may vary for different cell lines). 90 μl cell suspensions were added to two 96-well plates (plates A and B) with the final cell density of $4 \times 10^3$ cells/well for 3-day CTG assay (the cell density was optimized before actual study; cell density used in the test may vary for different cell lines). The plate A and B group were incubated for overnight in humidified incubator at 37° C. with 5% $CO_2$.

On Day 0, for plate A group, 10 μl culture medium was added to each well for T0 reading. CellTiter-Glo® Reagent was added at equal volume of cell culture medium present in each well (e.g., add 100 μl of reagent to 100 μl of medium containing cells for a 96-well plate). Contents were mixed for 2 minutes on an orbital shaker to facilitate cell lysis. The plate was allowed to incubate at room temperature for 10 minutes to stabilize luminescent signal. Backseal black sticker was added to the bottom of each plate. Luminescence was recorded using EnVision Multi Label Reader. This formed the basis for T0 value.

On Day 0, the test articles and positive controls were dissolved at the concentration indicated at Test Article Dilution map. 100× solution in PBS was prepared and then diluted with appropriate culture media (1:10) into 10×working solutions. 10 μl (10×) drug solutions were dispensed in each well (triplicate for each drug concentration) of the plate B group according to plate inoculation map. The test plates were incubated for 4 days in the humidified incubator at 37° with 5% $CO_2$.

On Day 3, CellTiter-Glo® Reagent was added at equal volume of cell culture medium present in each well (e.g., add 100 μl of reagent to 100 μl of medium containing cells for a 96-well plate). Contents were mixed for 2 minutes on an orbital shaker to induce cell lysis. The plate was allowed to incubate at room temperature for 10 minutes to stabilize luminescent signal. Backseal black sticker was placed to the bottom of each plate. Luminescence was recorded using EnVision Multi Label Reader.

The data were displayed graphically using GraphPad Prism 5.0. In order to calculate IC50s, a dose-response curve was fitted using a nonlinear regression model with a sigmoidal dose response. The formula for calculating surviving rate was shown below; Absolute IC50 is calculated where Y axis set at 50% using GraphPad Prism 5.0. Software.

The surviving rate(%) = $(Lum_{Test\ article} - Lum_{Medium\ control}) / (Lum_{None\ treated} - LUM_{Medium\ control}) \times 100\%$.

$LUM_{None\ treated} - LUM_{Medium\ control}$ is set as 100% and $LUM_{Medium\ control}$ is set for 0% surviving rate. T0 value was presented as percentage of $Lum_{None\ treated}$.

Statistical Analysis

We divided the 63 cell lines into sensitive, insensitive, and uncertain groups according to their IC50's for SCH772984 and Trametinib, respectively, then detected genes with differential expression or different mutation types between sensitive and insensitive groups. These genes were enriched in several cancer related pathways.

The 63 cell lines were divided into 3 groups (See Table 1): a sensitive group (IC50 values were less than 1), an insensitive group (IC50 values are greater than 10), and an uncertain group (the rest). Accordingly, we got 25 sensitive and 22 insensitive cell lines for SCH772984, and 34 sensitive and 24 insensitive cell lines for Trametinib. Only cell lines with genomic data were used in subsequent analysis. The differentially expressed genes and enriched pathways were analysed using GSEA software, the genes with different mutation types were detected using Fisher's exact test.

Results

Figure 2:
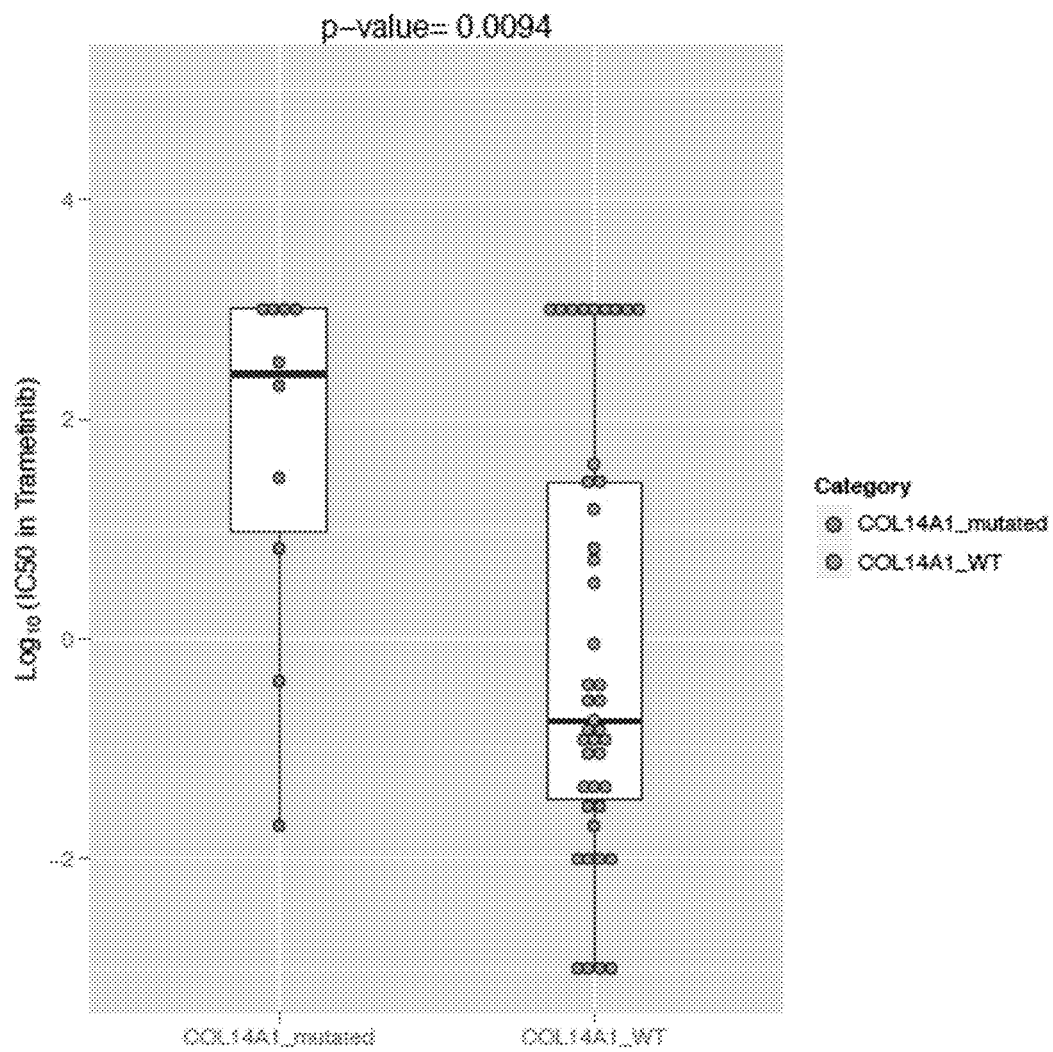
FIG. 2 illustrates the decreased sensitivity to MEK inhibitor Trametinib in cells harboring mutations in COL14A1 gene.
Figure 3:
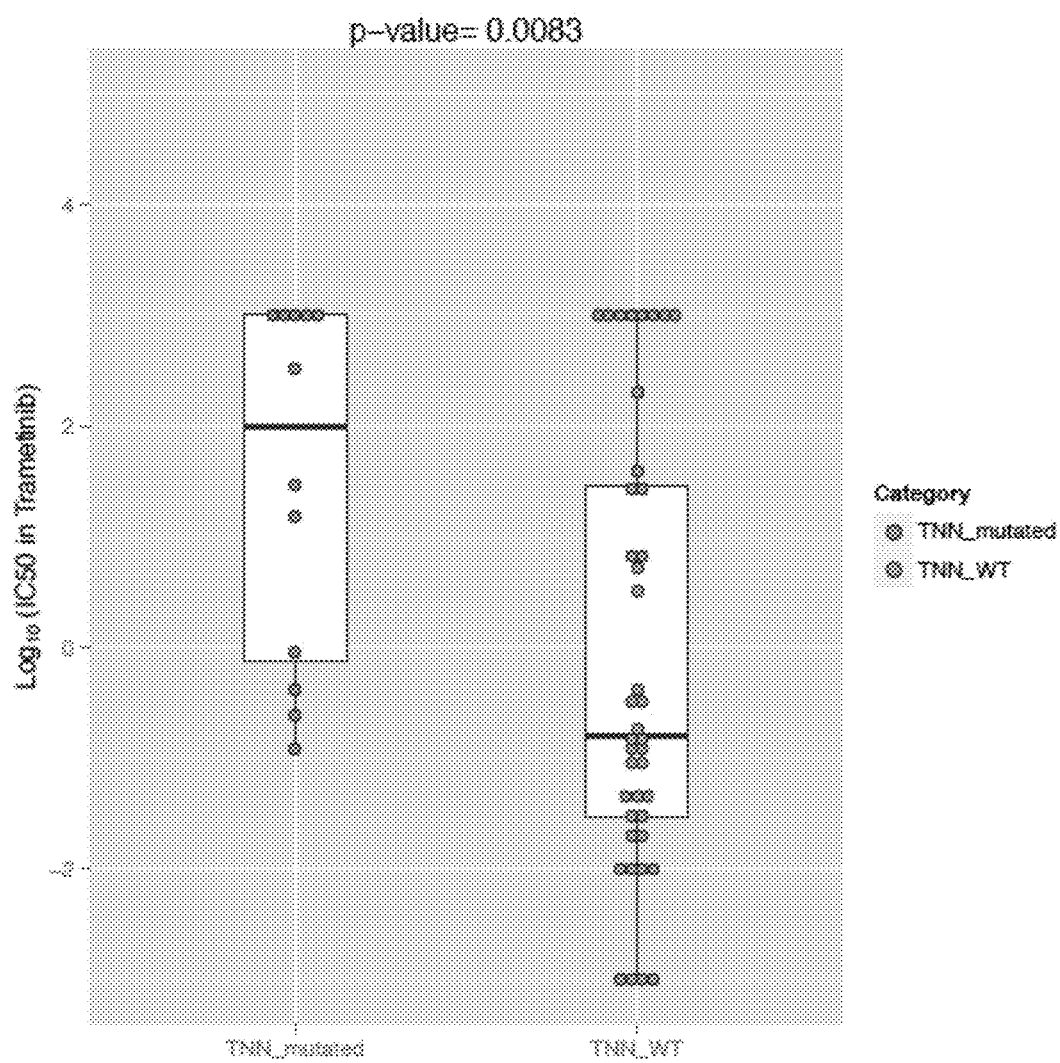
FIG. 3 illustrates the increased sensitivity to MEK inhibitor Trametinib in cells harboring mutations in TNN gene.
Figure 4:
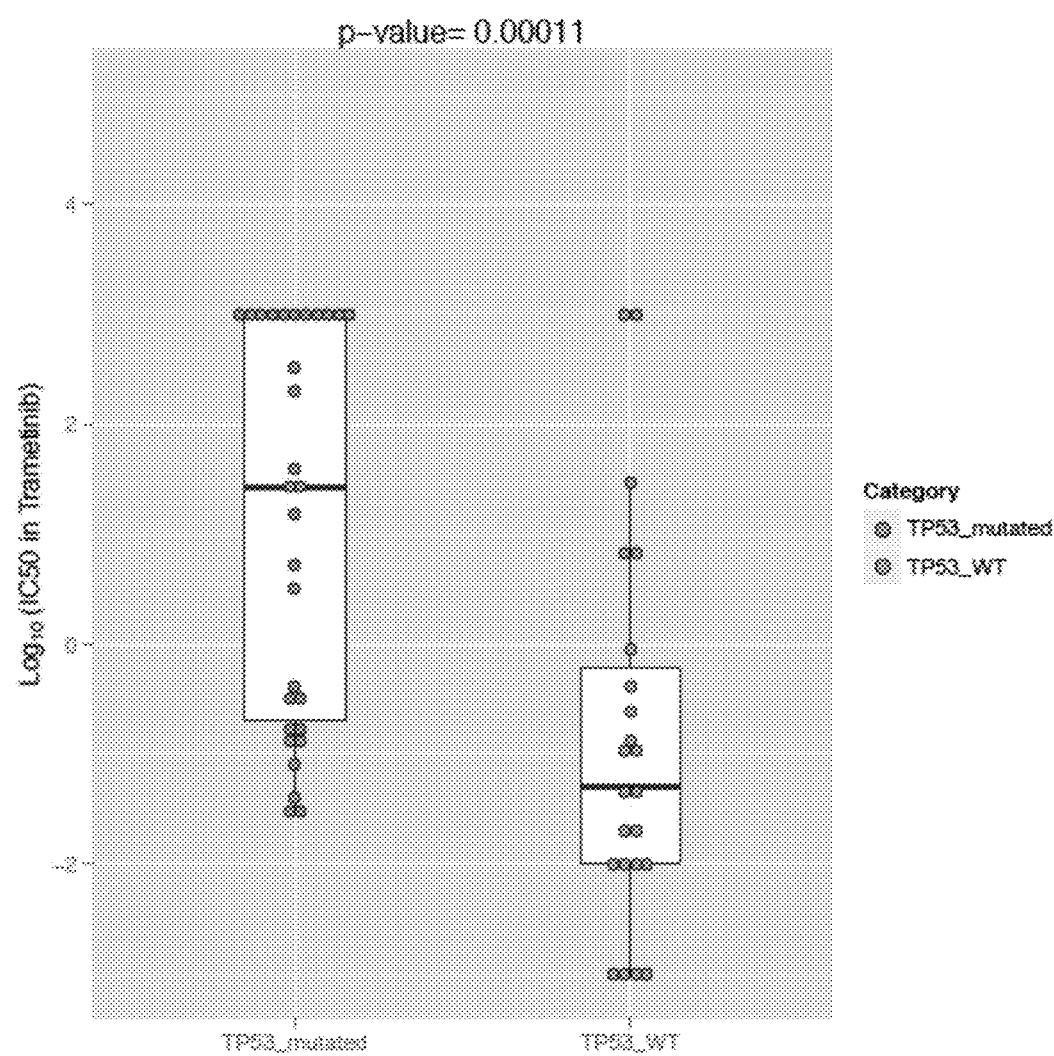
FIG. 4 illustrates the increased sensitivity to MEK inhibitor Trametinib in cells harboring mutations in TP53 gene.
Figure 5:
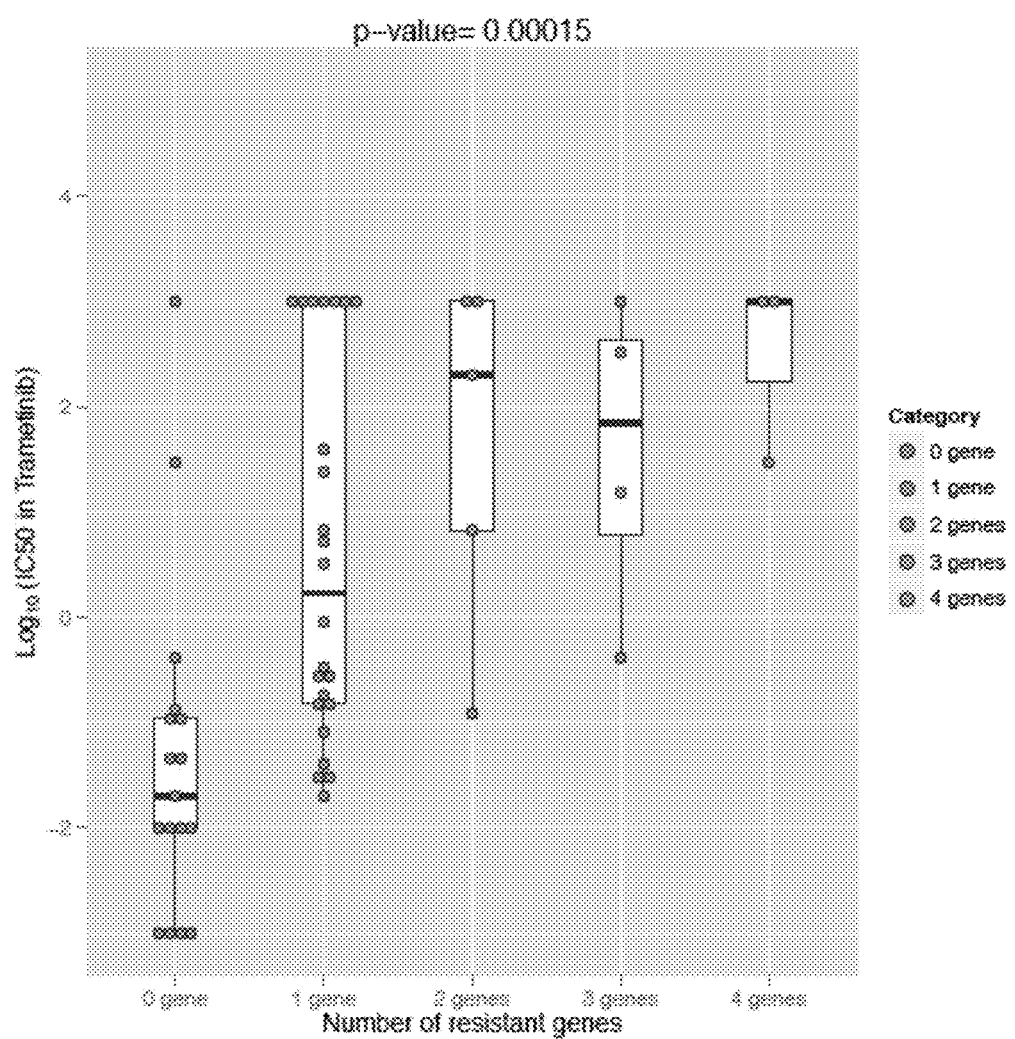
FIG. 5 illustrates the increased sensitivity to MEK inhibitor Trametinib in cells harboring multiple mutations in ADAM12, COL14A1, TNN, and TP53 gene.

For Trametinib, 32 sensitive and 23 insensitive cell lines have gene expression profiled by Affymetrix U219 arrays, 34 gene sets are significantly enriched at nominal p-value <1% (See Table S2). 29 sensitive and 20 insensitive cell lines have mutation information, and ADAM12, COL14A1, TNN and TP53 were identified by P-value cutoff of 0.01 (See Table 3 and FIG. 1-5).

Figure 6:
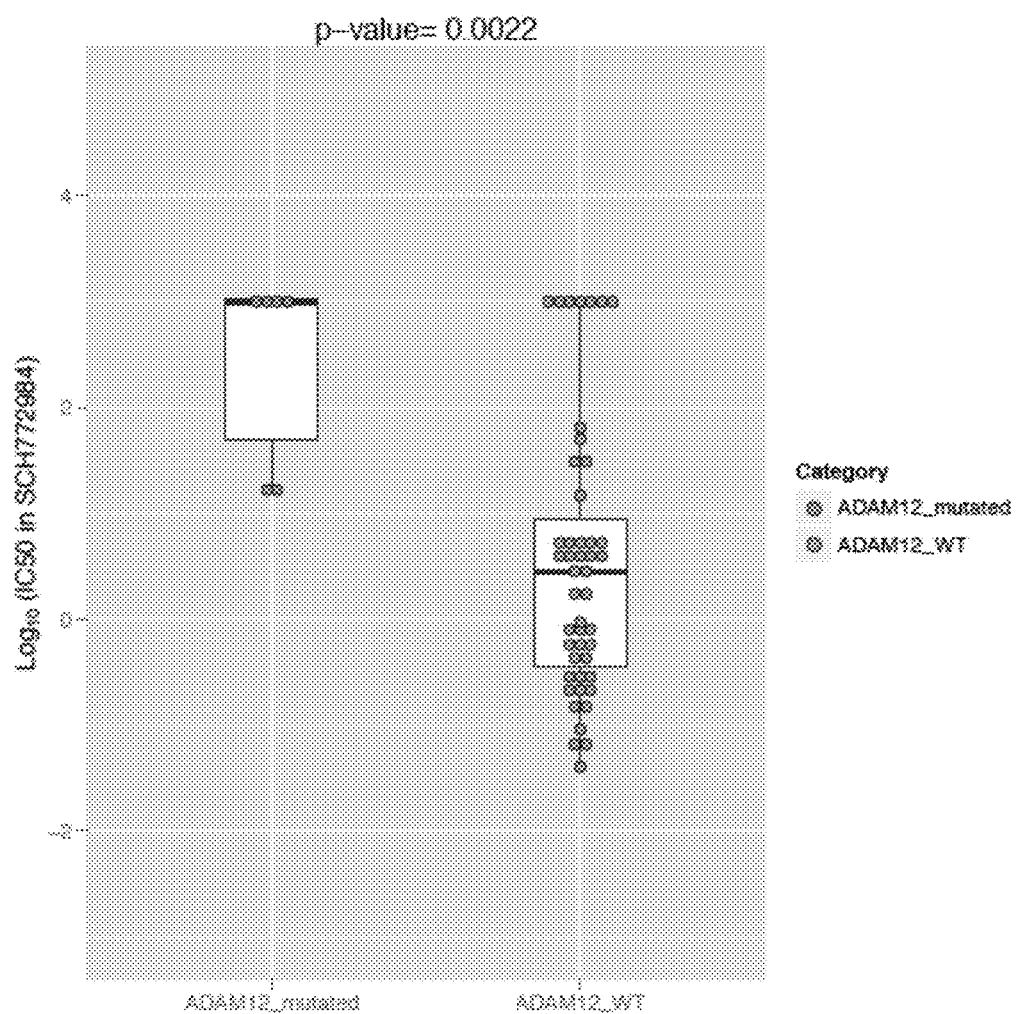
FIG. 6 illustrates the increased sensitivity to ERK inhibitor SCH772984 in cells harboring mutations in ADAM12 gene.
Figure 7:
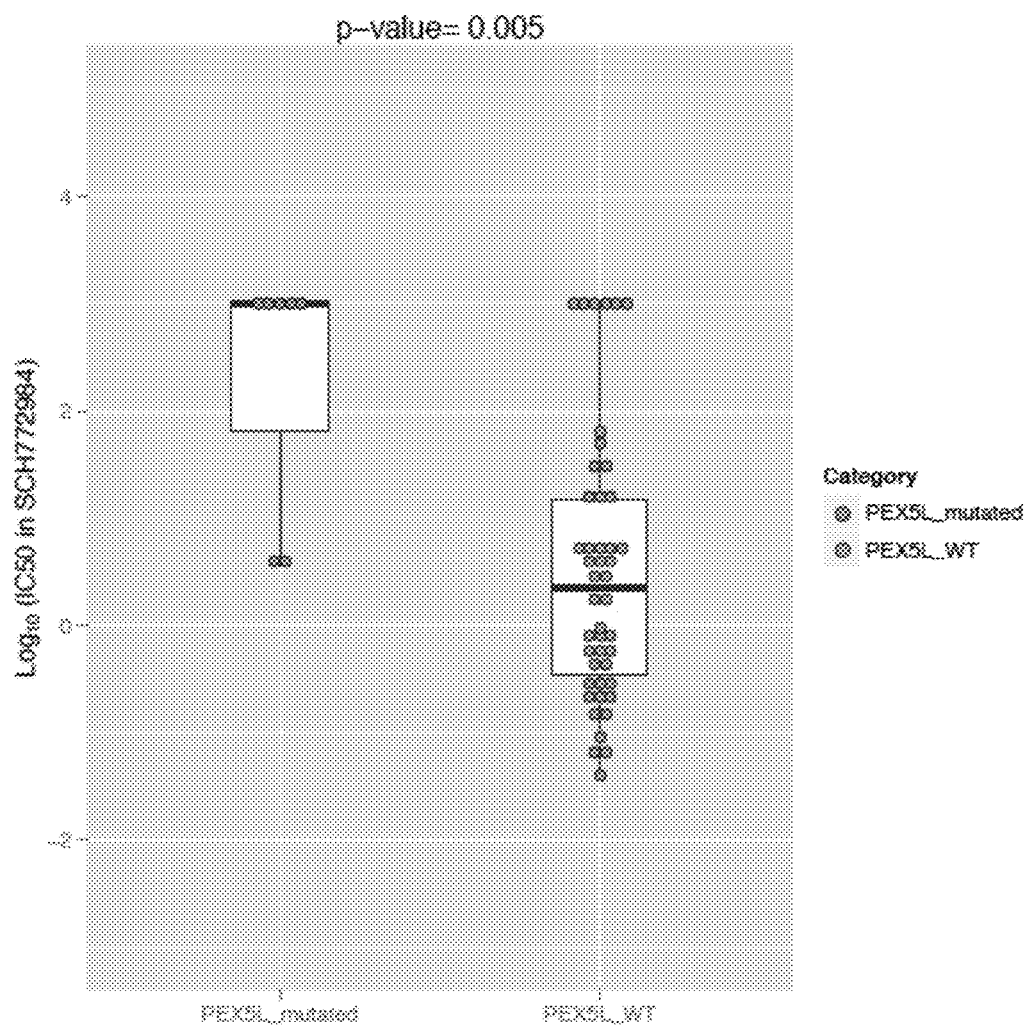
FIG. 7 illustrates the increased sensitivity to ERK inhibitor SCH772984 in cells harboring mutations in PEX5L gene.
Figure 8:
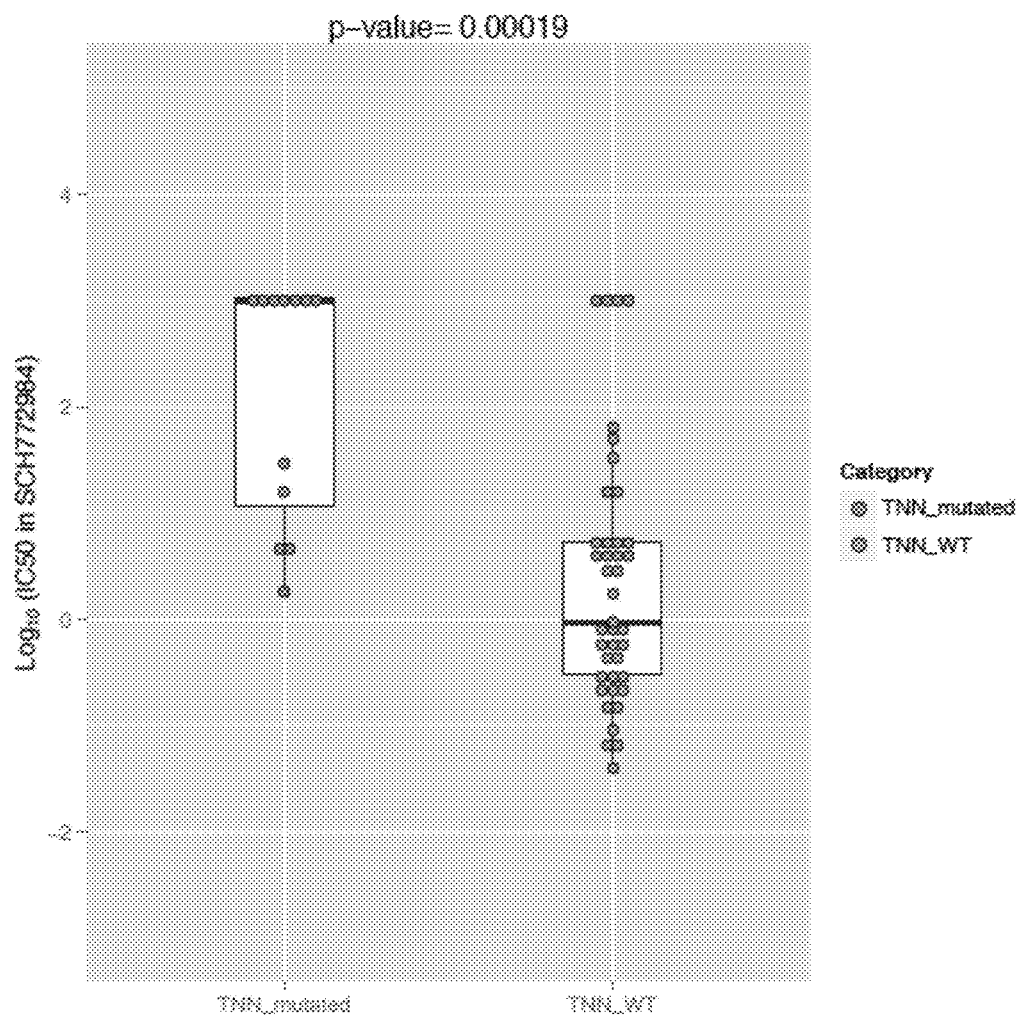
FIG. 8 illustrates the increased sensitivity to ERK inhibitor SCH772984 in cells harboring mutations in TNN gene.
Figure 9:
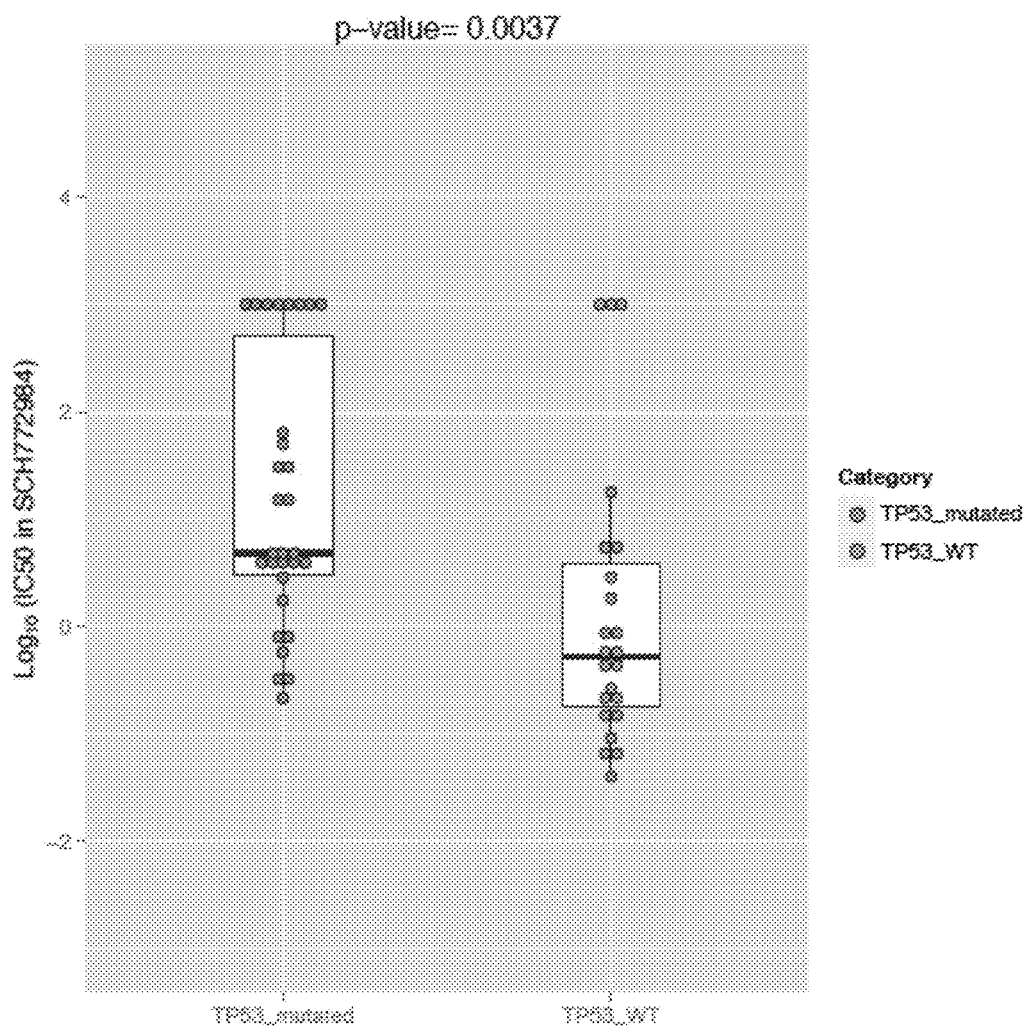
FIG. 9 illustrates the increased sensitivity to ERK inhibitor SCH772984 in cells harboring mutations in TP53 gene.
Figure 10:
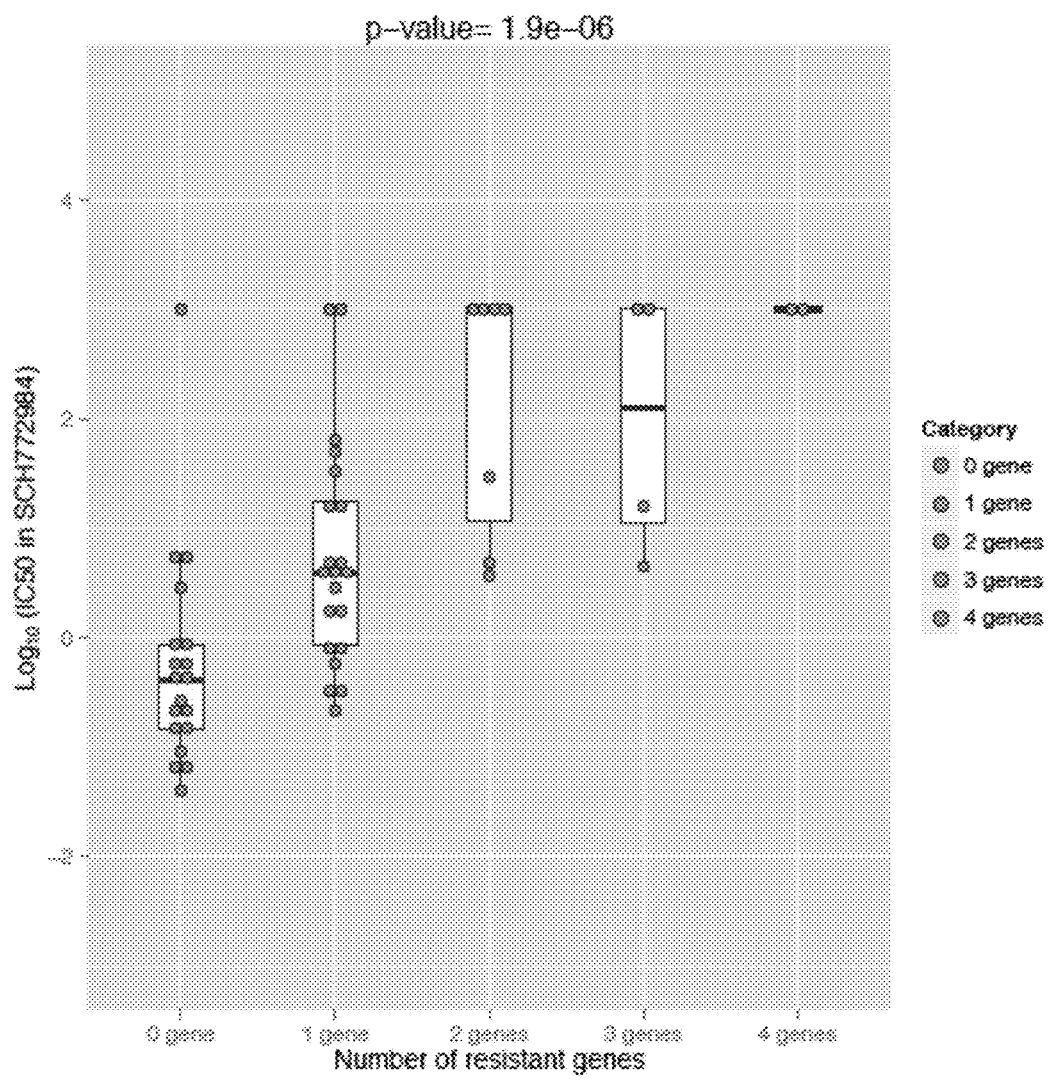
FIG. 10 illustrates the increased sensitivity to ERK inhibitor SCH772984 in cells harboring multiple mutations in ADAM 12, PEX5L, TNN and TP53 gene.

For SCH772984, 23 sensitive and 22 insensitive cell lines have gene expression profiled by Affymetrix U219 arrays, 10 gene sets are significantly enriched at nominal p-value <1%. 21 sensitive and 18 insensitive cell lines have mutation information, and ADAM12, PEX5L, TNN and TP53 were identified by P-value cutoff of 0.01 (See Table 3 and FIGS. 6-10).

TABLE 2

IC50 information

| Number | Cell line | Absolute IC50 (uM) | |
|---|---|---|---|
| | | SCH772984 | Trametinib |
| 1 | A549 | 1.78 | 0.24 |
| 2 | A2058 | NA | 0.12 |
| 3 | Calu6 | 0.56 | 0.14 |
| 4 | DLD-1 | 52.77 | 6.52 |
| 5 | HCT116 | 0.45 | 0.04 |
| 6 | HepG2 | 0.13 | 0.00 |
| 7 | MDA-MB-231 | 32.28 | 23.98 |
| 8 | NCI-H23 | 3.69 | 0.30 |
| 9 | NCI-H460 | 5.53 | NA |
| 10 | RKO | 17.46 | 6.70 |
| 11 | SW620 | 0.26 | 0.01 |
| 12 | SW480 | NA | 6.65 |
| 13 | HCT-8 | 1.27 | 0.05 |
| 14 | HCT-15 | 15.57 | 29.33 |
| 15 | HT29 | 0.23 | 0.01 |
| 16 | LoVo | 0.41 | 0.11 |
| 17 | LS513 | 0.78 | 0.01 |
| 18 | NCI-H358 | 0.52 | 0.05 |
| 19 | NCI-H441 | NA | 324.66 |
| 20 | NCI-H1299 | NA | 0.91 |
| 21 | NCI-H1792 | 4.70 | 0.16 |
| 22 | PANC-1 | 64.31 | 330.05 |
| 23 | Sk-Hep-1 | 5.29 | 29.14 |
| 24 | Sk-Mel-5 | 0.20 | 0.01 |
| 25 | BT474 | NA | 39.00 |
| 26 | Colo205 | 0.04 | 0.00 |
| 27 | KM12L4 | 0.36 | 0.01 |
| 28 | MIAPaCa2 | 0.21 | 0.03 |
| 29 | NCI-H1155 | NA | 636.34 |
| 30 | NCI-H1373 | NA | NA |
| 31 | NCI-H1651 | 48.79 | NA |
| 32 | NCI-H1666 | 0.92 | 0.13 |
| 33 | NCI-H2009 | 4.36 | 0.41 |
| 34 | NCI-H2227 | 28.74 | NA |
| 35 | PL45 | 0.66 | 0.12 |
| 36 | SK-LU-1 | 4.69 | NA |
| 37 | SNU-1 | 0.64 | 0.10 |
| 38 | ZR-75-1 | NA | NA |
| 39 | 22RV1 | 5.01 | 202.02 |
| 40 | BxPc-3 | 0.32 | 0.03 |
| 41 | HCC2935 | NA | NA |

TABLE 2-continued

IC50 information

| | | Absolute IC50 (uM) | |
|---|---|---|---|
| Number | Cell line | SCH772984 | Trametinib |
| 42 | HCC4006 | 2.77 | 0.41 |
| 43 | Hela | 5.38 | NA |
| 44 | Hep3B | 0.25 | 0.05 |
| 45 | HM-7 | 0.79 | 0.39 |
| 46 | HT1376 | 4.27 | NA |
| 47 | KYSE150 | 1.72 | 5.28 |
| 48 | NCI-H1703 | NA | 14.99 |
| 49 | PC-3 | 14.29 | NA |
| 50 | Du145 | NA | NA |

TABLE 3

Gene Mutations Detected in MEK/ERK inhibitor insensitive cell lines.

| Gene | Variant Classification | Variant Type | Tumor Sample | Genome Change |
|---|---|---|---|---|
| ADAM12 | Missense | SNP | DU145 | g.chr10:127734680G>T |
| ADAM12 | Missense | SNP | DU145 | g.chr10:127797193C>A |
| ADAM12 | Missense | SNP | NCIH1573 | g.chr10:127760059C>T |
| ADAM12 | Missense | SNP | NCIH1573 | g.chr10:127797230G>C |
| ADAM12 | Missense | SNP | NCIH1703 | g.chr10:127797173G>C |
| ADAM12 | Missense | SNP | RKO | g.chr10:127787024C>T |
| ADAM12 | Frame Shift Del | DEL | RKO | g.chr10:127843846_127843846delT |
| ADAM12 | Missense | SNP | SW480 | g.chr10:127806716G>A |
| ADAM12 | Missense | SNP | HCT15 | g.chr10:127787067C>T |
| COL14A1 | Missense | SNP | 22RV1 | g.chr8:121209125C>T |
| COL14A1 | Splice Site SNP | SNP | DU145 | g.chr8:121239592G>T |
| COL14A1 | Missense | SNP | DU145 | g.chr8:121293288C>A |
| COL14A1 | Missense | SNP | NCIH1573 | g.chr8:121222108C>A |
| COL14A1 | Missense | SNP | NCIH2009 | g.chr8:121295933C>T |
| COL14A1 | Missense | SNP | NCIH441 | g.chr8:121279119G>A |
| COL14A1 | Missense | SNP | NCIH460 | g.chr8:121313055C>T |
| COL14A1 | Missense | SNP | RKO | g.chr8:121243717G>A |
| COL14A1 | Missense | SNP | SNU719 | g.chr8:121279117A>C |
| COL14A1 | Missense | SNP | HCT15 | g.chr8:121275133G>T |
| COL14A1 | Frame Shift Del | DEL | NCIH1373 | g.chr8:121326250_121326250delC |
| TNN | Missense | SNP | A549 | g.chr1:175052894G>A |
| TNN | Missense | SNP | DU145 | g.chr1:175049401A>C |
| TNN | Missense | SNP | NCIH1573 | g.chr1:175086152G>C |
| TNN | Missense | SNP | NCIH1703 | g.chr1:175067731G>T |
| TNN | Missense | SNP | NCIH2009 | g.chr1:175063212G>T |
| TNN | Missense | SNP | A2058 | g.chr1:175105993C>T |
| TNN | Missense | SNP | HCT15 | g.chr1:175063227C>T |
| TNN | Missense | SNP | HCT15 | g.chr1:175087926G>T |
| TNN | Missense | SNP | NCIH1299 | g.chr1:175063170G>T |
| TNN | Missense | SNP | NCIH1373 | g.chr1:175046753G>A |
| TNN | Missense | SNP | NCIH1373 | g.chr1:175087777A>T |
| TNN | Missense | SNP | NCIH2227 | g.chr1:175048841A>T |
| TNN | Missense | SNP | NCIH2227 | g.chr1:175087702G>T |
| TNN | Nonsense | SNP | NCIH2227 | g.chr1:175113638C>A |
| TNN | Missense | SNP | NCIH441 | g.chr1:175096204C>A |
| TNN | Missense | SNP | SKLU1 | g.chr1:175046766C>T |
| TP53 | Missense | SNP | 22RV1 | g.chr17:7576854T>C |
| TP53 | Frame Shift Del | DEL | ASPC1 | g.chr17:7578527_7578527delA |
| TP53 | Missense | SNP | BT474 | g.chr17:7577085C>T |
| TP53 | Missense | SNP | A2058 | g.chr17:7577118C>A |
| TP53 | Missense | SNP | BXPC3 | g.chr17:7578190T>C |
| TP53 | Nonsense | SNP | CALU6 | g.chr17:7578263G>A |
| TP53 | Missense | SNP | CAPAN1 | g.chr17:7578454G>A |
| TP53 | Missense | SNP | CFPAC1 | g.chr17:7577557A>G |
| TP53 | Missense | SNP | DU145 | g.chr17:7577118C>A |
| TP53 | Missense | SNP | HCC2935 | g.chr17:7578190T>C |
| TP53 | Missense | SNP | HT1376 | g.chr17:7577532G>A |
| TP53 | Missense | SNP | MDAMB231 | g.chr17:7577099C>T |
| TP53 | Missense | SNP | MIAPACA2 | g.chr17:7577539G>A |
| TP53 | Missense | SNP | NCIH1651 | g.chr17:7578403C>T |
| TP53 | Splice Site SNP | SNP | NCIH1703 | g.chr17:7577018C>A |
| TP53 | Splice Site SNP | SNP | NCIH1792 | g.chr17:7578176C>T |
| TP53 | Splice Site SNP | SNP | NCIH2227 | g.chr17:7577157T>G |
| TP53 | Missense | SNP | NCIH23 | g.chr17:7577543C>G |
| TP53 | Missense | SNP | NCIH441 | g.chr17:7578457C>A |
| TP53 | Frame Shift Del | DEL | PC3 | g.chr17:7578516_7578516delG |
| TP53 | Missense | SNP | SKLU1 | g.chr17:7578271T>C |
| TP53 | Nonsense | SNP | SNU387 | g.chr17:7578440T>A |
| TP53 | Missense | SNP | HUCCT1 | g.chr17:7578406C>T |

TABLE 3-continued

Gene Mutations Detected in MEK/ERK inhibitor insensitive cell lines.

| | | | | |
|---|---|---|---|---|
| TP53 | Missense | SNP | NCIH1573 | g.chr17:7577538C>A |
| TP53 | Missense | SNP | NCIH2009 | g.chr17:7577120C>A |
| TP53 | Missense | SNP | SW1116 | g.chr17:7578454G>T |
| TP53 | Missense | SNP | SW1271 | g.chr17:7577108C>A |
| TP53 | Missense | SNP | MIAPACA2 | g.chr17:7577539G>A |
| PEX5L | Missense | SNP | BT474 | g.chr3:179593236C>T |
| PEX5L | Missense | SNP | DU145 | g.chr3:179592155G>T |
| PEX5L | Missense | SNP | NCIH1573 | g.chr3:179754377C>T |
| PEX5L | Missense | DNP | NCIH2009 | g.chr3:179605504_179605505GG>TT |
| PEX5L | Missense | SNP | NCIH441 | g.chr3:179533669G>C |
| PEX5L | Missense | SNP | NCIH441 | g.chr3:179616013C>T |
| PEX5L | Missense | SNP | SW1271 | g.chr3:179519784C>A |
| PEX5L | Missense | SNP | NCIH1299 | g.chr3:179597885C>T |

| Gene | cDNA_Change | Codon_Change | Protein_Change |
|---|---|---|---|
| ADAM12 | c.1948C>A | c.(1948-1950)CAA>AAA | p.Q650K |
| ADAM12 | c.719G>T | c.(718-720)CGA>CTA | p.R240L |
| ADAM12 | c.1319G>A | c.(1318-1320)TGT>TAT | p.C440Y |
| ADAM12 | c.682C>G | c.(682-684)CAG>GAG | p.Q228E |
| ADAM12 | c.739C>G | c.(739-741)CAC>GAC | p.H247D |
| ADAM12 | c.966G>A | c.(964-966)ATG>ATA | p.M322I |
| ADAM12 | c.289_289delA | c.(289-291)ACCfs | p.T97fs |
| ADAM12 | c.503C>T | c.(502-504)CCA>CTA | p.P168L |
| ADAM12 | c.923G>A | c.(922-924)GGG>GAG | p.G308E |
| COL14A1 | c.532C>T | c.(532-534)CGG>TGG | p.R178W |
| COL14A1 | c.2137_splice | | p.L713_splice |
| COL14A1 | c.3814C>A | c.(3814-3816)CAG>AAG | p.Q1272K |
| COL14A1 | c.1435C>A | c.(1435-1437)CTA>ATA | p.L479I |
| COL14A1 | c.3883C>T | c.(3883-3885)CTT>TTT | p.L1295F |
| COL14A1 | c.3070G>A | c.(3070-3072)GAA>AAA | p.E1024K |
| COL14A1 | c.4399C>T | c.(4399-4401)CCA>TCA | p.P1467S |
| COL14A1 | c.2209G>A | c.(2209-2211)GGA>AGA | p.G737R |
| COL14A1 | c.3068A>C | c.(3067-3069)AAA>ACA | p.K1023T |
| COL14A1 | c.2896G>T | c.(2896-2898)GGT>TGT | p.G966C |
| COL14A1 | c.4535_4535delC | c.(4534-4536)TCCfs | p.S1512fs |
| TNN | c.1057G>A | c.(1057-1059)GTG>ATG | p.V353M |
| TNN | c.887A>C | c.(886-888)TAC>TCC | p.Y296S |
| TNN | c.2197G>C | c.(2197-2199)GCC>CCC | p.A733P |
| TNN | c.2119G>T | c.(2119-2121)GAC>TAC | p.D707Y |
| TNN | c.1411G>T | c.(1411-1413)GAC>TAC | p.D471Y |
| TNN | c.3464C>T | c.(3463-3465)CCA>CTA | p.P1155L |
| TNN | c.1426C>T | c.(1426-1428)CGC>TGC | p.R476C |
| TNN | c.2616G>T | c.(2614-2616)CAG>CAT | p.Q872H |
| TNN | c.1369G>T | c.(1369-1371)GAC>TAC | p.D457Y |
| TNN | c.199G>A | c.(199-201)GAC>AAC | p.D67N |
| TNN | c.2467A>T | c.(2467-2469)ACC>TCC | p.T823S |
| TNN | c.782A>T | c.(781-783)CAG>CTG | p.Q261L |
| TNN | c.2392G>T | c.(2392-2394)GAC>TAC | p.D798Y |
| TNN | c.3711C>A | c.(3709-3711)TGC>TGA | p.C1237* |
| TNN | c.3028C>A | c.(3028-3030)CCA>ACA | p.P1010T |
| TNN | c.212C>T | c.(211-213)TCG>TTG | p.S71L |
| TP53 | c.992A>G | c.(991-993)CAG>CGG | p.Q331R |
| TP53 | c.403_403delT | c.(403-405)TGCfs | p.C135fs |
| TP53 | c.853G>A | c.(403-405)TGCfs | pE285K |
| TP53 | c.820G>T | c.(820-822)GTT>TTT | p.V274F |
| TP53 | c.659A>G | c.(658-660)TAT>TGT | p.Y220C |
| TP53 | c.586C>T | c.(586-588)CGA>TGA | p.R196* |
| TP53 | c.476C>T | c.(475-477)GCC>GTC | p.A159V |
| TP53 | c.724T>C | c.(724-726)TGC>CGC | p.C242R |
| TP53 | c.820G>T | c.(820-822)GTT>TTT | p.V274F |
| TP53 | c.659A>G | c.(658-660)TAT>TGT | p.Y220C |
| TP53 | c.749C>T | c.(748-750)CCC>CTC | p.P250L |
| TP53 | c.839G>A | c.(838-840)AGA>AAA | p.R280K |
| TP53 | c.742C>T | c.(742-744)CGG>TGG | p.R248W |
| TP53 | c.527G>A | c.(526-528)TGC>TAC | p.C176Y |
| TP53 | c.919_splice | c.e8+1 | p.A307_splice |
| TP53 | c.672_splice | c.e6+1 | p.E224_splice |
| TP53 | c.783_splice | c.e8−1 | p.S261_splice |
| TP53 | c.738G>C | c.(736-738)ATG>ATC | p.M246I |
| TP53 | c.473G>T | c.(472-474)CGC>CTC | p.R158L |
| TP53 | c.414_414delC | c.(412-414)GCCfs | p.A138fs |
| TP53 | c.578A>G | c.(577-579)CAT>CGT | p.H193R |
| TP53 | c.490A>T | c.(490-492)AAG>TAG | p.K164* |
| TP53 | c.524G>A | c.(523-525)CGC>CAC | p.R175H |
| TP53 | c.743G>T | c.(742-744)CGG>CTG | p.R248L |
| TP53 | c.818G>T | c.(817-819)CGT>CTT | p.R273L |
| TP53 | c.476C>A | c.(475-477)GCC>GAC | p.A159D |

TABLE 3-continued

Gene Mutations Detected in MEK/ERK inhibitor insensitive cell lines.

| | | | |
|---|---|---|---|
| TP53 | c.830G>T | c.(829-831)TGT>TTT | p.C277F |
| TP53 | c.742C>T | c.(742-744)CGG>TGG | p.R248W |
| PEX5L | c.535G>A | c.(535-537)GAT>AAT | p.D179N |
| PEX5L | c.686C>A | c.(685-687)TCT>TAT | p.S229Y |
| PEX5L | c.11G>A | c.(10-12)GGA>GAA | p.G4E |
| PEX5L | c.266_267CC>AA | c.(265-267)ACC>AAA | p.T89K |
| PEX5L | c.1063C>G | c.(1063-1065)CAG>GAG | p.Q355E |
| PEX5L | c.115G>A | c.(115-117)GAT>AAT | p.D39N |
| PEX5L | c.1713G>T | c.(1711-1713)TTG>TTT | p.L571F |
| PEX5L | c.337G>A | c.(337-339)GAC>AAC | p.D113N |

While the invention has been particularly shown and described with reference to specific embodiments (some of which are preferred embodiments), it should be understood by those having skill in the art that various changes in form and detail may be made therein without departing from the spirit and scope of the present invention as disclosed herein.

What is claimed is:

1. A method for treating a patient having cancer, comprising:
   obtaining a sample derived from the patient;
   detecting in the sample that the ADAM12 gene encodes Q650, R240, C440, Q228, H247, M322, T97, P168, and G308 in the ADAM12 protein and does not have a mutation which results in Q650K, R240L, C440Y, Q228E, H247D, M322I, T97fs, P168L, and G308E in the ADAM12 protein; and
   administering an MEK inhibitor to the patient.

2. The method of claim 1, wherein the sample is a cancer cell or tissue derived from the patient.

3. The method of claim 1, wherein the MEK inhibitor is Trametinib.

4. The method of claim 1, wherein the detecting step comprises amplifying at least a portion of the ADAM12 gene with an oligonucleotide as primer to generate an amplification product.

5. The method of claim 1, wherein the detecting step comprises contacting the sample with an oligonucleotide which specifically hybridizes to the mutation of ADAM12 gene to form a complex.

6. The method of claim 1, wherein the detecting step involves an assay selected from the group consisting of sequencing, polymerase chain reaction (PCR), mass-spectrometric genotyping, HPLC, SSPC and a hybridization-based assay.

7. The method of claim 1, wherein the detecting step further comprises determining if the patient has a second mutation in one or more genes selected from the group consisting of COL14A1, TNN, and TP53.

8. The method of claim 7, wherein the mutation in COL14A1 gene results in R178W, L713_splice, Q1272K, L479I, L1295F, E1024K, P1467S, G737R, K1023T, G966C, or S1512fs in COL14A1 protein; wherein the mutation in TNN gene results in V353M, Y296S, A733P, D707Y, D471Y, P1010T, S71L, D457Y, P1155L, R476C, Q872H, Q261L, D798Y, C1237*, D67N or T823S in TNN protein; wherein the mutation in TP53 gene results in Q331R, C135fs, E285K, V274F, Y220C, P250L, R175H, R248Q, R280K, R248L, C176Y, A307_splice, R273L, R158L, A138fs, H193R, A159D, C277F, R248W, Y220C, V274F, R196*, E224_splice, K164*, M246I, A159V, S241F, C242R, S261_splice, or E339* in TP53 protein.

9. A method for treating a patient having cancer, comprising:
obtaining a sample derived from the patient;
detecting in the sample that the ADAM12 gene encodes a mutation which results in Q650K, R240L, C440Y, Q228E, H247D, M322I, T97fs, P168L, and G308E in the ADAM12 protein; and
administering a therapeutic agent to the patient, wherein the therapeutic agent is selected from the group consisting of a c-Met inhibitor, an agent targeting PI3K-Akt-mTOR signaling pathway, a chemotherapeutic agent, an anti-metabolite, an anti-hormonal agent, and an angiogenesis inhibitor.

10. The method of claim 9, wherein the sample is a cancer cell or tissue derived from the patient.

11. The method of claim 9, wherein the detecting step comprises amplifying at least a portion of the ADAM12 gene with an oligonucleotide as primer to generate an amplification product.

12. The method of claim 9, wherein the detecting step comprises contacting the sample with an oligonucleotide which specifically hybridizes to the mutation of ADAM12 gene to form a complex.

13. The method of claim 9, wherein the detecting step involves an assay selected from the group consisting of sequencing, polymerase chain reaction (PCR), mass-spectrometric genotyping, HPLC, SSPC and a hybridization-based assay.

14. The method of claim 9, wherein the detecting step further comprises determining if the patient has a second mutation in one or more genes selected from the group consisting of COL14A1, TNN, and TP53.

15. The method of claim 14, wherein the mutation in COL14A1 gene results in R178W, L713_splice, Q1272K, L479I, L1295F, E1024K, P1467S, G737R, K1023T, G966C, or S1512fs in COL14A1 protein; wherein the mutation in TNN gene results in V353M, Y296S, A733P, D707Y, D471Y, P1010T, S71L, D457Y, P1155L, R476C, Q872H, Q261L, D798Y, C1237*, D67N or T823S in TNN protein; wherein the mutation in TP53 gene results in Q331R, C135fs, E285K, V274F, Y220C, P250L, R175H, R248Q, R280K, R248L, C176Y, A307_splice, R273L, R158L, A138fs, H193R, A159D, C277F, R248W, Y220C, V274F, R196*, E224_splice, K164*, M246I, A159V, S241F, C242R, S261_splice, or E339* in TP53 protein.

* * * * *